United States Patent
Frankenbach et al.

(10) Patent No.: US 10,113,140 B2
(45) Date of Patent: *Oct. 30, 2018

(54) FRESHENING COMPOSITIONS AND DEVICES COMPRISING SAME

(71) Applicant: The Procter & Gamble Company, Cincinnati, OH (US)

(72) Inventors: Gayle Marie Frankenbach, Cincinnati, OH (US); Judith Ann Hollingshead, Batavia, OH (US); Steven Anthony Horenziak, Cincinnati, OH (US)

(73) Assignee: The procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 14/865,066

(22) Filed: Sep. 25, 2015

(65) Prior Publication Data

US 2016/0089465 A1    Mar. 31, 2016

Related U.S. Application Data

(60) Provisional application No. 62/055,844, filed on Sep. 26, 2014, provisional application No. 62/143,862, filed on Apr. 7, 2015.

(51) Int. Cl.
*C11D 3/00* (2006.01)
*A61K 8/33* (2006.01)
(Continued)

(52) U.S. Cl.
CPC .............. *C11D 3/0068* (2013.01); *A61K 8/11* (2013.01); *A61K 8/31* (2013.01); *A61K 8/33* (2013.01); *A61K 8/34* (2013.01); *A61K 8/342* (2013.01); *A61K 8/35* (2013.01); *A61K 8/36* (2013.01); *A61K 8/361* (2013.01); *A61K 8/368* (2013.01); *A61K 8/37* (2013.01); *A61K 8/494* (2013.01); *A61K 8/498* (2013.01); *A61K 8/4926* (2013.01); *A61K 8/4966* (2013.01); *A61K 8/4973* (2013.01); *A61K 8/58* (2013.01); *A61K 8/731* (2013.01); *A61K 8/8152* (2013.01); *A61L 2/18* (2013.01); *A61L 9/01* (2013.01); *A61L 9/012* (2013.01); *A61L 9/03* (2013.01); *A61L 9/122* (2013.01); *A61L 9/127* (2013.01); *A61L 15/20* (2013.01); *A61L 15/28* (2013.01); *A61L 15/46* (2013.01); *A61Q 5/02* (2013.01); *A61Q 13/00* (2013.01); *A61Q 15/00* (2013.01); *A61Q 19/00* (2013.01); *A61Q 19/10* (2013.01); *B01J 20/24* (2013.01); *C08K 5/0008* (2013.01); *C11B 9/003* (2013.01); *C11B 9/008* (2013.01); *C11B 9/0015* (2013.01); *C11B 9/0019* (2013.01); *C11B 9/0034* (2013.01); *C11B 9/0038* (2013.01); *C11B 9/0042* (2013.01); *C11B 9/0049* (2013.01); *C11B 9/0053* (2013.01); *C11B 9/0061* (2013.01); *C11B 9/0076* (2013.01); *C11B 9/0092* (2013.01); *C11D 3/001* (2013.01); *C11D 3/184* (2013.01); *C11D 3/2034* (2013.01); *C11D 3/2068* (2013.01); *C11D 3/2072* (2013.01); *C11D 3/2079* (2013.01); *C11D 3/2093* (2013.01); *C11D 3/2096* (2013.01);
(Continued)

(58) Field of Classification Search
CPC ... C11B 9/0015; C11B 9/0053; C11B 9/0034; C11B 9/003; C11B 9/0038; C11B 9/0019; D06B 1/02; C08K 5/0008; G06F 17/5018; G06F 19/701; G06F 17/10; G06Q 99/00; A61Q 19/00; A61Q 15/00; A61Q 5/02; A61Q 19/10; A61Q 13/00; A61L 9/012; A61L 2/18; A61L 9/03; A61L 9/122; A61L 9/127; A61L 9/01; A61K 8/33; A61K 8/498; A61K 8/4973; A61K 8/37; A61K 8/361; A61K 8/35; A61K 8/4926; A61K 8/36; A61K 8/342; A61K 8/34; A61K 8/31; A61K 8/368; A61K 2800/5922; C11D 3/001; C11D 3/43; C11D 3/2096; C11D 3/2093; C11D 3/2068; C11D 17/042; C11D 3/2034; C11D 3/184; C11D 3/0068; C11D 3/2072; C11D 3/2079; C11D 3/222; C11D 3/30; C11D 3/50; C11D 17/06; C11D 3/505; C11D 11/0017

See application file for complete search history.

(56) References Cited

U.S. PATENT DOCUMENTS 2,438,091 A    3/1948    Lynch
2,528,378 A    10/1950   Mannheimer
(Continued)

FOREIGN PATENT DOCUMENTS

BE    825146 A1    8/1975
CA    1164347 A    3/1984
(Continued)

OTHER PUBLICATIONS

ASTM D3954-94, Reapproved 2010, vol. 15.04, Standard Test Method for Dropping Point of Waxes.
(Continued)

*Primary Examiner* — Blessing M Fubara
(74) *Attorney, Agent, or Firm* — Abbey A. Lopez

(57) ABSTRACT

The present invention relates to freshening compositions and devices comprising same that comprise a composition comprising malodor reduction compositions and methods of making and using such compositions. Such malodor control technologies do not unduly interfere with the scent of the perfumed or unperfumed situs that is treated with the malodor control technology.

15 Claims, No Drawings

(51) Int. Cl.

| | | |
|---|---|---|
| A61K 8/35 | (2006.01) | |
| A61K 8/36 | (2006.01) | |
| A61K 8/37 | (2006.01) | |
| A61K 8/49 | (2006.01) | |
| A61K 8/58 | (2006.01) | |
| A61Q 15/00 | (2006.01) | |
| A61Q 19/10 | (2006.01) | |
| A61L 9/12 | (2006.01) | |
| A61L 9/03 | (2006.01) | |
| C08K 5/00 | (2006.01) | |
| G06F 19/00 | (2018.01) | |
| A61K 8/31 | (2006.01) | |
| A61K 8/34 | (2006.01) | |
| A61Q 5/02 | (2006.01) | |
| A61L 2/18 | (2006.01) | |
| D06B 1/02 | (2006.01) | |
| A61L 9/01 | (2006.01) | |
| A61L 9/012 | (2006.01) | |
| C11D 3/18 | (2006.01) | |
| C11D 3/20 | (2006.01) | |
| C11D 3/43 | (2006.01) | |
| C11D 17/04 | (2006.01) | |
| C11D 3/22 | (2006.01) | |
| C11D 3/30 | (2006.01) | |
| C11D 3/50 | (2006.01) | |
| C11D 17/06 | (2006.01) | |
| A61K 8/368 | (2006.01) | |
| C11B 9/00 | (2006.01) | |
| G06F 17/10 | (2006.01) | |
| G06Q 99/00 | (2006.01) | |
| A61Q 19/00 | (2006.01) | |
| A61Q 13/00 | (2006.01) | |
| C11D 11/00 | (2006.01) | |
| G06F 17/50 | (2006.01) | |
| A61L 15/20 | (2006.01) | |
| A61L 15/28 | (2006.01) | |
| A61L 15/46 | (2006.01) | |
| B01J 20/24 | (2006.01) | |
| C11D 17/00 | (2006.01) | |
| G06F 17/11 | (2006.01) | |
| A61K 8/11 | (2006.01) | |
| A61K 8/73 | (2006.01) | |
| A61K 8/81 | (2006.01) | |

(52) U.S. Cl.
CPC ............... *C11D 3/222* (2013.01); *C11D 3/30* (2013.01); *C11D 3/43* (2013.01); *C11D 3/50* (2013.01); *C11D 3/505* (2013.01); *C11D 11/0017* (2013.01); *C11D 17/0043* (2013.01); *C11D 17/042* (2013.01); *C11D 17/047* (2013.01); *C11D 17/06* (2013.01); *D06B 1/02* (2013.01); *G06F 17/10* (2013.01); *G06F 17/11* (2013.01); *G06F 17/5018* (2013.01); *G06F 19/701* (2013.01); *G06F 19/705* (2013.01); *G06Q 99/00* (2013.01); *A61K 2800/56* (2013.01); *A61K 2800/592* (2013.01); *A61K 2800/5922* (2013.01); *A61L 2209/21* (2013.01); *A61L 2300/62* (2013.01)

(56) References Cited

U.S. PATENT DOCUMENTS

| | | |
|---|---|---|
| 2,658,072 A | 11/1953 | Kosmin |
| 2,809,971 A | 10/1957 | Bernstein et al. |
| 3,236,733 A | 2/1966 | Karsten et al. |
| 3,716,498 A | 2/1973 | Hall |
| 3,753,196 A | 8/1973 | Kurtz et al. |
| 3,761,418 A | 9/1973 | Parran, Jr. |
| 3,792,068 A | 2/1974 | Luedders et al. |
| 3,887,692 A | 6/1975 | Gilman |
| 3,904,741 A | 9/1975 | Jones et al. |
| 4,049,792 A | 9/1977 | Elsnau |
| 4,120,948 A | 10/1978 | Shelton |
| 4,137,180 A | 1/1979 | Naik et al. |
| 4,237,155 A | 12/1980 | Kardouche |
| 4,323,683 A | 4/1982 | Bolich, Jr. et al. |
| 4,345,080 A | 8/1982 | Bolich, Jr. |
| 4,359,456 A | 11/1982 | Gosling et al. |
| 4,379,753 A | 4/1983 | Bolich, Jr. |
| 4,430,243 A | 2/1984 | Bragg |
| 4,470,982 A | 9/1984 | Winkler |
| 4,973,416 A | 11/1990 | Kennedy |
| 4,985,238 A | 1/1991 | Tanner et al. |
| 5,019,375 A | 5/1991 | Tanner et al. |
| 5,104,646 A | 4/1992 | Bolich, Jr. et al. |
| 5,106,609 A | 4/1992 | Bolich, Jr. et al. |
| 5,296,622 A | 3/1994 | Uphues et al. |
| 5,429,816 A | 7/1995 | Hofrichter et al. |
| 5,486,303 A | 1/1996 | Capeci et al. |
| 5,489,392 A | 2/1996 | Capeci et al. |
| 5,516,448 A | 5/1996 | Capeci et al. |
| 5,565,422 A | 10/1996 | Del Greco et al. |
| 5,569,645 A | 10/1996 | Dinniwell et al. |
| 5,574,005 A | 11/1996 | Welch et al. |
| 5,576,282 A | 11/1996 | Miracle et al. |
| 5,595,967 A | 1/1997 | Miracle et al. |
| 5,597,936 A | 1/1997 | Perkins et al. |
| 5,691,297 A | 11/1997 | Nassano et al. |
| 5,714,137 A | 2/1998 | Trinh et al. |
| 5,800,897 A * | 9/1998 | Sharma ............... A61L 9/042 239/53 |
| 5,879,584 A | 3/1999 | Bianchetti et al. |
| 5,891,424 A | 4/1999 | Bretzler et al. |
| 5,942,217 A | 8/1999 | Woo et al. |
| 5,976,514 A | 11/1999 | Guskey et al. |
| 6,180,121 B1 | 1/2001 | Guenin et al. |
| 6,225,464 B1 | 5/2001 | Hiler, II et al. |
| 6,248,135 B1 | 6/2001 | Trinh et al. |
| 6,386,392 B1 | 5/2002 | Argentieri et al. |
| 6,413,920 B1 | 7/2002 | Bettiol et al. |
| 6,436,442 B1 | 8/2002 | Woo et al. |
| 6,488,943 B1 | 12/2002 | Beerse et al. |
| 6,656,923 B1 | 12/2003 | Trinh et al. |
| 6,716,805 B1 | 4/2004 | Sherry et al. |
| 6,814,088 B2 | 11/2004 | Barnabas et al. |
| 6,869,923 B1 | 3/2005 | Cunningham et al. |
| 7,100,767 B2 | 9/2006 | Chomik |
| 7,172,099 B2 | 2/2007 | Höfte et al. |
| 7,202,198 B2 | 4/2007 | Gordon et al. |
| 7,223,361 B2 | 5/2007 | Kvietok et al. |
| 8,058,500 B2 | 11/2011 | Sojka |
| 8,158,571 B2 | 4/2012 | Alonso |
| 8,322,631 B2 | 12/2012 | Richardson et al. |
| 8,609,600 B2 | 12/2013 | Warr |
| 8,709,337 B2 | 4/2014 | Gruenbacher et al. |
| 8,772,354 B2 | 7/2014 | Williams et al. |
| 8,931,711 B2 | 1/2015 | Gruenbacher et al. |
| 2003/0192922 A1 * | 10/2003 | Ceppaluni ............... A61L 9/14 222/642 |
| 2004/0064117 A1 | 4/2004 | Hammons et al. |
| 2004/0151793 A1 | 8/2004 | Paspaleeva-kuhn et al. |
| 2005/0003980 A1 | 1/2005 | Baker et al. |
| 2005/0192207 A1 | 9/2005 | Morgan |
| 2005/0276831 A1 | 12/2005 | Dihora et al. |
| 2006/0166857 A1 | 7/2006 | Surburg |
| 2007/0003499 A1 | 1/2007 | Shen et al. |
| 2007/0020263 A1 | 1/2007 | Shitara et al. |
| 2007/0275866 A1 | 11/2007 | Dykstra |
| 2008/0003245 A1 | 1/2008 | Kroepke et al. |
| 2008/0176780 A1 | 7/2008 | Warr |
| 2009/0005280 A1 | 1/2009 | Woo |
| 2009/0240223 A1 | 9/2009 | Warren et al. |
| 2009/0312223 A1 | 12/2009 | Yang |
| 2010/0001116 A1 | 1/2010 | Johnson |

(56) References Cited

U.S. PATENT DOCUMENTS

| | | |
|---|---|---|
| 2010/0009285 A1 | 1/2010 | Daems et al. |
| 2010/0061946 A1 | 3/2010 | Scherner et al. |
| 2010/0098209 A1 | 4/2010 | Forthmann et al. |
| 2010/0287710 A1 | 11/2010 | Denutte et al. |
| 2010/0322878 A1 | 12/2010 | Stella et al. |
| 2011/0098209 A1 | 4/2011 | Smets et al. |
| 2011/0245134 A1 | 10/2011 | Smets |
| 2011/0269657 A1 | 11/2011 | Dihora et al. |
| 2011/0303766 A1 | 12/2011 | Smith |
| 2011/0308555 A1 | 12/2011 | Smetts |
| 2012/0004328 A1 | 1/2012 | Huchel et al. |
| 2012/0009285 A1 | 1/2012 | Wei et al. |
| 2012/0129924 A1 | 5/2012 | Park et al. |
| 2012/0219610 A1 | 8/2012 | Smith, III et al. |
| 2012/0230936 A1* | 9/2012 | Mikkelsen ............... A61L 9/048 424/76.4 |
| 2012/0237469 A1 | 9/2012 | Dente et al. |
| 2012/0246851 A1 | 10/2012 | Smith, III et al. |
| 2012/0258150 A1 | 10/2012 | Rauckhorst et al. |
| 2013/0043145 A1 | 2/2013 | Smith, III et al. |
| 2013/0043146 A1 | 2/2013 | Smith, III et al. |
| 2013/0043147 A1 | 2/2013 | Smith, III et al. |
| 2013/0319463 A1 | 12/2013 | Policicchio |
| 2014/0201927 A1 | 7/2014 | Bianchetti et al. |
| 2015/0108163 A1 | 4/2015 | Smith et al. |
| 2016/0089317 A1 | 3/2016 | Cetti et al. |
| 2016/0089318 A1 | 3/2016 | Cetti et al. |
| 2016/0089462 A1 | 3/2016 | Frankenbach et al. |
| 2016/0089464 A1 | 3/2016 | Frankenbach et al. |
| 2016/0089465 A1 | 3/2016 | Frankenbach et al. |
| 2016/0090555 A1 | 3/2016 | Frankenbach et al. |
| 2016/0090556 A1 | 3/2016 | Frankenbach et al. |
| 2016/0090557 A1 | 3/2016 | Frankenbach et al. |
| 2016/0090558 A1 | 3/2016 | Frankenbach et al. |
| 2016/0092661 A1 | 3/2016 | Hollingshead et al. |
| 2016/0206522 A1 | 7/2016 | Ribaut |
| 2016/0296656 A1 | 10/2016 | Scavone et al. |
| 2016/0306909 A1 | 10/2016 | Hollingshead et al. |
| 2017/0066579 A1 | 3/2017 | Zillges |
| 2017/0119917 A1 | 5/2017 | Frankenbach et al. |
| 2017/0137752 A1 | 5/2017 | Frankenbach et al. |
| 2017/0137753 A1 | 5/2017 | Frankenbach et al. |

FOREIGN PATENT DOCUMENTS

| | | |
|---|---|---|
| DE | 10 2004 023720 A1 | 12/2005 |
| DE | 10 2007 019369 A1 | 10/2008 |
| EP | 2 005 939 A1 | 12/2008 |
| GB | 1347950 A | 2/1974 |
| GB | 2048229 A | 12/1980 |
| GB | 2144992 A | 3/1985 |
| GB | 2 450 727 A | 1/2009 |
| WO | WO 96/04937 A1 | 2/1996 |
| WO | WO 99/57233 A1 | 11/1999 |
| WO | WO 00/19822 A1 | 4/2000 |
| WO | WO 00/32601 A2 | 6/2000 |
| WO | WO2008100411 A1 | 8/2008 |
| WO | WO 2011/152886 A2 | 12/2011 |
| WO | WO 2012/039516 A1 | 3/2012 |
| WO | WO 2012/136651 A1 | 10/2012 |

OTHER PUBLICATIONS

Todd, C., et al., Volatile silicone fluids for cosmetic formulations, Cosmetics and Toiletries, Jan. 1976, pp. 29-32, vol. 91.
Crepaldi, E.L., et al., Chemical, Structural, and Thermal Properties of Zn(II)—Cr(III) Layered Double Hydroxides Intercalated with Sulfated and Sulfonated Surfactants, Journal of Colloid and Interface Science, 2002, pp. 429-442, vol. 248.
Morioka, H., et al., Effects of Zinc on the New Preparation Method of Hydroxy Double Salts, Inorganic Chemistry, 1999 pp. 4211-4216, vol. 38, No. 19.
Database WPI; Week 201459; Thomson scientific, London, GB; AN 2014-P66521; XP002752638.
International Search Report; International Application No. PCT/US2015/052088; dated Jan. 22, 2016; 16 pages.
International Search Report; International Application No. PCT/US2015/052090; dated Jan. 19, 2016; 13 pages.
International Search Report; International Application No. PCT/US2015/052092; dated Jan. 12, 2016; 13 pages.
International Search Report; International Application No. PCT/US2015/052219; dated Jan. 26, 2016; 13 pages.
International Search Report; International Application No. PCT/US2015/052093; dated Jan. 12, 2016; 13 pages.
International Search Report; International Application No. PCT/US2015/052094; dated Jan. 20, 2016; 11 pages.
International Search Report; International Application No. PCT/US2015/052119; dated Jan. 20, 2016; 13 pages.
International Search Report; International Application No. PCT/US2015/052225; dated Jan. 20, 2016; 16 pages.
International Search Report; International Application No. PCT/US2015/052130; dated Jan. 12, 2016; 13 pages.
International Search Report; International Application No. PCT/US2015/052084; dated Jan. 19, 2016; 13 pages.
International Search Report; International Application No. PCT/US2015/052089; dated Feb. 23, 2016; 11 pages.
U.S. Appl. No. 14/864,927, filed Sep. 25, 2015, Frankenbach, et al.
U.S. Appl. No. 14/865,056, filed Sep. 25, 2015, Scavone, et al.
U.S. Appl. No. 14/867,973, filed Sep. 25, 2015, Hollingshead, et al.
U.S. Appl. No. 14/864,994, filed Sep. 25, 2015, Frankenbach, et al.
U.S. Appl. No. 14/865,010, filed Sep. 25, 2015, Frankenbach, et al.
U.S. Appl. No. 14/865,048, filed Sep. 25, 2015, Cetti, et al.
U.S. Appl. No. 14/865,257, filed Sep. 25, 2015, Cetti, et al.
U.S. Appl. No. 14/865,089, filed Sep. 25, 2015, Frankenbach, et al.
U.S. Appl. No. 14/865,099, filed Sep. 25, 2015, Frankenbach, et al.
U.S. Appl. No. 14/865,412, filed Sep. 25, 2015, Frankenbach, et al.
McGinley et al. Performance Verification of Air Freshener Products and Other Odour Control Devices for Indoor Air Quality Malodours. Presented at the 8th Workshop on Odour and Emissions of Plastic Materials Universität Kassel Institut für Werkstofftechnik Kassel, Germany: Mar. 27-28, 2006. 13p.
U.S. Appl. No. 15/597,391, filed May 17, 2017, Cetti, et al.
U.S. Appl. No. 15/597,376, filed May 17, 2017, Cetti, et al.
U.S. Appl. No. 15/432,957, filed Feb. 15, 2017, Frankenbach, et al.
Air Quality Bureau of the Iowa Department of Natural Resources. A Review of the Science and Technology of Odor Measurement. 2005.51 pages. (Year: 2005).
Brattoli et al. Odour Detection Methods: Olfactometry and Chemical Sensors. Sensors (Basel). 2011; 11 (5): 5290-5322. (Year:2011); 29 Pages.
McGinleyet. al. American Association of Textile Chemists and Colorists. 2017. 17 pages. (Year: 2017).

* cited by examiner

FRESHENING COMPOSITIONS AND DEVICES COMPRISING SAME

FIELD OF THE INVENTION

The present invention relates to freshening compositions and devices comprising same that comprise a composition comprising malodor reduction compositions and methods of making and using such compositions.

BACKGROUND OF THE INVENTION

Unscented or scented products are desired by consumers as they may be considered more natural and discreet than scented products. Manufacturers of unscented or scented products for controlling malodors rely on malodor reduction ingredients or other technologies (e.g. filters) to reduce malodors. However, effectively controlling malodors, for example, amine-based malodors (e.g. fish and urine), thiol and sulfide-based malodors (e.g. garlic and onion), $C_2$-$C_{12}$ carboxylic acid based malodors (e.g. body and pet odor), indole based malodors (e.g. fecal and bad breath), short chain fatty aldehyde based malodors (e.g. grease) and geosmin based malodors (e.g. mold/mildew) may be difficult, and the time required for a product to noticeably reduce malodors may create consumer doubt as to the product's efficacy on malodors. Often times, manufacturers incorporate scented perfumes to help mask these difficult malodors.

Unfortunately, malodor control technologies typically cover up the malodor with a stronger scent and thus interfere with the scent of the perfumed or unperfumed situs that is treated with the malodor control technology. Thus, limited nature of the current malodor control technologies is extremely constraining. Thus what is needed is a broader palette of malodor control technologies so the perfume community can deliver the desired level of character in a greater number of situations/applications. Surprisingly, Applicants recognized that in addition to blocking a malodor's access to a sensory cell, in order to achieve the desired goal, a malodor control technology must leave such sensor cell open to other molecules, for example scent molecules. The freshening compositions and devices comprising same that contain the malodor control technologies disclosed herein provide such benefit as they do not unduely interfere with the scent of the perfumed or unperfumed situs that is treated with such freshening compositions.

SUMMARY OF THE INVENTION

The present invention relates to freshening compositions and devices comprising same that comprise a composition comprising malodor reduction compositions and methods of making and using such compositions. Such malodor control technologies do not unduely interfere with the scent of the perfumed or unperfumed situs that is treated with the malodor control technology.

DETAILED DESCRIPTION OF THE INVENTION

As used herein "MORV" is the calculated malodor reduction value for a subject material. A material's MORV indicates such material's ability to decrease or even eliminate the perception of one or more malodors. For purposes of the present application, a material's MORV is calculated in accordance with method found in the test methods section of the present application.

As used herein, the term "perfume" does not include malodor reduction materials. Thus, the perfume portion of a composition does not include, when determining the perfume's composition, any malodor reduction materials found in the composition as such malodor reduction materials are described herein. In short, if a material has a malodor reduction value "MORV" that is within the range of the MORV recited in the subject claim, such material is a malodor reduction material for purposes of such claim.

As used herein, "malodor" refers to compounds generally offensive or unpleasant to most people, such as the complex odors associated with bowel movements.

As used herein, "odor blocking" refers to the ability of a compound to dull the human sense of smell.

As used herein, the terms "a" and "an" mean "at least one".

As used herein, the terms "include", "includes" and "including" are meant to be non-limiting.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Malodor Reduction Materials

A non-limiting set of suitable malodor reduction materials are provided in the tables below. For ease of use, each material in Tables 1-3 is assigned a numerical indentifier which is found in the column for each table that is designated Number. Table 4 is a subset of Table 1, Table 5 is a subset of Table 2 and Table 6 is a subset of Table 3 and there for Tables 4, 5 and 6 each use the same numerical identifier as found, respectively, in Tables 1-3.

| Codes |
| --- |
| A = Vapor Pressure > 0.1 torr |
| B = Vapor Pressure is between 0.01 torr and 0.1 torr |
| C = LogP < 3 |
| D = LogP > 3 |
| E = Probability of Ingredient Color Instability = 0% |
| F = Probability of Ingredient Color Instability < 71% |
| G = Odor Detection Threshold less than p.ol = 8 |
| H = Odor Detection Threshold greater than p.ol = 8 |
| I = Melamine formaldehyde PMC Headspace Response Ratio greater than or equal to 10 |
| J = Melamine formaldehyde PMC leakage less than or equal to 5% |
| K = Log of liquid dish neat product liquid-air partition coefficient greater than or equal to −7 |
| L = Log of liquid dish neat product liquid-air partition coefficient greater than or equal to −5 |

TABLE 1

List of materials with at least one MORV from 1 to 5

| Number | Material Name | CAS Number | Comment Code |
|---|---|---|---|
| 1 | 2-ethylhexyl (Z)-3-(4-methoxyphenyl)acrylate | 5466-77-3 | DEFHJ |
| 2 | 2,4-dimethyl-2-(5,5,8,8-tetramethyl-5,6,7,8-tetrahydronaphthalen-2-yl)-1,3-dioxolane | 131812-67-4 | DFHJ |
| 3 | 1,1-dimethoxynon-2-yne | 13257-44-8 | ACEFHJK |
| 4 | para-Cymen-8-ol | 1197-01-9 | BCGIJK |
| 7 | 3-methoxy-7,7-dimethyl-10-methylenebicyclo[4.3.1]decane | 216970-21-7 | BDEFHJK |
| 9 | Methoxycyclododecane | 2986-54-1 | DEFHJK |
| 10 | 1,1-dimethoxycyclododecane | 950-33-4 | DEFHJK |
| 11 | (Z)-tridec-2-enenitrile | 22629-49-8 | DEFHJK |
| 13 | Oxybenzone | 131-57-7 | DEFGJ |
| 14 | Oxyoctaline formate | 65405-72-3 | DFHJK |
| 16 | 4-methyl-1-oxaspiro[5.5]undecan-4-ol | 57094-40-3 | CFGIJK |
| 17 | 7-methyl-2H-benzo[b][1,4]dioxepin-3(4H)-one | 28940-11-6 | CGIK |
| 18 | 1,8-dioxacycloheptadecan-9-one | 1725-01-5 | DGJ |
| 21 | 4-(tert-pentyl)cyclohexan-1-one | 16587-71-6 | ADFGIJKL |
| 22 | o-Phenyl anisol | 86-26-0 | DEFHJK |
| 23 | 3a,5,6,7,8,8b-hexahydro-2,2,6,6,7,8,8-heptamethyl-4H-indeno(4,5-d)-1,3-dioxole | 823178-41-2 | DEFHJK |
| 25 | 7-isopropyl-8,8-dimethyl-6,10-dioxaspiro[4.5]decane | 62406-73-9 | BDEFHIJK |
| 28 | Octyl 2-furoate | 39251-88-2 | DEFHJK |
| 29 | Octyl acetate | 112-14-1 | BDEFHJKL |
| 30 | octanal propylene glycol acetal | 74094-61-4 | BDEFHJKL |
| 31 | Octanal | 124-13-0 | ACHIKL |
| 32 | Octanal dimethyl acetal | 10022-28-3 | ACEFGJKL |
| 33 | Myrcene | 123-35-3 | ADEFGIKL |
| 34 | Myrcenol | 543-39-5 | BCEFGIJK |
| 35 | Myrcenyl acetate | 1118-39-4 | ADEFGJK |
| 36 | Myristaldehyde | 124-25-4 | DFHJK |
| 37 | Myristicine | 607-91-0 | CGJK |
| 38 | Myristyl nitrile | 629-63-0 | DEFHJK |
| 39 | 2,2,6,8-tetramethyl-1,2,3,4,4a,5,8,8a-octahydronaphthalen-1-ol | 103614-86-4 | DEFHIJK |
| 42 | Ocimenol | 5986-38-9 | BCHIJK |
| 43 | Ocimenol | 28977-58-4 | BCHIJK |
| 47 | Nopyl acetate | 128-51-8 | DEFHJK |
| 48 | Nootkatone | 4674-50-4 | DHJK |
| 49 | Nonyl alcohol | 143-08-8 | BDEFGIJKL |
| 50 | Nonaldehyde | 124-19-6 | ADHIKL |
| 52 | 12-methyl-14-tetradec-9-enolide | 223104-61-8 | DFHJK |
| 57 | N-ethyl-p-menthane-3-carboxamide | 39711-79-0 | DEFGIJK |
| 61 | 1-(3-methylbenzofuran-2-yl)ethan-1-one | 23911-56-0 | CEFHIK |
| 62 | 2-methoxynaphthalene | 93-04-9 | BDEFHK |
| 63 | Nerolidol | 7212-44-4 | DEFHJK |
| 64 | Nerol | 106-25-2 | BCHIK |
| 65 | 1-ethyl-3-methoxytricyclo[2.2.1.02,6]heptane | 31996-78-8 | ACEFHIJKL |
| 67 | Methyl (E)-non-2-enoate | 111-79-5 | ADEFHJKL |
| 68 | 10-isopropyl-2,7-dimethyl-1-oxaspiro[4.5]deca-3,6-diene | 89079-92-5 | BDEFHIJK |
| 69 | 2-(2-(4-methylcyclohex-3-en-1-yl)propyl)cyclopentan-1-one | 95962-14-4 | DHJK |
| 70 | Myrtenal | 564-94-3 | ACFHJKL |
| 71 | (E)-4-(2,2,3,6-tetramethylcyclohexyl)but-3-en-2-one | 54992-90-4 | BDEFHIJK |
| 74 | Myraldyl acetate | 53889-39-7 | DHJK |
| 75 | Musk tibetine | 145-39-1 | DHIJ |
| 76 | 1,7-dioxacycloheptadecan-8-one | 3391-83-1 | DGJ |
| 77 | Musk ketone | 81-14-1 | DHJ |
| 78 | Musk ambrette | 83-66-9 | DHIJ |
| 79 | 3-methylcyclopentadecan-1-one | 541-91-3 | DEFHJK |
| 80 | (E)-3-methylcyclopentadec-4-en-1-one | 82356-51-2 | DHJK |
| 82 | 3-methyl-4-phenylbutan-2-ol | 56836-93-2 | BCEFHIK |
| 83 | 1-(4-isopropylcyclohexyl)ethan-1-ol | 63767-86-2 | BDEFHIJK |
| 85 | Milk Lactone | 72881-27-7 | DEFHJK |
| 91 | Methyl octine carbonate | 111-80-8 | BDEFHKL |
| 92 | Methyl octyl acetaldehyde | 19009-56-4 | ADFHJKL |
| 93 | 6,6-dimethoxy-2,5,5-trimethylhex-2-ene | 67674-46-8 | ACHIJKL |
| 98 | Methyl phenylethyl carbinol | 2344-70-9 | BCEFHIK |
| 100 | Methyl stearate | 112-61-8 | DEFHJ |
| 101 | Methyl nonyl acetaldehyde dimethyl acetal | 68141-17-3 | BDEFHJK |
| 102 | Methyl nonyl ketone | 112-12-9 | BDFHJKL |
| 103 | Methyl nonyl acetaldehyde | 110-41-8 | BDFHJK |
| 104 | Methyl myristate | 124-10-7 | DEFHJK |
| 105 | Methyl linoleate | 112-63-0 | DEFHJ |
| 106 | Methyl lavender ketone | 67633-95-8 | CFHJK |
| 108 | Methyl isoeugenol | 93-16-3 | ACEFHK |
| 109 | Methyl hexadecanoate | 112-39-0 | DEFHJK |
| 110 | Methyl eugenol | 93-15-2 | ACEFHK |
| 112 | Methyl epijasmonate | 1211-29-6 | CHJK |
| 113 | Methyl dihydrojasmonate | 24851-98-7 | DFHJK |
| 114 | Methyl diphenyl ether | 3586-14-9 | DEFHJK |
| 117 | Methyl cinnamate | 103-26-4 | BCEFHK |
| 119 | Methyl chavicol | 140-67-0 | ADEFHK |
| 120 | Methyl beta-naphthyl ketone | 93-08-3 | CEFHK |
| 122 | Methyl 2-octynoate | 111-12-6 | ACEFHKL |
| 123 | Methyl alpha-cyclogeranate | 28043-10-9 | ACHIJKL |
| 126 | Methoxycitronellal | 3613-30-7 | ACFGIJK |
| 128 | Menthone 1,2-glycerol ketal (racemic) | 67785-70-0 | CEFHJ |
| 130 | Octahydro-1H-4,7-methanoindene-1-carbaldehyde | 30772-79-3 | BCFHIJKL |
| 134 | 3-(3-(tert-butyl)phenyl)-2-methylpropanal | 62518-65-4 | BDHJK |
| 135 | (E)-4-(4,8-dimethylnona-3,7-dien-1-yl)pyridine | 38462-23-6 | DEFHJK |
| 137 | (E)-trideca-3,12-dienenitrile | 134769-33-8 | DEFHJK |
| 140 | 2,2-dimethyl-3-(m-tolyl)propan-1-ol | 103694-68-4 | CEFHIJK |
| 141 | 2,4-dimethyl-4,4a,5,9b-tetrahydroindeno[1,2-d][1,3]dioxine | 27606-09-3 | CEFHJK |
| 142 | Maceal | 67845-30-1 | BDFHJK |
| 143 | 4-(4-hydroxy-4-methylpentyl)cyclohex-3-ene-1-carbaldehyde | 31906-04-4 | CHJ |
| 145 | l-Limonene | 5989-54-8 | ADEFGIJKL |
| 146 | (Z)-3-hexen-1-yl-2-cyclopenten-1-one | 53253-09-1 | BDHK |
| 148 | Linalyl octanoate | 10024-64-3 | DEFHJ |
| 149 | Linalyl isobutyrate | 78-35-3 | BDHJK |
| 152 | Linalyl benzoate | 126-64-7 | DFHJ |
| 153 | Linalyl anthranilate | 7149-26-0 | DFHJ |
| 155 | Linalool oxide (furanoid) | 60047-17-8 | BCHIJK |
| 156 | linalool oxide | 1365-19-1 | CGIJK |
| 158 | (2Z,6E)-3,7-dimethylnona-2,6-dienenitrile | 61792-11-8 | BDEFHJK |
| 159 | 3-(4-methylcyclohex-3-en-1-yl)butanal | 6784-13-0 | ACFHIJK |
| 161 | (2,5-dimethyl-1,3-dihydroinden-2-yl)methanol | 285977-85-7 | CEFHJK |
| 162 | 3-(4-(tert-butyl)phenyl)-2-methylpropanal | 80-54-6 | BDHJK |
| 167 | (E)-1-(1-methoxypropoxy)hex-3-ene | 97358-54-8 | ACEFGJKL |
| 168 | Leaf acetal | 88683-94-7 | ACEFGJKL |
| 170 | l-Carveol | 2102-58-1 | BCHIJK |
| 174 | Lauryl alcohol | 112-53-8 | DEFGJK |
| 175 | Lauryl acetate | 112-66-3 | DEFHJK |
| 176 | Lauric acid | 143-07-7 | DEFHJ |
| 177 | Lactojasmone | 7011-83-8 | BDEFHIJKL |
| 178 | Lauraldehyde | 112-54-9 | BDFHJK |
| 179 | 3,6-dimethylhexahydrobenzofuran-2(3H)-one | 92015-65-1 | BCEFHIJKL |
| 182 | 4-(1-ethoxyvinyl)-3,3,5,5-tetramethylcyclohexan-1-one | 36306-87-3 | BDFHIJK |
| 183 | Khusimol | 16223-63-5 | CEFHJK |
| 184 | 5-(sec-butyl)-2-(2,4-dimethylcyclohex-3-en-1-yl)-5-methyl-1,3-dioxane | 117933-89-8 | DEFHJ |

TABLE 1-continued

List of materials with at least one MORV from 1 to 5

| Number | Material Name | CAS Number | Comment Code |
|---|---|---|---|
| 185 | (1-methyl-2-((1,2,2-trimethylbicyclo[3.1.0]hexan-3-yl)methyl)cyclopropyl)methanol | 198404-98-7 | DEFHJK |
| 186 | 2-propylheptanenitrile | 208041-98-9 | ADEFHIJKL |
| 187 | (E)-6-(pent-3-en-1-yl)tetrahydro-2H-pyran-2-one | 32764-98-0 | BCFHIKL |
| 189 | 2-hexylcyclopentan-1-one | 13074-65-2 | BDFHJKL |
| 190 | 2-methyl-4-phenyl-1,3-dioxolane | 33941-99-0 | BCEFGIK |
| 192 | 2,6,9,10-tetramethyl-1-oxaspiro(4.5)deca-3,6-diene | 71078-31-4 | BDEFHIJK |
| 193 | Isopulegol | 89-79-2 | BCEFHIJKL |
| 195 | Isopropyl palmitate | 142-91-6 | DEFHJ |
| 196 | Isopropyl myristate | 110-27-0 | DEFHJK |
| 197 | Isopropyl dodecanoate | 10233-13-3 | DEFHJK |
| 199 | Isopimpinellin | 482-27-9 | CFGJ |
| 206 | Iso3-methylcyclopentadecan-1-one | 3100-36-5 | DEFGJK |
| 208 | Isomenthone | 491-07-6 | ADEFGIJKL |
| 209 | Isojasmone | 95-41-0 | BDFHJKL |
| 210 | Isomenthone | 36977-92-1 | ADEFGIJKL |
| 211 | Isohexenyl cyclohexenyl carboxaldehyde | 37677-14-8 | DFHJK |
| 212 | Isoeugenyl benzyl ether | 120-11-6 | DFHJ |
| 215 | 1-((2S,3S)-2,3,8,8-tetramethyl-1,2,3,4,5,6,7,8-octahydronaphthalen-2-yl)ethan-1-one | 54464-57-2 | DHJK |
| 218 | Isocyclocitral | 1335-66-6 | ACFHJKL |
| 221 | Isobutyl quinoline | 65442-31-1 | DEFHJK |
| 227 | Isobornylcyclohexanol | 68877-29-2 | DEFHJ |
| 228 | Isobornyl propionate | 2756-56-1 | BDEFHIJK |
| 229 | Isobornyl isobutyrate | 85586-67-0 | BDEFHIJK |
| 230 | Isobornyl cyclohexanol | 66072-32-0 | DEFHJK |
| 231 | Isobornyl acetate | 125-12-2 | ADEFHIJKL |
| 233 | Isobergamate | 68683-20-5 | DEFHJK |
| 234 | Isoamyl undecylenate | 12262-03-2 | DEFHJK |
| 238 | Isoamyl laurate | 6309-51-9 | DEFHJK |
| 242 | Isoambrettolide | 28645-51-4 | DGJ |
| 243 | Irisnitrile | 29127-83-1 | ADEFHKL |
| 244 | Indolene | 68527-79-7 | DEFHJ |
| 246 | Indol/Hydroxycitronellal Schiff base | 67801-36-9 | DEFHJ |
| 247 | 4,4a,5,9b-tetrahydroindeno[1,2-d][1,3]dioxine | 18096-62-3 | BCEFGJK |
| 249 | Hydroxy-citronellol | 107-74-4 | CEFGIJK |
| 252 | 2-cyclododecylpropan-1-ol | 118562-73-5 | DEFHJK |
| 253 | Hydrocitronitrile | 54089-83-7 | CEFHJK |
| 254 | Hydrocinnamyl alcohol | 122-97-4 | BCEFHJK |
| 256 | Hydratropaldehyde dimethyl acetal | 90-87-9 | ACEFHJK |
| 259 | 5-ethyl-4-hydroxy-2-methylfuran-3(2H)-one | 27538-09-6 | CFGIK |
| 260 | 2,3-dihydro-3,3-dimethyl-1H-indene-5-propanal | 173445-44-8 | DHJK |
| 261 | 3-(3,3-dimethyl-2,3-dihydro-1H-inden-5-yl)propanal | 173445-65-3 | DHJK |
| 263 | Hexyl octanoate | 1117-55-1 | DEFHJK |
| 267 | Hexyl hexanoate | 6378-65-0 | DEFHJKL |
| 269 | Hexyl cinnamic aldehyde | 101-86-0 | DHJ |
| 271 | Hexyl benzoate | 6789-88-4 | DEFHJK |
| 274 | Hexenyl tiglate | 84060-80-0 | BDEFHJK |
| 276 | (E)-3,7-dimethylocta-2,6-dien-1-yl palmitate | 3681-73-0 | DEFHJ |
| 277 | Hexadecanolide | 109-29-5 | DEFGJK |
| 278 | 2-butyl-4,4,6-trimethyl-1,3-dioxane | 54546-26-8 | ADEFHIJKL |
| 280 | Ethyl (1R,2R,3R,4R)-3-isopropylbicyclo[2.2.1]hept-5-ene-2-carboxylate | 116126-82-0 | BDEFHIJK |
| 281 | 3a,4,5,6,7,7a-hexahydro-1H-4,7-methanoinden-6-yl acetate | 5413-60-5 | CEFGJK |
| 285 | 2-(1-(3,3-dimethylcyclohexyl)ethoxy)-2-methylpropyl propionate | 141773-73-1 | DEFHJ |
| 286 | Heliotropine diethyl acetal | 40527-42-2 | CEFGJ |
| 288 | Helional | 1205-17-0 | CHJK |
| 289 | (E)-oxacyclohexadec-13-en-2-one | 111879-80-2 | DGJK |
| 290 | Gyrane | 24237-00-1 | ADEFHIJKL |
| 292 | Guaiol | 489-86-1 | DEFHJK |
| 293 | 1-(2,6,6-trimethylcyclohex-2-en-1-yl)pentan-3-one | 68611-23-4 | DHJK |
| 294 | Ethyl 2-ethyl-6,6-dimethylcyclohex-2-ene-1-carboxylate | 57934-97-1 | BDEFHIJK |
| 295 | Germacrene B | 15423-57-1 | DEFHJK |
| 296 | Germacrene D | 23986-74-5 | DEFHJK |
| 300 | Geranyl phenylacetate | 102-22-7 | DFHJ |
| 301 | Geranyl phenyl acetate | 71648-43-6 | DFHJ |
| 303 | Geranyl linalool | 1113-21-9 | DFHJ |
| 307 | Geranyl cyclopentanone | 68133-79-9 | DHJK |
| 316 | gamma-Undecalactone (racemic) | 104-67-6 | DEFHJKL |
| 317 | gamma-Terpinyl acetate | 10235-63-9 | BDHJK |
| 318 | gamma-Terpineol | 586-81-2 | BCGIJK |
| 321 | gamma-Nonalactone | 104-61-0 | BCEFHIKL |
| 322 | gamma-Muurolene | 30021-74-0 | DEFHJKL |
| 323 | gamma-(E)-6-(pent-3-en-1-yl)tetrahydro-2H-pyran-2-one | 63095-33-0 | BCEFHKL |
| 324 | gamma-Ionone | 79-76-5 | BDEFHIJK |
| 325 | gamma-Himachalene | 53111-25-4 | BDEFHJKL |
| 328 | gamma-Gurjunene | 22567-17-5 | DEFHJKL |
| 329 | gamma-Eudesmol | 1209-71-8 | DFHJK |
| 330 | gamma-Dodecalactone | 2305-05-7 | DEFHJK |
| 331 | gamma-Damascone | 35087-49-1 | BDEFHIJK |
| 332 | gamma-Decalactone | 706-14-9 | BDEFHIJK |
| 333 | gamma-Cadinene | 39029-41-9 | DEFHJKL |
| 334 | 1-(3,3-dimethylcyclohexyl)pent-4-en-1-one | 56973-87-6 | BDEFHJK |
| 335 | 4,6,6,7,8,8-hexamethyl-1,3,4,6,7,8-hexahydrocyclopenta[g]isochromene | 1222-05-5 | DEFHJK |
| 336 | Furfuryl octanoate | 39252-03-4 | DEFHJK |
| 338 | Furfuryl hexanoate | 39252-02-3 | CEFHJK |
| 339 | Furfuryl heptanoate | 39481-28-2 | CEFHJK |
| 342 | 2-methyldecanenitrile | 69300-15-8 | BDEFHJKL |
| 343 | 8,8-dimethyl-3a,4,5,6,7,7a-hexahydro-1H-4,7-methanoinden-6-yl propionate | 76842-49-4 | DEFHJK |
| 344 | Ethyl (3aR,4S,7R,7aR)-octahydro-3aH-4,7-methanoindene-3a-carboxylate | 80657-64-3 | DEFHIJK |
| 347 | Diethyl cyclohexane-1,4-dicarboxylate | 72903-27-6 | CEFHJK |
| 349 | (6-isopropyl-9-methyl-1,4-dioxaspiro[4.5]decan-2-yl)methanol | 63187-91-7 | CEFHJ |
| 350 | 2-isobutyl-4-methyltetrahydro-2H-pyran-4-ol | 63500-71-0 | BCEFHIJK |
| 352 | Undec-10-enenitrile | 53179-04-7 | BDEFHIJK |
| 353 | (Z)-6-ethylideneoctahydro-2H-5,8-methanochromen-2-one | 69486-14-2 | CEFGJK |
| 356 | 3-(2-ethylphenyl)-2,2-dimethylpropanal | 67634-15-5 | BDHJK |
| 358 | (E)-4,8-dimethyldeca-4,9-dienal | 71077-31-1 | BDFHJK |
| 359 | (E)-4-((3aR,4R,7R,7aR)-1,3a,4,6,7,7a-hexahydro-5H-4,7-methanoinden-5-ylidene)-3-methylbutan-2-ol | 501929-47-1 | DEFHJK |
| 360 | 8,8-dimethyl-3a,4,5,6,7,7a-hexahydro-1H-4,7-methanoinden-6-yl acetate | 171102-41-3 | DEFHJK |
| 361 | 3-(4-ethylphenyl)-2,2-dimethylpropanenitrile | 134123-93-6 | DEFHJK |
| 362 | 2-heptylcyclopentan-1-one | 137-03-1 | DFHJKL |
| 363 | 1-ethoxyethoxy Cyclododecane | 389083-83-4 | DEFHJK |
| 364 | 3-cyclohexene-1-carboxylic acid, 2,6,6-trimethyl-, methyl ester | 815580-59-7 | ACHIJKL |
| 368 | Farnesyl acetate | 29548-30-9 | DEFHJK |
| 369 | Farnesol | 4602-84-0 | DEFHJK |
| 370 | Oxacyclohexadecan-2-one | 106-02-5 | DEFGJK |
| 371 | 1-cyclopentadec-4-en-1-one | 14595-54-1 | DEFGJK |
| 372 | 1-cyclopentadec-4-en-1-one | 35720-57-1 | DEFGJK |
| 373 | 2-methoxy-4-(4-methylenetetrahydro-2H-pyran-2-yl)phenol | 128489-04-3 | CGJ |
| 374 | Eugenyl acetate | 93-28-7 | CFHJK |
| 375 | Eugenol | 97-53-0 | CHIK |
| 377 | Ethylmethylphenylglycidate | 77-83-8 | CFHJK |

TABLE 1-continued

List of materials with at least one MORV from 1 to 5

| Number | Material Name | CAS Number | Comment Code |
|---|---|---|---|
| 378 | Ethylene brassylate | 105-95-3 | DFGJ |
| 381 | Ethyl undecylenate | 692-86-4 | DEFHJK |
| 385 | Ethyl palmitate | 628-97-7 | DEFHJ |
| 386 | Ethyl nonanoate | 123-29-5 | BDEFHJKL |
| 388 | Ethyl myristate | 124-06-1 | DEFHJK |
| 390 | Ethyl linalool | 10339-55-6 | BCEFHJK |
| 391 | Ethyl laurate | 106-33-2 | DEFHJK |
| 394 | Ethyl hexyl ketone | 925-78-0 | ADFHIKL |
| 397 | Ethyl decanoate | 110-38-3 | BDEFHJK |
| 398 | Ethyl gamma-Safranate | 35044-57-6 | ADHIJK |
| 407 | Ethyl 3-phenylglycidate | 121-39-1 | CGJK |
| 413 | 6-ethyl-2,10,10-trimethyl-1-oxaspiro[4.5]deca-3,6-diene | 79893-63-3 | BDEFHIJK |
| 414 | Elemol | 639-99-6 | DEFHJK |
| 415 | (2-(1-ethoxyethoxy)ethyl)benzene | 2556-10-7 | BCEFHJK |
| 416 | (E)-3-methyl-5-(2,2,3-trimethylcyclopent-3-en-1-yl)pent-4-en-2-ol | 67801-20-1 | DHJK |
| 417 | d-xylose | 58-86-6 | CGIJ |
| 418 | (E)-4-((3aS,7aS)-octahydro-5H-4,7-methanoinden-5-ylidene)butanal | 30168-23-1 | DFHJK |
| 421 | Dodecanal dimethyl acetal | 14620-52-1 | DEFHJK |
| 424 | d-Limonene | 5989-27-5 | ADEFGIJKL |
| 425 | Dipropylene Glycol | 25265-71-8 | CEFGJK |
| 426 | Dispirone | 83863-64-3 | BDEFHJK |
| 428 | Diphenyloxide | 101-84-8 | BDEFHK |
| 429 | Diphenylmethane | 101-81-5 | DEFGK |
| 432 | Dimethyl benzyl carbinyl butyrate | 10094-34-5 | DEFHJK |
| 436 | 2,6-dimethyloct-7-en-4-one | 1879-00-1 | ADEFHIJKL |
| 441 | Octahydro-1H-4,7-methanoinden-5-yl acetate | 64001-15-6 | DEFHJKL |
| 444 | Dihydrocarveol acetate | 20777-49-5 | BDEFHIJK |
| 445 | Dihydrocarveol | 619-01-2 | BCEFHIJKL |
| 449 | Dihydro Linalool | 18479-51-1 | BCEFGIJKL |
| 450 | Dihydro Isojasmonate | 37172-53-5 | DHJK |
| 453 | Dibutyl sulfide | 544-40-1 | ADEFHIKL |
| 457 | Dibenzyl | 103-29-7 | DEFGK |
| 459 | delta-Undecalactone | 710-04-3 | DEFHJKL |
| 461 | delta-Elemene | 20307-84-0 | BDEFHJK |
| 462 | delta-Guaiene | 3691-11-0 | DEFHJKL |
| 463 | delta-Dodecalactone | 713-95-1 | DEFHJK |
| 464 | delta-Decalactone | 705-86-2 | BDEFHIJKL |
| 465 | delta-Cadinene | 483-76-1 | DEFHJKL |
| 466 | delta-damascone | 57378-68-4 | ADHIJK |
| 467 | delta-Amorphene | 189165-79-5 | DEFHJKL |
| 468 | delta-3-Carene | 13466-78-9 | ADEFGIJKL |
| 470 | Decylenic alcohol | 13019-22-2 | BDEFHJK |
| 471 | Decyl propionate | 5454-19-3 | DEFHJK |
| 473 | Decanal diethyl acetal | 34764-02-8 | DEFHJK |
| 474 | Decahydro-beta-naphthol | 825-51-4 | BCEFGIK |
| 475 | 1-cyclohexylethyl (E)-but-2-enoate | 68039-69-0 | BDFHJK |
| 478 | 3-(4-isopropylphenyl)-2-methylpropanal | 103-95-7 | BDFHJK |
| 479 | Cyclotetradecane | 295-17-0 | DEFGJKL |
| 480 | Cyclopentadecanone | 502-72-7 | DEFGJK |
| 482 | Cyclohexyl salicylate | 25485-88-5 | DFGJ |
| 484 | 3a,4,5,6,7,7a-hexahydro-1H-4,7-methanoinden-6-yl butyrate | 113889-23-9 | DEFHJK |
| 485 | Cyclic ethylene dodecanedioate | 54982-83-1 | DFGJ |
| 486 | 8,8-dimethyl-1,2,3,4,5,6,7,8-octahydronaphthalene-2-carbaldehyde | 68991-97-9 | DHJK |
| 487 | 3a,4,5,6,7,7a-hexahydro-1H-4,7-methanoinden-5-yl isobutyrate | 67634-20-2 | DEFHJK |
| 488 | Curzerene | 17910-09-7 | DHJK |
| 491 | Cumic alcohol | 536-60-7 | CHIJK |
| 493 | Coumarone | 1646-26-0 | BCEFHIK |
| 497 | 2-(3-phenylpropyl)pyridine | 2110-18-1 | CEFHJK |
| 498 | Dodecanenitrile | 2437-25-4 | DEFHJK |
| 501 | (E)-cycloheptadec-9-en-1-one | 542-46-1 | DEFGJ |
| 502 | Citryl acetate | 6819-19-8 | DFHJK |
| 503 | Citrus Propanol | 15760-18-6 | CEFHIJK |
| 505 | Citronitrile | 93893-89-1 | CEFHJK |
| 519 | Citral propylene glycol acetal | 10444-50-5 | CEFHJK |
| 520 | Citral dimethyl acetal | 7549-37-3 | BCEFHJK |
| 521 | Citral diethyl acetal | 7492-66-2 | BDEFHJK |
| 524 | cis-Ocimene | 3338-55-4 | ADGIKL |
| 527 | cis-Limonene oxide | 13837-75-7 | ADEFGIJKL |
| 529 | Cis-iso-ambrettolide | 36508-31-3 | DGJ |
| 530 | cis-6-nonenol | 35854-86-5 | BCEFHIKL |
| 531 | cis-carveol | 1197-06-4 | BCHIJK |
| 532 | cis-4-Decen-1-al | 21662-09-9 | ADHKL |
| 534 | cis-3-hexenyl-cis-3-hexenoate | 61444-38-0 | BDEFHJK |
| 537 | cis-3-Hexenyl salicylate | 65405-77-8 | DEFGJ |
| 541 | Cis-3-hexenyl Benzoate | 25152-85-6 | DEFHJK |
| 544 | cis-3-Hexenyl 2-methylbutyrate | 53398-85-9 | ADEFHJKL |
| 546 | cis-3, cis-6-nonadienol | 53046-97-2 | ACEFHK |
| 548 | Cinnamyl propionate | 103-56-0 | DEFHJK |
| 550 | Cinnamyl isobutyrate | 103-59-3 | DEFHJK |
| 551 | Cinnamyl formate | 104-65-4 | BCEFHK |
| 552 | Cinnamyl cinnamate | 122-69-0 | DHJ |
| 553 | Cinnamyl acetate | 103-54-8 | BCEFHK |
| 555 | Cinnamic alcohol | 104-54-1 | BCEFHIK |
| 558 | Cetyl alcohol | 36653-82-4 | DEFHJ |
| 559 | (E)-1-(2,6,6-trimethylcyclohex-2-en-1-yl)hepta-1,6-dien-3-one | 79-78-7 | DHJK |
| 560 | 2-methyl-4-(2,6,6-trimethylcyclohex-1-en-1-yl)butanal | 65405-84-7 | DFHJK |
| 561 | (3aR,5aR,9aR,9bR)-3a,6,6,9a-tetramethyldodecahydronaphtho[2,1-b]furan | 3738-00-9 | DEFHJK |
| 562 | 1,6-dioxacycloheptadecan-7-one | 6707-60-4 | DGJ |
| 563 | 1-(6-(tert-butyl)-1,1-dimethyl-2,3-dihydro-1H-inden-4-yl)ethan-1-one | 13171-00-1 | DEFHJK |
| 565 | Cedryl methyl ether | 19870-74-7 | ADEFHJK |
| 566 | Cedryl formate | 39900-38-4 | BDEFHJK |
| 567 | Cedryl acetate | 77-54-3 | DEFHJK |
| 568 | (4Z,8Z)-1,5,9-trimethyl-13-oxabicyclo[10.1.0]trideca-4,8-diene | 71735-79-0 | DFHJK |
| 569 | Cedrol | 77-53-2 | DEFHJK |
| 570 | 5-methyl-1-(2,2,3-trimethylcyclopent-3-en-1-yl)-6-oxabicyclo[3.2.1]octane | 139539-66-5 | DEFHJK |
| 571 | 5-methyl-1-(2,2,3-trimethylcyclopent-3-en-1-yl)-6-oxabicyclo[3.2.1]octane | 426218-78-2 | DFHJ |
| 572 | 1,1,2,3,3-pentamethyl-1,2,3,5,6,7-hexahydro-4H-inden-4-one | 33704-61-9 | BDEFHIJK |
| 573 | Caryophyllene alcohol acetate | 32214-91-8 | DEFHJK |
| 574 | Caryolan-1-ol | 472-97-9 | DEFHJK |
| 577 | Carvyl acetate | 97-42-7 | BDHIJK |
| 578 | Caprylnitrile | 124-12-9 | ACEFGIKL |
| 580 | Caprylic alcohol | 111-87-5 | ACEFGIKL |
| 581 | Caprylic acid | 124-07-2 | BCEFHIK |
| 582 | Capric acid | 334-48-5 | DEFHJK |
| 584 | Capraldehyde | 112-31-2 | ADHKL |
| 586 | 3-(4-methoxyphenyl)-2-methylpropanal | 5462-06-6 | BCHJK |
| 587 | Camphorquinone | 10373-78-1 | ACEFGIJK |
| 589 | Camphene | 79-92-5 | ADEFGIJKL |
| 591 | Ethyl 2-methyl-4-oxo-6-pentylcyclohex-2-ene-1-carboxylate | 59151-19-8 | DHJ |
| 592 | Butylated hydroxytoluene | 128-37-0 | DEFGIJK |
| 594 | Butyl stearate | 123-95-5 | DEFHJ |
| 595 | Butyl butyryl lactate | 7492-70-8 | CEFGJK |
| 599 | Butyl 10-undecenoate | 109-42-2 | DEFHJK |
| 600 | 2-methyl-4-(2,2,3-trimethylcyclopent-3-en-1-yl)butan-1-ol | 72089-08-8 | DEFHJK |
| 601 | 3-(4-(tert-butyl)phenyl)propanal | 18127-01-0 | BDHJK |
| 603 | Bornyl isobutyrate | 24717-86-0 | BDEFHIJK |
| 604 | Bornyl acetate | 76-49-3 | ADEFHIJKL |
| 606 | 2-ethoxy-2,6,6-trimethyl-9-methylenebicyclo[3.3.1]nonane | 68845-00-1 | BDEFHJK |
| 607 | (ethoxymethoxy)cyclododecane | 58567-11-6 | DEFHJK |
| 608 | Bisabolene | 495-62-5 | DEFHJK |
| 609 | Bigarade oxide | 72429-08-4 | ADEFHJKL |
| 610 | beta-Vetivone | 18444-79-6 | DHJK |
| 611 | beta-Terpinyl acetate | 10198-23-9 | BDHJK |
| 612 | beta-Terpineol | 138-87-4 | BCGIJK |

TABLE 1-continued

List of materials with at least one MORV from 1 to 5

| Number | Material Name | CAS Number | Comment Code |
|---|---|---|---|
| 613 | beta-Sinensal | 60066-88-8 | DHJK |
| 614 | beta-Sesquiphellandrene | 20307-83-9 | DEFHJK |
| 615 | beta-Selinene | 17066-67-0 | BDEFGJK |
| 616 | beta-Santalol | 77-42-9 | DEFHJK |
| 618 | beta-Pinene | 127-91-3 | ADEFGIJKL |
| 620 | beta-Naphthyl ethyl ether | 93-18-5 | BDEFHJK |
| 621 | beta-Patchoulline | 514-51-2 | BDEFGJKL |
| 624 | beta-Himachalene Oxide | 57819-73-5 | BDFHJK |
| 625 | beta-Himachalene | 1461-03-6 | DEFHJKL |
| 626 | beta-Guaiene | 88-84-6 | DEFHJKL |
| 627 | (2,2-dimethoxyethyl)benzene | 101-48-4 | DHJK |
| 628 | beta-Farnesene | 18794-84-8 | DEFHJK |
| 631 | beta-Copaene | 18252-44-3 | BDEFHJKL |
| 632 | beta-Cedrene | 546-28-1 | BDEFGJKL |
| 633 | beta-Caryophyllene | 87-44-5 | DEFHJKL |
| 635 | beta-Bisabolol | 15352-77-9 | DFHJK |
| 636 | Beta ionone epoxide | 23267-57-4 | BDEFHIJK |
| 638 | Bergaptene | 484-20-8 | CGJ |
| 639 | Benzyl-tert-butanol | 103-05-9 | CEFGJK |
| 644 | Benzyl laurate | 140-25-0 | DEFHJ |
| 649 | Benzyl dimethyl carbinol | 100-86-7 | BCEFGIK |
| 650 | Benzyl cinnamate | 103-41-3 | DHJ |
| 653 | Benzyl benzoate | 120-51-4 | DHJ |
| 655 | Benzophenone | 119-61-9 | DEFHK |
| 658 | 7-isopentyl-2H-benzo[b][1,4]dioxepin-3(4H)-one | 362467-67-2 | DHJ |
| 659 | 2'-isopropyl-1,7,7-trimethylspiro[bicyclo[2.2.1]heptane-2,4'-[1,3]dioxane] | 188199-50-0 | DEFHJK |
| 660 | 4-(4-methylpent-3-en-1-yl)cyclohex-3-ene-1-carbonitrile | 21690-43-7 | DEFHJK |
| 661 | Aurantiol | 89-43-0 | DEFHJ |
| 663 | Anisyl phenylacetate | 102-17-0 | DFHJ |
| 668 | Methyl (E)-octa-4,7-dienoate | 189440-77-5 | ACEFHKL |
| 671 | Amyl Cinnamate | 3487-99-8 | DEFHJK |
| 673 | (3aR,5aS,9aS,9bR)-3a,6,6,9a-tetramethyldodecahydronaphtho[2,1-b]furan | 6790-58-5 | DEFHJK |
| 674 | (4aR,5R,7aS,9R)-2,2,5,8,8,9a-hexamethyloctahydro-4H-4a,9-methanoazuleno[5,6-d][1,3]dioxole | 211299-54-6 | DEFHJK |
| 675 | 2,5,5-trimethyl-1,2,3,4,5,6,7,8-octahydronaphthalen-2-ol | 71832-76-3 | DEFHJK |
| 676 | 2,5,5-trimethyl-1,2,3,4,5,6,7,8-octahydronaphthalen-2-ol | 41199-19-3 | DEFHJK |
| 677 | 1-((2-(tert-butyl)cyclohexyl)oxy)butan-2-ol | 139504-68-0 | DEFHJK |
| 678 | (3S,5aR,7aS,11aS,11bR)-3,8,8,11a-tetramethyldodecahydro-5H-3,5a-epoxynaphtho[2,1-c]oxepine | 57345-19-4 | DEFHJ |
| 679 | 2,2,6,6,7,8,8-heptamethyldecahydro-2H-indeno[4,5-b]furan | 476332-65-7 | ADEFHJK |
| 680 | 2,2,6,6,7,8,8-heptamethyldecahydro-2H-indeno[4,5-b]furan | 647828-16-8 | ADEFHJK |
| 681 | Amber acetate | 37172-02-4 | BDEFHJK |
| 682 | Alpinofix ® | 811436-82-5 | DEFHJ |
| 683 | alpha-Thujone | 546-80-5 | ADEFGIJKL |
| 684 | alpha-Vetivone | 15764-04-2 | DHJK |
| 686 | alpha-Terpinyl propionate | 80-27-3 | BDEFHJK |
| 691 | alpha-Sinensal | 17909-77-2 | DHJK |
| 692 | alpha-Selinene | 473-13-2 | BDEFHJK |
| 693 | alpha-Santalene | 512-61-8 | ADEFHJKL |
| 694 | alpha-Santalol | 115-71-9 | DEFHJK |
| 696 | alpha-Patchoulene | 560-32-7 | ADEFHJKL |
| 697 | alpha-neobutenone | 56973-85-4 | BDHJK |
| 698 | alpha-Muurolene | 10208-80-7 | DEFHJKL |
| 700 | alpha-methyl ionone | 127-42-4 | BDHJK |
| 702 | alpha-Limonene | 138-86-3 | ADEFGIJKL |
| 704 | alpha-Irone | 79-69-6 | BDHJK |
| 706 | alpha-Humulene | 6753-98-6 | BDEFHJK |
| 707 | alpha-Himachalene | 186538-22-7 | BDEFHJK |
| 708 | alpha-Gurjunene | 489-40-7 | BDEFHJKL |
| 709 | alpha-Guaiene | 3691-12-1 | DEFHJKL |
| 710 | alpha-Farnesene | 502-61-4 | DEFHJK |
| 711 | alpha-Fenchene | 471-84-1 | ADEFGIJKL |
| 712 | alpha-Eudesmol | 473-16-5 | DEFHJK |
| 713 | alpha-Curcumene | 4176-17-4 | DEFHJK |
| 714 | alpha-Cubebene | 17699-14-8 | ADEFHJKL |
| 715 | alpha-Cedrene epoxide | 13567-39-0 | ADEFHJK |
| 716 | alpha-Cadinol | 481-34-5 | DEFHJK |
| 717 | alpha-Cadinene | 24406-05-1 | DEFHJKL |
| 718 | alpha-Bisabolol | 515-69-5 | DFHJK |
| 719 | alpha-bisabolene | 17627-44-0 | DEFHJK |
| 720 | alpha-Bergamotene | 17699-05-7 | BDEFHJKL |
| 721 | alpha-Amylcinnamyl alcohol | 101-85-9 | DEFHJ |
| 722 | alpha-Amylcinnamyl acetate | 7493-78-9 | DEFHJ |
| 723 | alpha-Amylcinnamaldehyde diethyl acetal | 60763-41-9 | DEFHJ |
| 724 | alpha-Amylcinnamaldehyde | 122-40-7 | DHJK |
| 725 | alpha-Amorphene | 23515-88-0 | DEFHJKL |
| 726 | alpha-Agarofuran | 5956-12-7 | BDEFHJK |
| 727 | 1-methyl-4-(4-methyl-3-penten-1-yl)-3-Cyclohexene-1-carboxaldehyde | 52475-86-2 | DFHJK |
| 730 | 1-Phenyl-2-pentanol | 705-73-7 | CEFHK |
| 731 | 1-Phenyl-4-methyl-3-pentanol | 10415-87-9 | CEFHJK |
| 733 | 2,3,4-trimethoxy-benzaldehyde | 2103-57-3 | BCGI |
| 735 | 2,4,5-trimethoxy-benzaldehyde | 4460-86-0 | BCG |
| 736 | 2,4,6-trimethoxybenzaldehyde | 830-79-5 | BCGI |
| 738 | 2,4-Nonadienal | 6750-03-4 | ACHKL |
| 741 | 2,6,10-Trimethylundecanal | 105-88-4 | BDFGJK |
| 742 | alpha,4-Dimethyl benzenepropanal | 41496-43-9 | ACHJK |
| 746 | Allyl cyclohexyl propionate | 2705-87-5 | BDEFHJK |
| 748 | Allyl amyl glycolate | 67634-00-8 | BCEFGJK |
| 750 | Allo-aromadendrene | 25246-27-9 | BDEFHJKL |
| 752 | Aldehyde C-11 | 143-14-6 | ADHJK |
| 754 | Methyl (E)-2-(((3,5-dimethylcyclohex-3-en-1-yl)methylene)amino)benzoate | 94022-83-0 | DEFHJ |
| 757 | 2,6,10-trimethylundec-9-enal | 141-13-9 | BDFHJK |
| 758 | Acetoxymethyl-isolongifolene (isomers) | 59056-62-1 | BDEFHJK |
| 763 | Acetate C9 | 143-13-5 | BDEFHJKL |
| 764 | Acetarolle ® | 744266-61-3 | DFHJK |
| 766 | Acetaldehyde phenylethyl propyl acetal | 7493-57-4 | CEFHJK |
| 767 | Acetaldehyde dipropyl acetal | 105-82-8 | ACEFGIKL |
| 768 | Acetaldehyde benzyl 2-methoxyethyl acetal | 7492-39-9 | BCEFHJK |
| 769 | (Z)-2-(4-methylbenzylidene)heptanal | 84697-09-6 | DHJ |
| 770 | 9-decenal | 39770-05-3 | ADHKL |
| 771 | 8-Hexadecenolide | 123-69-3 | DGJ |
| 772 | 7-Methoxycoumarin | 531-59-9 | CHK |
| 774 | 7-epi-alpha-Selinene | 123123-37-5 | BDEFHJK |
| 775 | 7-eip-alpha-Eudesmol | 123123-38-6 | DEFHJK |
| 776 | 7-Acetyl-1,1,3,4,4,6-hexamethyltetralin | 1506-02-1 | DEFHJ |
| 778 | 6-Isopropylquinoline | 135-79-5 | CEFHJK |
| 781 | 6,6-dimethyl-2-norpinene-2-propionaldehyde | 33885-51-7 | BCFHJK |
| 782 | 6,10,14-trimethyl-2-Pentadecanone | 502-69-2 | DEFHJK |
| 786 | 5-Isopropenyl-2-methyl-2-vinyltetrahydrofuran | 13679-86-2 | ACGIJKL |
| 788 | 5-Cyclohexadecenone | 37609-25-9 | DEFGJK |
| 791 | 4-Terpinenol | 562-74-3 | BCHIJK |
| 792 | 4-Pentenophenone | 3240-29-7 | BCEFHIK |
| 800 | 4-Carvomenthenol | 28219-82-1 | BCHIJK |
| 802 | 4,5,6,7-Tetrahydro-3,6-dimethylbenzofuran | 494-90-6 | BCEFHIJKL |
| 803 | 4-(p-Methoxyphenyl)-2-butanone | 104-20-1 | BCEFHJK |
| 804 | 3-Thujopsanone | 25966-79-4 | BDEFHJK |
| 805 | 3-Propylidenephthalide | 17369-59-4 | CEFHK |
| 806 | 3-Nonylacrolein | 20407-84-5 | BDFHJK |
| 807 | 3-Methyl-5-phenyl-1-pentanal | 55066-49-4 | BDFHJK |
| 814 | 3-Hexenyl isovalerate | 10032-11-8 | ADEFHJKL |
| 821 | 3,6-Dimethyl-3-octanyl acetate | 60763-42-0 | ADEFHJKL |
| 824 | 3,4,5-trimethoxybenzaldehyde | 86-81-7 | BCGIK |
| 826 | 3-(p-Isopropylphenyl)propionaldehyde | 7775-00-0 | BDFHJK |
| 827 | 2-Undecenenitrile | 22629-48-7 | BDEFHJK |
| 828 | 2-Undecenal | 2463-77-6 | ADHJK |

TABLE 1-continued

List of materials with at least one MORV from 1 to 5

| Number | Material Name | CAS Number | Comment Code |
|---|---|---|---|
| 829 | 2-trans-6-trans-Nonadienal | 17587-33-6 | ACHKL |
| 831 | 2-Phenylethyl butyrate | 103-52-6 | DEFHJK |
| 833 | 2-Phenyl-3-(2-furyl)prop-2-enal | 57568-60-2 | CHJ |
| 834 | 2-Phenoxyethanol | 122-99-6 | BCEFGIK |
| 837 | 2-Nonen-1-al | 2463-53-8 | ADHKL |
| 839 | 2-Nonanol | 628-99-9 | BDEFGIKL |
| 840 | 2-Nonanone | 821-55-6 | ADFHIKL |
| 849 | 2-Isobutyl quinoline | 93-19-6 | CEFHJK |
| 850 | 2-Hexylidene cyclopentanone | 17373-89-6 | DFHJKL |
| 852 | 2-Heptyl tetrahydrofuran | 2435-16-7 | BDEFHJKL |
| 856 | 2-Decenal | 3913-71-1 | ADHKL |
| 864 | 2,6-Nonadienal | 26370-28-5 | ACHKL |
| 865 | 2,6-Nonadien-1-ol | 7786-44-9 | ACEFHK |
| 866 | 2,6-dimethyl-octanal | 7779-07-9 | ADFGIJKL |
| 868 | 1-Decanol | 112-30-1 | BDEFGJK |
| 869 | 1-Hepten-1-ol, 1-acetate | 35468-97-4 | ACEFHKL |
| 870 | 10-Undecen-1-ol | 112-43-6 | DEFHJK |
| 871 | 10-Undecenal | 112-45-8 | ADHJK |
| 872 | 10-epi-gamma-Eudesmol | 15051-81-7 | DFHJK |
| 873 | 1,8-Thiocineol | 68391-28-6 | ADEFHIJKL |
| 876 | 1,3,5-undecatriene | 16356-11-9 | ADEFHJKL |
| 877 | 1,2-Dihydrolinalool | 2270-57-7 | BCEFGIJKL |
| 878 | 1,3,3-trimethyl-2-norbornanyl acetate | 13851-11-1 | ADEFHIJKL |
| 879 | 1,1,2,3,3-Pentamethylindan | 1203-17-4 | ADHIJKL |
| 881 | (Z)-6,10-dimethylundeca-5,9-dien-2-yl acetate | 3239-37-0 | DEFHJK |
| 884 | (Z)-3-Dodecenal | 68141-15-1 | BCFHJK |
| 885 | (S)-gamma-Undecalactone | 74568-05-1 | DEFHJKL |
| 886 | (R)-gamma-Undecalactone | 74568-06-2 | DEFHJKL |
| 890 | (E)-6,10-dimethylundeca-5,9-dien-2-yl acetate | 3239-35-8 | DEFHJK |
| 892 | (2Z)-3-methyl-5-phenyl-2-Pentenenitrile | 53243-59-7 | DEFHJK |
| 893 | (2S,5S,6S)-2,6,10,10-tetramethyl-1-oxaspiro[4_5]decan-6-ol | 65620-50-0 | DFHIJK |
| 894 | (2E)-3-methyl-5-phenyl-2-pentenenitrile | 53243-60-0 | CEFHJK |
| 897 | (+)-Dihydrocarveol | 22567-21-1 | BCEFHIJKL |
| 905 | Menthone | 89-80-5 | ADEFGIJKL |
| 908 | (R,E)-2-methyl-4-(2,2,3-trimethylcyclopent-3-en-1-yl)but-2-en-1-ol | 185068-69-3 | CHJK |
| 912 | 2-(8-isopropyl-6-methylbicyclo[2.2.2]oct-5-en-2-yl)-1,3-dioxolane | 68901-32-6 | DEFHJK |
| 913 | gamma-methyl ionone | 7388-22-9 | BDHJK |
| 914 | 3-(3-isopropylphenyl)butanal | 125109-85-5 | BDHJK |
| 916 | 3-(1-ethoxyethoxy)-3,7-dimethylocta-1,6-diene | 40910-49-4 | BDEFHJK |
| 919 | 3a,4,5,6,7,7a-hexahydro-1H-4,7-methanoinden-6-yl propionate | 17511-60-3 | CEFHJK |
| 920 | Bulnesol | 22451-73-6 | DEFHJK |
| 922 | Benzyl phenylacetate | 102-16-9 | DHJ |
| 923 | Benzoin | 119-53-9 | CEFHJ |
| 924 | (E)-1,2,4-trimethoxy-5-(prop-1-en-1-yl)benzene | 2883-98-9 | BCFGJK |
| 925 | alpha,alpha,6,6-tetramethyl bicyclo[3.1.1]hept-2-ene-propanal | 33885-52-8 | BDFHJK |
| 926 | 7-epi-sesquithujene | 159407-35-9 | DEFHJKL |
| 927 | 5-Acetyl-1,1,2,3,3,6-hexamethylindan | 15323-35-0 | DEFHJK |
| 928 | 3-Methylphenethyl alcohol | 1875-89-4 | BCEFHIK |
| 929 | 3,6-Nonadien-1-ol | 76649-25-7 | ACEFHK |
| 930 | 2-Tridecenal | 7774-82-5 | BDFHJK |
| 933 | Patchouli alcohol | 5986-55-0 | DEFHJK |
| 937 | p-Cresyl isobutyrate | 103-93-5 | BDHJK |
| 939 | p-Cresyl n-hexanoate | 68141-11-7 | DEFHJK |
| 941 | 5-hexyl-4-methyldihydrofuran-2(3H)-one | 67663-01-8 | BDEFHIJKL |
| 942 | Ethyl (2Z,4E)-deca-2,4-dienoate | 3025-30-7 | BDEFHJK |
| 943 | Pelargene | 68039-40-7 | DEFHJK |
| 945 | 2-cyclohexylidene-2-phenylacetonitrile | 10461-98-0 | DFHJK |
| 946 | Perillaldehyde | 2111-75-3 | ACHIJK |
| 947 | Perillyl acetate | 15111-96-3 | DFHJK |
| 948 | Perillyl alcohol | 536-59-4 | CHIJK |
| 950 | (2-isopropoxyethyl)benzene | 68039-47-4 | ACEFHJKL |
| 951 | Ethyl (2Z,4E)-deca-2,4-dienoate | 313973-37-4 | BDEFHJK |
| 953 | (2-(cyclohexyloxy)ethyl)benzene | 80858-47-5 | DEFHJK |
| 954 | Phenethyl 2-methylbutyrate | 24817-51-4 | DEFHJK |
| 955 | Phenethyl alcohol | 60-12-8 | BCEFGIK |
| 959 | Phenethyl phenylacetate | 102-20-5 | DHJ |
| 962 | Phenoxanol | 55066-48-3 | DEFHJK |
| 965 | Phenyl benzoate | 93-99-2 | DFHJK |
| 967 | Phenyl ethyl benzoate | 94-47-3 | DHJ |
| 969 | Phenylacetaldehyde ethyleneglycol acetal | 101-49-5 | BCEFGIK |
| 973 | 2-(6,6-dimethylbicyclo[3.1.1]hept-2-en-2-yl)acetaldehyde | 30897-75-7 | ACFHIJKL |
| 974 | Pinocarveol | 5947-36-4 | BCEFGIJKL |
| 976 | Piperonyl acetone | 55418-52-5 | CEFGJ |
| 978 | 3a,4,5,6,7,7a-hexahydro-1H-4,7-methanoinden-6-yl pivalate | 68039-44-1 | DEFHJK |
| 980 | (4aR,8aS)-7-methyloctahydro-1,4-methanonaphthalen-6(2H)-one | 41724-19-0 | CEFGJKL |
| 982 | p-Menth-3-en-1-ol | 586-82-3 | BCGIJK |
| 985 | (E)-3,3-dimethyl-5-(2,2,3-trimethylcyclopent-3-en-1-yl)pent-4-en-2-ol | 107898-54-4 | DHJK |
| 988 | 1-methyl-4-(4-methylpent-3-en-1-yl)cyclohex-3-ene-1-carbaldehyde | 52474-60-9 | DFHJK |
| 993 | Propylene glycol | 57-55-6 | ACEFGIKL |
| 998 | p-Tolyl phenylacetate | 101-94-0 | DFHJ |
| 1000 | Ethyl 2,4,7-decatrienoate | 78417-28-4 | BDEFHJK |
| 1003 | 2-benzyl-4,4,6-trimethyl-1,3-dioxane | 67633-94-7 | DEFHJK |
| 1006 | 2,4-dimethyl-4-phenyltetrahydrofuran | 82461-14-1 | BDEFHJK |
| 1007 | (2R,4a'R,8a'R)-3,7'-dimethyl-3',4',4a',5',8',8a'-hexahydro-1'H-spiro[oxirane-2,2'-[1,4]methanonaphthalene] | 41816-03-9 | DEFHJK |
| 1008 | (Z)-6-ethylideneoctahydro-2H-5,8-methanochromene | 93939-86-7 | BCEFHJKL |
| 1009 | 2-((S)-1-((S)-3,3-dimethylcyclohexyl)ethoxy)-2-oxoethyl propionate | 236391-76-7 | DFHJ |
| 1010 | Methyl 2,2-dimethyl-6-methylenecyclohexane-1-carboxylate | 81752-87-6 | ADHIJKL |
| 1012 | 2-methyl-5-phenylpentan-1-ol | 25634-93-9 | DEFHJK |
| 1016 | 4-methyl-2-phenyl-3,6-dihydro-2H-pyran | 60335-71-9 | BCEFGJK |
| 1020 | Sabinol | 471-16-9 | BCEFHIJKL |
| 1021 | Safrole | 94-59-7 | BCEFHK |
| 1022 | 2,2,7,9-tetramethylspiro(5.5)undec-8-en-1-one | 502847-01-0 | DHIJK |
| 1023 | 3-methyl-5-(2,2,3-trimethylcyclopent-3-en-1-yl)pentan-2-ol | 65113-99-7 | DEFHJK |
| 1024 | (Z)-2-ethyl-4-(2,2,3-trimethylcyclopent-3-en-1-yl)but-2-en-1-ol | 28219-61-6 | DEFHJK |
| 1025 | (E)-2-methyl-4-(2,2,3-trimethylcyclopent-3-en-1-yl)but-2-en-1-ol | 28219-60-5 | CHJK |
| 1026 | 5-methoxyoctahydro-1H-4,7-methanoindene-2-carbaldehyde | 86803-90-9 | CHJK |
| 1027 | 5-methoxyhydro-1H-4,7-methanoindene-2-carbaldehyde | 193425-86-4 | CHJK |
| 1028 | Sclareol | 515-03-7 | DEFHJ |
| 1029 | Sclareol oxide | 5153-92-4 | DEFHJK |
| 1031 | Selina-3,7(11)-diene | 6813-21-4 | DEFHJKL |
| 1032 | 2-(1-(3,3-dimethylcyclohexyl)ethoxy)-2-methylpropyl cyclopropanecarboxylate | 477218-42-1 | DEFHJ |
| 1033 | 3-(4-isobutylphenyl)-2-methylpropanal | 6658-48-6 | DHJK |
| 1035 | Spathulenol | 6750-60-3 | DEFHJK |
| 1036 | Spirambrene | 533925-08-5 | BCEFHJK |

TABLE 1-continued

List of materials with at least one MORV from 1 to 5

| Number | Material Name | CAS Number | Comment Code |
|---|---|---|---|
| 1037 | Spirodecane | 6413-26-9 | BCEFGIJKL |
| 1038 | 1-(spiro[4.5]dec-7-en-7-yl)pent-4-en-1-one | 224031-70-3 | DGJK |
| 1042 | 2-(4-methylthiazol-5-yl)ethan-1-ol | 137-00-8 | CGIKL |
| 1043 | 2-(heptan-3-yl)-1,3-dioxolane | 4359-47-1 | ACEFHIJKL |
| 1045 | (Z)-dodec-4-enal | 21944-98-9 | BDFHJK |
| 1046 | tau-Cadinol | 5937-11-1 | DEFHJK |
| 1047 | tau-Muurolol | 19912-62-0 | DEFHJK |
| 1053 | Tetrahydrojasmone | 13074-63-0 | BDFHIJKL |
| 1057 | 2,6,10,10-tetramethyl-1-oxaspiro[4.5]dec-6-ene | 36431-72-8 | BDFHIJKL |
| 1059 | Thiomenthone | 38462-22-5 | BDEFHIJKL |
| 1060 | Thujopsene | 470-40-6 | BDEFGJKL |
| 1062 | Thymol methyl ether | 1076-56-8 | ADHIJKL |
| 1063 | 1-(2,2,6-trimethylcyclohexyl)hexan-3-ol | 70788-30-6 | DEFHJK |
| 1064 | trans, trans-2,4-Nonadienal | 5910-87-2 | ACHKL |
| 1065 | trans, trans-Farnesol | 106-28-5 | DEFHJK |
| 1066 | trans-2, cis-6-Nonadienal | 557-48-2 | ACHKL |
| 1067 | trans-2-Decenal | 3913-81-3 | ADHKL |
| 1070 | trans-2-Nonen-1-al | 18829-56-6 | ADHKL |
| 1072 | trans-3, cis-6-nonadienol | 56805-23-3 | ACEFHK |
| 1073 | trans-4-Decen-1-al | 65405-70-1 | ADHKL |
| 1075 | trans-ambrettolide | 51155-12-5 | DGJ |
| 1077 | trans-beta-ocimene | 13877-91-3 | ADGIKL |
| 1078 | trans-beta-Ocimene | 3779-61-1 | ADGIKL |
| 1082 | trans-Geraniol | 106-24-1 | BCHIK |
| 1083 | trans-Hedione | 2570-03-8 | DFHJK |
| 1085 | 7-(1,1-Dimethylethyl)-2H-1,5-benzodioxepin-3(4H)-one | 195251-91-3 | CEFHJ |
| 1089 | Tricyclone | 68433-81-8 | DEFHJK |
| 1090 | Tridecyl alcohol | 112-70-9 | DEFGJK |
| 1091 | Triethyl citrate | 77-93-0 | CEFGJ |
| 1093 | Methyl 2-((1-hydroxy-3-phenylbutyl)amino)benzoate | 144761-91-1 | DFHJ |
| 1095 | 1-((2E,5Z,9Z)-2,6,10-trimethylcyclododeca-2,5,9-trien-1-yl)ethan-1-one | 28371-99-5 | DHJK |
| 1097 | Decahydro-2,6,6,7,8,8-hexamethyl-2h-indeno(4,5-b)furan | 338735-71-0 | BDEFHJK |
| 1099 | 13-methyl oxacyclopentadec-10-en-2-one | 365411-50-3 | DEFHJK |
| 1102 | Undecanal | 112-44-7 | BDHJK |
| 1104 | (E)-4-methyldec-3-en-5-ol | 81782-77-6 | BDEFHIJK |
| 1105 | Valencene | 4630-07-3 | BDEFHJK |
| 1107 | Valerianol | 20489-45-6 | DEFHJK |
| 1111 | Vanillin isobutyrate | 20665-85-4 | CHJ |
| 1113 | Vaniwhite ® | 5533-03-9 | CGIK |
| 1116 | (Z)-2-methyl-4-(2,6,6-trimethylcyclohex-2-en-1-yl)but-2-enal | 68555-62-4 | BDFHJK |
| 1117 | Methyl 2,4-dihydroxy-3,6-dimethylbenzoate | 4707-47-5 | CGIJ |
| 1120 | 1-methoxy-3a,4,5,6,7,7a-hexahydro-1H-4,7-methanoindene | 27135-90-6 | ACEFHJKL |
| 1121 | Methyl (Z)-2-((3-(4-(tert-butyl)phenyl)-2-methylpropylidene)amino)benzoate | 91-51-0 | DFHJ |
| 1125 | (Z)-hex-3-en-1-yl isobutyrate | 41519-23-7 | ADEFHJKL |
| 1126 | Vertacetal | 5182-36-5 | BCFHJK |
| 1129 | 1-((3R,3aR,7R,8aS)-3,6,8,8-tetramethyl-2,3,4,7,8,8a-hexahydro-1H-3a,7-methanoazulen-5-yl)ethan-1-one | 32388-55-9 | DHJK |
| 1131 | Methyl (Z)-2-(((2,4-dimethylcyclohex-3-en-1-yl)methylene)amino)benzoate | 68738-99-8 | DEFHJ |
| 1135 | Vetiverol | 89-88-3 | CEFHIJK |
| 1136 | Vetivert Acetate | 117-98-6 | DEFHJK |
| 1137 | Decahydro-3H-spiro[furan-2,5'-[4,7]methanoindene] | 68480-11-5 | DEFGJKL |
| 1138 | (2Z,6E)-nona-2,6-dienenitrile | 67019-89-0 | ACEFHKL |
| 1139 | (Z)-cyclooct-4-en-1-yl methyl carbonate | 87731-18-8 | BCHJKL |
| 1140 | (1aR,4S,4aS,7R,7aS,7bS)-1,1,4,7-tetramethyldecahydro-1H-cyclopropa[e]azulen-4-ol | 552-02-3 | DEFHJK |
| 1142 | 3,5,5,6,7,8,8-heptamethyl-5,6,7,8-tetrahydronaphthalene-2-carbonitrile | 127459-79-4 | DHJ |
| 1143 | (1S,2S,3S,5R)-2,6,6-trimethylspiro[bicyclo[3.1.1]heptane-3,1'-cyclohexan]-2'-en-4'-one | 133636-82-5 | DEFHJK |
| 1144 | 1',1',5',5'-tetramethylhexahydro-2'H,5'H-spiro[[1,3]dioxolane-2,8'-[2,4a]methanonaphthalene] | 154171-76-3 | DEFHJK |
| 1145 | 1',1',5',5'-tetramethylhexahydro-2'H,5'H-spiro[[1,3]dioxolane-2,8'-[2,4a]methanonaphthalene] K | 154171-77-4 | DEFHJK |
| 1146 | 4-(4-hydroxy-3-methoxyphenyl)butan-2-one | 122-48-5 | CEFGJ |
| 1147 | (1R,8aR)-4-isopropyl-1,6-dimethyl-1,2,3,7,8,8a-hexahydronaphthalene | 41929-05-9 | DEFHJKL |
| 1148 | 4,5-epoxy-4,11,11-trimethyl-8-methylenebicyclo(7.2.0)undecane | 1139-30-6 | DEFHJK |
| 1149 | 1,3,4,6,7,8alpha-hexahydro-1,1,5,5-tetramethyl-2H-2,4alpha-methanophtalen-8(5H)-one | 23787-90-8 | DEFHIJK |

TABLE 2

List of materials with at least one MORV greater than 5 to 10

| Number | Material Name | CAS Number | Comment Code |
|---|---|---|---|
| 2 | 2,4-dimethyl-2-(5,5,8,8-tetramethyl-5,6,7,8-tetrahydronaphthalen-2-yl)-1,3-dioxolane | 131812-67-4 | DFHJ |
| 23 | 3a,5,6,7,8,8b-hexahydro-2,2,6,6,7,8,8-heptamethyl-4H-indeno(4,5-d)-1,3-dioxole | 823178-41-2 | DEFHJK |
| 141 | 2,4-dimethyl-4,4a,5,9b-tetrahydroindeno[1,2-d][1,3]dioxine | 27606-09-3 | CEFHJK |
| 185 | (1-methyl-2-((1,2,2-trimethylbicyclo[3.1.0]hexan-3-yl)methyl)cyclopropyl)methanol | 198404-98-7 | DEFHJK |
| 227 | Isobornylcyclohexanol | 68877-29-2 | DEFHJK |
| 230 | Isobornyl cyclohexanol | 66072-32-0 | DEFHJK |
| 246 | Indol/Hydroxycitronellal Schiff base | 67801-36-9 | DEFHJ |
| 248 | Hydroxymethyl isolongifolene | 59056-64-3 | DEFHJK |
| 343 | 8,8-dimethyl-3a,4,5,6,7,7a-hexahydro-1H-4,7-methanoinden-6-yl propionate | 76842-49-4 | DEFHJK |
| 359 | (E)-4-((3aR,4R,7R,7aR)-1,3a,4,6,7,7a-hexahydro-5H-4,7-methanoinden-5-ylidene)-3-methylbutan-2-ol | 501929-47-1 | DEFHJK |
| 565 | Cedryl methyl ether | 19870-74-7 | BDEFHJK |
| 631 | beta-Copaene | 18252-44-3 | BDEFHJKL |
| 659 | 2'-isopropyl-1,7,7-trimethylspiro[bicyclo[2.2.1]heptane-2,4'-[1,3]dioxane] | 869292-93-3 | BDEFHJK |
| 674 | (4aR,5R,7aS,9R)-2,2,5,8,8,9a-hexamethyloctahydro-4H-4a,9-methanoazuleno[5,6-d][1,3]dioxole | 211299-54-6 | DEFHJK |
| 678 | (3S,5aR,7aS,11aS,11bR)-3,8,8,11a-tetramethyldodecahydro-5H-3,5a-epoxynaphtho[2,1-c]oxepine | 57345-19-4 | DEFHJ |
| 679 | 2,2,6,6,7,8,8-heptamethyldecahydro-2H-indeno[4,5-b]furan | 476332-65-7 | DEFHJK |
| 715 | alpha-Cedrene epoxide | 13567-39-0 | BDEFHJK |
| 758 | Acetoxymethyl-isolongifolene (isomers) | 59056-62-1 | DEFHJK |
| 1028 | Sclareol | 515-03-7 | DEFHJ |
| 1097 | Decahydro-2,6,6,7,8,8-hexamethyl-2h-indeno(4,5-b)furan | 338735-71-0 | DEFHJK |

TABLE 3

List of materials with at least one MORV from 0.5 to less than 1

| Number | Material Name | CAS Number | Comment Code |
|---|---|---|---|
| 12 | 1-ethoxy-4-(tert-pentyl)cyclohexane | 181258-89-9 | ADEFHJK |
| 19 | (3Z)-1-(2-buten-1-yloxy)-3-hexene | 888744-18-1 | ADEFHJKL |
| 20 | 4-(2-methoxypropan-2-yl)-1-methylcyclohex-1-ene | 14576-08-0 | ADHIJKL |
| 24 | O-Methyl linalool | 60763-44-2 | ADHIJKL |
| 26 | o-Methoxycinnamaldehyde | 1504-74-1 | ACHK |
| 27 | Octanal, 3,7-dimethyl- | 25795-46-4 | ADGIJKL |
| 53 | 3,3-Dimethyl-5(2,2,3-Trimethyl-3-Cyclopenten-1yl)-4-Penten-2-ol | 329925-33-9 | CEFHJ |
| 54 | n-Hexyl salicylate | 6259-76-3 | DEFHJ |
| 55 | n-Hexyl 2-butenoate | 19089-92-0 | ADEFHJKL |
| 59 | Neryl Formate | 2142-94-1 | BCEFHJK |
| 72 | Methyl-beta-ionone | 127-43-5 | DHJK |
| 73 | Myroxide | 28977-57-3 | ADGIJKL |
| 81 | (E)-3,7-dimethylocta-4,6-dien-3-ol | 18479-54-4 | BCEFGIJK |
| 84 | (Z)-hex-3-en-1-yl cyclopropanecarboxylate | 188570-78-7 | BCEFHIKL |
| 96 | Methyl phenyl carbinyl propionate | 120-45-6 | BCHJK |
| 97 | Methyl phenylacetate | 101-41-7 | ACEFHIKL |
| 107 | 2-methyl-6-oxaspiro[4.5]decan-7-one | 91069-37-3 | BCEFGIKL |
| 111 | Methyl geraniate | 2349-14-6 | BCHJKL |
| 115 | 2-ethoxy-4-(methoxymethyl)phenol | 5595-79-9 | CFGK |
| 116 | Methyl cyclopentylideneacetate | 40203-73-4 | ACEFHIKL |
| 125 | Methoxymelonal | 62439-41-2 | ACGIJK |
| 133 | ((1s,4s)-4-isopropylcyclohexyl)methanol | 13828-37-0 | BDEFHIJK |
| 147 | Linalyl propionate | 144-39-8 | BDFHJK |
| 150 | Linalyl formate | 115-99-1 | ACFHJK |
| 151 | Linalyl butyrate | 78-36-4 | BDEFHJK |
| 154 | Linalyl acetate | 115-95-7 | BDHJK |
| 157 | Linalool | 78-70-6 | BCEFGIJK |
| 163 | (Z)-hex-3-en-1-yl methyl carbonate | 67633-96-9 | ACEFGKL |
| 166 | Lepidine | 491-35-0 | BCEFHIKL |
| 169 | L-Carvone | 6485-40-1 | ACGIJKL |
| 181 | Khusinil | 75490-39-0 | DHJK |
| 191 | Isoraldeine | 1335-46-2 | BDHIJK |
| 194 | Isopropylvinylcarbinol | 4798-45-2 | ACGIKL |
| 198 | Isopropyl 2-methylbutyrate | 66576-71-4 | ACEFGIJKL |
| 201 | Isopentyrate | 80118-06-5 | ADEFGIJKL |
| 204 | Isononyl acetate | 40379-24-6 | BDEFHJKL |
| 205 | Isononanol | 27458-94-2 | BDEFGIKL |
| 213 | Isoeugenyl acetate | 93-29-8 | CFHJK |
| 214 | Isoeugenol | 97-54-1 | CEFHIK |
| 232 | Isoborneol | 124-76-5 | ACEFHIJKL |
| 237 | Isoamyl octanoate | 2035-99-6 | DEFHJK |
| 239 | Isoamyl isobutyrate | 2050-01-3 | ACEFGIJKL |
| 255 | Hydrocinnamic acid | 501-52-0 | CEFHIK |
| 258 | Hydratopic alcohol | 1123-85-9 | BCEFHIK |
| 264 | Hexyl propanoate | 2445-76-3 | ADEFHIKL |
| 270 | Hexyl butyrate | 2639-63-6 | BDEFHJKL |
| 273 | Hexyl 2-methylbutanoate | 10032-15-2 | BDEFHJKL |
| 275 | Hexyl 2-furoate | 39251-86-0 | DEFHJK |
| 282 | Heptyl alcohol | 111-70-6 | ACEFGIKL |
| 283 | Heptyl acetate | 112-06-1 | ADEFHKL |
| 284 | Heptaldehyde | 111-71-7 | ACHIKL |
| 287 | Heliotropin | 120-57-0 | BCGIK |
| 302 | Geranyl nitrile | 5146-66-7 | BCEFHKL |
| 306 | Geranyl formate | 105-86-2 | BCEFHJK |
| 308 | Geranyl caprylate | 51532-26-4 | DEFHJ |
| 310 | Geranyl benzoate | 94-48-4 | DFHJ |
| 312 | Geranial | 141-27-5 | ACHIKL |
| 314 | N,2-dimethyl-N-phenylbutanamide | 84434-18-4 | BCEFHJK |
| 319 | gamma-Terpinene | 99-85-4 | ADEFGIJKL |
| 346 | 2-(sec-butyl)cyclohexan-1-one | 14765-30-1 | ADFHIKL |
| 354 | 3-(2-ethylphenyl)-2,2-dimethylpropanal | 67634-14-4 | BDHJK |
| 355 | 2-(tert-butyl)cyclohexyl ethyl carbonate | 67801-64-3 | BDFHJK |
| 365 | 2-(tert-butyl)cyclohexyl ethyl carbonate | 81925-81-7 | ACFHIKL |
| 366 | Fenchyl alcohol | 1632-73-1 | ACGIJKL |
| 376 | Eucalyptol | 470-82-6 | ADEFGIJKL |
| 379 | Ethyl vanillin acetate | 72207-94-4 | CHJ |
| 387 | Ethyl octanoate | 106-32-1 | BDEFHJKL |
| 400 | Ethyl cinnamate | 103-36-6 | BCEFHK |
| 412 | Ethyl 2-(cyclohexyl)propionate | 2511-00-4 | BDFHIJKL |
| 419 | d-p-8(9)-Menthen-2-one | 5524-05-0 | ACGIJKL |
| 420 | 4-methyl-2-phenyltetrahydro-2H-pyran | 94201-73-7 | BDEFHJK |
| 437 | Dihydromyrcenol | 18479-58-8 | ADEFGIJK |
| 438 | Dihydrojasmone | 1128-08-1 | BCFHJKL |
| 439 | Dihydroisophorone | 873-94-9 | ACEFGIJKL |
| 440 | Dihydroeugenol | 2785-87-7 | CEFHJ |
| 442 | Dihydrocoumarin | 119-84-6 | BCGIKL |
| 443 | Dihydrocarvone | 7764-50-3 | ACGIJKL |
| 447 | Dihydro-alpha-terpinyl acetate | 80-25-1 | BDEFHIJKL |
| 448 | Dihydro-alpha-ionone | 31499-72-6 | BDHJK |
| 454 | Dibenzyl ether | 103-50-4 | DEFHJK |
| 455 | Dibutyl o-phthalate | 84-74-2 | DEFHJ |
| 469 | 2-pentylcyclopentan-1-one | 4819-67-4 | BDFHIKL |
| 472 | Decyl anthranilate | 18189-07-6 | DEFHJ |
| 477 | Methyl (1s,4s)-1,4-dimethylcyclohexane-1-carboxylate | 23059-38-3 | ADEFHIJKL |
| 481 | Cyclohexylethyl acetate | 21722-83-8 | BDEFHJKL |
| 492 | Creosol | 93-51-6 | BCHIK |
| 495 | Cosmene | 460-01-5 | ADEFGIKL |
| 496 | 4-cyclohexyl-2-methylbutan-2-ol | 83926-73-2 | BDEFGIJK |
| 504 | 2-benzyl-2-methylbut-3-enenitrile | 97384-48-0 | BDHJK |
| 509 | Citronellyl nitrile | 51566-62-2 | BCEFGIKL |
| 510 | Citronellyl phenylacetate | 139-70-8 | DFHJ |
| 512 | Citronellyl formate | 105-85-1 | BCEFGJKL |
| 515 | Citronellyl benzoate | 10482-77-6 | DFHJ |
| 517 | Citronellol | 106-22-9 | BCHIJKL |
| 518 | Citronellal | 106-23-0 | ACHIJKL |
| 522 | Citral | 5392-40-5 | ACHIKL |
| 525 | cis-Pinane | 6876-13-7 | ADEFGIJKL |
| 526 | (Z)-3-methyl-2-(pent-2-en-1-yl)cyclopent-2-en-1-one | 488-10-8 | BCHIJKL |
| 528 | cis-iso-Eugenol | 5912-86-7 | CEFHIK |
| 535 | cis-3-Hexenyl valerate | 35852-46-1 | BDEFHJKL |
| 536 | cis-3-Hexenyl tiglate | 67883-79-8 | BDEFHJK |
| 538 | cis-3-Hexenyl propionate | 33467-74-2 | ADEFHIKL |
| 540 | cis-3-Hexenyl butyrate | 16491-36-4 | ADEFHJKL |
| 542 | cis-3-Hexen-1-ol | 928-96-1 | ACEFHIKL |
| 547 | cis-2-Hexenol | 928-94-9 | ACEFHIKL |
| 549 | Cinnamyl nitrile | 4360-47-8 | ACEFGIK |
| 554 | Cinnamic aldehyde | 104-55-2 | ACHIK |
| 556 | Cinnamyl nitrile | 1885-38-7 | ACEFGIK |
| 557 | Chloroxylenol | 88-04-0 | BCHIJK |
| 575 | Carvacrol | 499-75-2 | DHIJK |
| 576 | Carvone | 99-49-0 | ACGIJKL |
| 579 | Carbitol | 111-90-0 | BCEFGIK |
| 583 | Caproyl alcohol | 111-27-3 | ACEFGIKL |
| 585 | 2-(2,2,3-trimethylcyclopent-3-en-1-yl)acetonitrile | 15373-31-6 | ACGIJKL |
| 588 | Camphor | 76-22-2 | ACEFGIJKL |
| 602 | (E)-2-methyl-4-(2,6,6-trimethylcyclohex-1-en-1-yl)but-2-enal | 3155-71-3 | DHJK |
| 605 | Borneol | 507-70-0 | ACEFHIJKL |
| 617 | beta-Pinene epoxide | 6931-54-0 | ACEFGIJKL |
| 619 | beta-Phellandrene | 555-10-2 | ADEFGIJKL |
| 640 | Benzylacetone | 2550-26-7 | ACEFGIK |
| 641 | Benzyl salicylate | 118-58-1 | DFGJ |

TABLE 3-continued

List of materials with at least one MORV from 0.5 to less than 1

| Number | Material Name | CAS Number | Comment Code |
|---|---|---|---|
| 645 | Benzyl isovalerate | 103-38-8 | BDEFHJK |
| 647 | Benzyl isobutyrate | 103-28-6 | BCHJK |
| 651 | Benzyl butyrate | 103-37-7 | BCEFHJK |
| 652 | Benzyl alcohol | 100-51-6 | ACEFGIKL |
| 662 | 1-(3,3-dimethylcyclohexyl)ethyl formate | 25225-08-5 | ADEFHIJKL |
| 664 | Anisyl acetate | 104-21-2 | BCEFGK |
| 665 | Anisyl formate | 122-91-8 | BCEFGK |
| 667 | Anethole | 104-46-1 | ACEFHK |
| 672 | Amyl benzoate | 2049-96-9 | DEFHJK |
| 687 | alpha-Terpinyl acetate | 80-26-2 | BDHJK |
| 699 | alpha-methyl-cyclohexanepropanol | 10528-67-3 | BDEFHIK |
| 701 | alpha-methyl cinnamaldehyde | 101-39-3 | ACHIK |
| 703 | alpha-Isomethylionone | 127-51-5 | BDHIJK |
| 740 | 2,5-Dimethyl-4-methoxy-3(2H)-furanone | 4077-47-8 | ACEFGIJKL |
| 743 | Allyl phenoxyacetate | 7493-74-5 | BCGK |
| 744 | Allyl Phenethyl ether | 14289-65-7 | ACEFHK |
| 745 | Allyl heptanoate | 142-19-8 | ADEFHJKL |
| 755 | N-ethyl-N-(m-tolyl)propionamide | 179911-08-1 | CEFHJK |
| 760 | 3-hydroxybutan-2-one | 513-86-0 | ACEFGIKL |
| 761 | Acetoanisole | 100-06-1 | BCEFHIK |
| 777 | 6-Methylquinoline | 91-62-3 | BCEFHIKL |
| 779 | 6,8-Diethyl-2-nonanol | 70214-77-6 | BDEFGIJKL |
| 784 | 5-Methyl-3-heptanone | 541-85-5 | ACFGIKL |
| 789 | 4-Vinylphenol | 2628-17-3 | BCHIK |
| 796 | 4-hydroxy-3-methoxy-cinnamaldehyde | 458-36-6 | CH |
| 797 | 4-Ethylguaiacol | 2785-89-9 | CEFHIK |
| 799 | 4-Damascol | 4927-36-0 | BDFHJK |
| 808 | 3-methyl-4-phenylpyrazole | 13788-84-6 | CEFHK |
| 810 | 3-Methyl-1,2-cyclopentanedione | 765-70-8 | ACEFGIKL |
| 811 | 3-Methoxy-5-methylphenol | 3209-13-0 | BCHIK |
| 812 | 3-Methoxy-3-Methyl Butanol | 56539-66-3 | ACGIKL |
| 817 | 3-Hexenol | 544-12-7 | ACEFHIKL |
| 819 | 3,7-dimethyl-2-methylene-6-octenal | 22418-66-2 | ADFHJK |
| 820 | 3,7-dimethyl-1-octanol | 106-21-8 | BDEFGIJKL |
| 832 | 2-Phenylethyl acetate | 103-45-7 | BCEFHK |
| 835 | 2-Phenethyl propionate | 122-70-3 | BCEFHJK |
| 836 | 2-Pentylcyclopentan-1-ol | 84560-00-9 | DEFHKL |
| 838 | 2-nonanone propylene glycol acetal | 165191-91-3 | BDEFHJK |
| 845 | 2-Methoxy-3-(1-methylpropyl)pyrazine | 24168-70-5 | BCEFGIK |
| 846 | 2-isopropyl-N,2,3-trimethylbutyramide | 51115-67-4 | ACEFGIJK |
| 847 | 2-Isopropyl-5-methyl-2-hexenal | 35158-25-9 | ADFGIJKL |
| 848 | 2-Isopropyl-4-methylthiazole | 15679-13-7 | ACHIJKL |
| 851 | 2-Hexen-1-ol | 2305-21-7 | ACEFHIKL |
| 858 | 2-Butoxyethanol | 111-76-2 | ACEFGIKL |
| 875 | 1,4-Cineole | 470-67-7 | ADGIJKL |
| 880 | 1-(2,6,6-Trimethyl-2-cyclohexen-1-yl)-2-buten-1-one | 43052-87-5 | BDHIJK |
| 882 | (Z)-3-hepten-1-yl acetate | 1576-78-9 | ACEFHKL |
| 883 | (S)-(1R,5R)-4,6,6-trimethylbicyclo[3.1.1]hept-3-en-2-one | 1196-01-6 | ACEFGIJKL |
| 888 | (R)-(−)-Linalool | 126-91-0 | BCEFGIJK |
| 889 | (l)-Citronellal | 5949-05-3 | ACHIJKL |
| 891 | (d)-Citronellal | 2385-77-5 | ACHIJKL |
| 899 | (+)-Citronellol | 1117-61-9 | BCHIJKL |
| 900 | (−)-Citronellol | 7540-51-4 | BCHIJKL |
| 901 | (+)-alpha-Pinene | 7785-70-8 | ADEFGIJKL |
| 902 | (+)-Carvone | 2244-16-8 | ACGIJKL |
| 903 | (−)-alpha-Pinene | 7785-26-4 | ADEFGIJKL |
| 904 | Methyl 2-methylbutyrate | 868-57-5 | ACEFGIKL |
| 909 | Hexyl tiglate | 16930-96-4 | BDEFHJKL |
| 918 | Allyl 2-(cyclohexyloxy)acetate | 68901-15-5 | CHJK |
| 921 | 1,5-dimethylbicyclo[3.2.1]octan-8-one oxime | 75147-23-8 | CFHJK |
| 931 | alpha-acetoxystyrene | 2206-94-2 | ACEFHIK |
| 940 | p-Cymene | 99-87-6 | ADGIJKL |
| 956 | Phenethyl formate | 104-62-1 | ACEFHK |
| 958 | Phenethyl isobutyrate | 103-48-0 | DHJK |
| 960 | Phenethyl tiglate | 55719-85-2 | DHJK |
| 971 | Phenylethyl methacrylate | 3683-12-3 | DHJK |
| 977 | p-Isopropylphenylacetaldehyde | 4395-92-0 | BDFHK |
| 981 | 1,2-dimethyl-3-(prop-1-en-2-yl)cyclopentan-1-ol | 72402-00-7 | BCEFGIJKL |
| 983 | p-Methoxyphenylacetone | 122-84-9 | BCEFHK |
| 986 | (2Z,5Z)-5,6,7-trimethylocta-2,5-dien-4-one | 358331-95-0 | ADHIJKL |
| 987 | p-Propyl anisole | 104-45-0 | ADEFHKL |
| 994 | p-t-butyl phenyl acetaldehyde | 109347-45-7 | BDHJK |
| 995 | p-tert-Amyl cyclohexanol | 5349-51-9 | BDEFHIJK |
| 1001 | Racemic alpha-Pinene | 80-56-8 | ADEFGIJKL |
| 1002 | 4-(4-hydroxyphenyl)butan-2-one | 5471-51-2 | CEFGIK |
| 1004 | Rhodinol | 141-25-3 | BCHIJKL |
| 1005 | Ethyl (2,3,6-trimethylcyclohexyl) carbonate | 93981-50-1 | BDEFHJKL |
| 1011 | 1-(3,3-dimethylcyclohexyl)ethyl acetate | 25225-10-9 | ADHIJKL |
| 1017 | S)-(+)-Linalool | 126-90-9 | BCEFGIJK |
| 1018 | Sabinene | 3387-41-5 | ADEFGIJKL |
| 1019 | Sabinene hydrate | 546-79-2 | ADEFGIJKL |
| 1030 | Propyl (S)-2-(tert-pentyloxy)propanoate | 319002-92-1 | BDEFHJK |
| 1039 | Spirolide | 699-61-6 | BCGIKL |
| 1040 | (Z)-5-methylheptan-3-one oxime | 22457-23-4 | BCEFGIJKL |
| 1041 | 1-phenylethyl acetate | 93-92-5 | ACEFHIK |
| 1051 | Tetrahydrogeranial | 5988-91-0 | ADGIJKL |
| 1052 | Tetrahydroionol | 4361-23-3 | BDEFHJK |
| 1054 | Tetrahydrolinalool | 78-69-3 | BDEFGIJKL |
| 1055 | Tetrahydrolinalyl acetate | 20780-48-7 | ADEFHJKL |
| 1058 | Ethyl (1R,6S)-2,2,6-trimethylcyclohexane-1-carboxylate | 22471-55-2 | ADEFHIJKL |
| 1061 | Thymol (2-isopropyl-5-methylphenol) | 89-83-8 | BDHIJK |
| 1069 | trans-2-Hexenol | 928-95-0 | ACEFHIKL |
| 1071 | trans-2-tert-Butylcyclohexanol | 5448-22-6 | ACGIJKL |
| 1074 | trans-alpha-Damascone | 24720-09-0 | BDHIJK |
| 1076 | trans-Anethole | 4180-23-8 | ACEFHK |
| 1079 | trans-Cinnamic acid | 140-10-3 | CEFHK |
| 1081 | trans-Dihydrocarvone | 5948-04-9 | ACGIJKL |
| 1084 | trans-Isoeugenol | 5932-68-3 | CEFHIK |
| 1088 | Trichloromethyl phenyl carbinyl acetate | 90-17-5 | BDEFGJ |
| 1098 | 2-mercapto-2-methylpentan-1-ol | 258823-39-1 | ACEFHIJKL |
| 1110 | Vanillin acetate | 881-68-5 | CH |
| 1112 | Vanitrope | 94-86-0 | CEFHK |
| 1115 | 2,2,5-trimethyl-5-pentylcyclopentan-1-one | 65443-14-3 | BDFGIJKL |
| 1118 | Veratraldehyde | 120-14-9 | BCGIK |
| 1119 | (1R,5R)-4,6,6-trimethylbicyclo[3.1.1]hept-3-en-2-one | 18309-32-5 | ACEFGIJKL |
| 1122 | Verdol | 13491-79-7 | ACGIJKL |
| 1127 | 4-(tert-butyl)cyclohexyl acetate | 10411-92-4 | BDEFHJK |
| 1128 | 4-(tert-butyl)cyclohexyl acetate | 32210-23-4 | BDEFHJK |

TABLE 3-continued

List of materials with at least one MORV from 0.5 to less than 1

| Number | Material Name | CAS Number | Comment Code |
|---|---|---|---|
| 1133 | Vethymine | 7193-87-5 | CEFGK |
| 1134 | 4-methyl-4-phenylpentan-2-yl acetate | 68083-58-9 | BDFHJK |
| 1141 | (Z)-1-((2-methylallyl)oxy)hex-3-ene | 292605-05-1 | ADEFHKL |

TABLE 4

List of materials with ALL MORVs from 1 to 5

| Number | Material Name | CAS Number | Comment Code |
|---|---|---|---|
| 7 | 3-methoxy-7,7-dimethyl-10-methylenebicyclo[4.3.1]decane | 216970-21-7 | BDEFHJK |
| 14 | Oxyoctaline formate | 65405-72-3 | DFHJK |
| 39 | 2,2,6,8-tetramethyl-1,2,3,4,4a,5,8,8a-octahydronaphthalen-1-ol | 103614-86-4 | DEFHIJK |
| 48 | Nootkatone | 4674-50-4 | DHJK |
| 183 | Khusimol | 16223-63-5 | CEFHJK |
| 199 | Isopimpinellin | 482-27-9 | CFGJ |
| 206 | Iso3-methylcyclopentadecan-1-one | 3100-36-5 | DEFGJK |
| 212 | Isoeugenyl benzyl ether | 120-11-6 | DFHJ |
| 215 | 1-((2S,3S)-2,3,8,8-tetramethyl-1,2,3,4,5,6,7,8-octahydronaphthalen-2-yl)ethan-1-one | 54464-57-2 | DHJK |
| 229 | Isobornyl isobutyrate | 85586-67-0 | BDEFHIJK |
| 260 | 2,3-dihydro-3,3-dimethyl-1H-indene-5-propanal | 173445-44-8 | DHJK |
| 261 | 3-(3,3-dimethyl-2,3-dihydro-1H-inden-5-yl)propanal | 173445-65-3 | DHJK |
| 281 | 3a,4,5,6,7,7a-hexahydro-1H-4,7-methanoinden-6-yl acetate | 5413-60-5 | CEFGJK |
| 329 | gamma-Eudesmol | 1209-71-8 | DFHJK |
| 335 | 4,6,6,7,8,8-hexamethyl-1,3,4,6,7,8-hexahydrocyclopenta[g]isochromene | 1222-05-5 | DEFHJK |
| 353 | (Z)-6-ethylideneoctahydro-2H-5,8-methanochromen-2-one | 69486-14-2 | CEFGJK |
| 360 | 8,8-dimethyl-3a,4,5,6,7,7a-hexahydro-1H-4,7-methanoinden-6-yl acetate | 171102-41-3 | DEFHJK |
| 441 | Octahydro-1H-4,7-methanoinden-5-yl acetate | 64001-15-6 | DEFHJKL |
| 484 | 3a,4,5,6,7,7a-hexahydro-1H-4,7-methanoinden-6-yl butyrate | 113889-23-9 | DEFHJK |
| 487 | 3a,4,5,6,7,7a-hexahydro-1H-4,7-methanoinden-5-yl isobutyrate | 67634-20-2 | DEFHJK |
| 488 | Curzerene | 17910-09-7 | DHJK |
| 501 | (E)-cycloheptadec-9-en-1-one | 542-46-1 | DEFGJ |
| 566 | Cedryl formate | 39900-38-4 | BDEFHJK |
| 567 | Cedryl acetate | 77-54-3 | DEFHJK |
| 569 | Cedrol | 77-53-2 | DEFHJK |
| 570 | 5-methyl-1-(2,2,3-trimethylcyclopent-3-en-1-yl)-6-oxabicyclo[3.2.1]octane | 139539-66-5 | DEFHJK |
| 573 | Caryophyllene alcohol acetate | 32214-91-8 | DEFHJK |
| 574 | Caryolan-1-ol | 472-97-9 | DEFHJK |
| 603 | Bornyl isobutyrate | 24717-86-0 | BDEFHIJK |
| 616 | beta-Santalol | 77-42-9 | DEFHJK |
| 621 | beta-Patchoulline | 514-51-2 | BDEFGJKL |
| 624 | beta-Himachalene Oxide | 57819-73-5 | BDFHJK |
| 627 | (2,2-dimethoxyethyl)benzene | 101-48-4 | DHJK |
| 632 | beta-Cedrene | 546-28-1 | BDEFGJKL |
| 663 | Anisyl phenylacetate | 102-17-0 | DFHJ |
| 680 | 2,2,6,7,8,8-heptamethyldecahydro-2H-indeno[4,5-b]furan | 647828-16-8 | ADEFHJK |
| 684 | alpha-Vetivone | 15764-04-2 | DHJK |
| 694 | alpha-Santalol | 115-71-9 | DEFHJK |
| 696 | alpha-Patchoulene | 560-32-7 | ADEFHJKL |
| 708 | alpha-Gurjunene | 489-40-7 | BDEFHJKL |
| 712 | alpha-Eudesmol | 473-16-5 | DEFHJK |
| 714 | alpha-Cubebene | 17699-14-8 | ADEFHJKL |
| 726 | alpha-Agarofuran | 5956-12-7 | BDEFHJK |
| 750 | Allo-aromadendrene | 25246-27-9 | BDEFHJKL |
| 764 | Acetarolle | 744266-61-3 | DFHJK |
| 775 | 7-eip-alpha-Eudesmol | 123123-38-6 | DEFHJK |
| 776 | 7-Acetyl-1,1,3,4,4,6-hexamethyltetralin | 1506-02-1 | DEFHJ |
| 788 | 5-Cyclohexadecenone | 37609-25-9 | DEFGJK |
| 804 | 3-Thujopsanone | 25966-79-4 | BDEFHJK |
| 872 | 10-epi-gamma-Eudesmol | 15051-81-7 | DFHJK |
| 919 | 3a,4,5,6,7,7a-hexahydro-1H-4,7-methanoinden-6-yl propionate | 17511-60-3 | CEFHJK |
| 927 | 5-Acetyl-1,1,2,3,3,6-hexamethylindan | 15323-35-0 | DEFHJK |
| 933 | Patchouli alcohol | 5986-55-0 | DEFHIJK |
| 978 | 3a,4,5,6,7,7a-hexahydro-1H-4,7-methanoinden-6-yl pivalate | 68039-44-1 | DEFHJK |
| 1007 | (2R,4a'R,8a'R)-3,7'-dimethyl-3',4',4a',5',8',8a'-hexahydro-1'H-spiro[oxirane-2,2'-[1,4]methanonaphthalene] | 41816-03-9 | DEFHJK |
| 1022 | 2,2,7,9-tetramethylspiro(5.5)undec-8-en-1-one | 502847-01-0 | DHIJK |
| 1024 | (Z)-2-ethyl-4-(2,2,3-trimethylcyclopent-3-en-1-yl)but-2-en-1-ol | 28219-61-6 | DEFHJK |
| 1027 | 5-methoxyoctahydro-1H-4,7-methanoindene-2-carbaldehyde | 193425-86-4 | CHJK |
| 1029 | Sclareol oxide | 5153-92-4 | DEFHJK |
| 1035 | Spathulenol | 6750-60-3 | DEFHJK |
| 1038 | 1-(spiro[4.5]dec-7-en-7-yl)pent-4-en-1-one | 224031-70-3 | DGJK |
| 1060 | Thujopsene | 470-40-6 | BDEFGJKL |
| 1089 | Tricyclone | 68433-81-8 | DEFHJK |
| 1107 | Valerianol | 20489-45-6 | DEFHJK |
| 1129 | 1-((3R,3aR,7R,8aS)-3,6,8,8-tetramethyl-2,3,4,7,8,8a-hexahydro-1H-3a,7-methanoazulen-5-yl)ethan-1-one | 32388-55-9 | DHJK |
| 1131 | Methyl (Z)-2-(((2,4-dimethylcyclohex-3-en-1-yl)methylene)amino)benzoate | 68738-99-8 | DEFHJ |
| 1136 | Vetivert Acetate | 117-98-6 | DEFHJK |
| 1137 | Decahydro-3H-spiro[furan-2,5'-[4,7]methanoindene] | 68480-11-5 | DEFGJKL |
| 1140 | (1aR,4S,4aS,7R,7aS,7bS)-1,1,4,7-tetramethyldecahydro-1H-cyclopropa[e]azulen-4-ol | 552-02-3 | DEFHJK |
| 1142 | 3,5,5,6,7,8,8-heptamethyl-5,6,7,8-tetrahydronaphthalene-2-carbonitrile | 127459-79-4 | DHJ |
| 1143 | (1S,2S,3S,5R)-2,6,6-trimethylspiro[bicyclo[3.1.1]heptane-3,1'-cyclohexan]-2'-en-4'-one | 133636-82-5 | DEFHJK |
| 1144 | 1',1',5,5'-tetramethylhexahydro-2'H,5'H-spiro[[1,3]dioxolane-2,8'-[2,4a]methanonaphthalene] | 154171-76-3 | DEFHJK |
| 1145 | 1',1',5,5'-tetramethylhexahydro-2'H,5'H-spiro[[1,3]dioxolane-2,8'-[2,4a]methanonaphthalene] K | 154171-77-4 | DEFHJK |
| 1148 | 4,5-epoxy-4,11,11-trimethyl-8-methylenebicyclo(7.2.0)undecane | 1139-30-6 | DEFHJK |
| 1149 | 1,3,4,6,7,8alpha-hexahydro-1,1,5,5-tetramethyl-2H-2,4alpha-methanophtalen-8(5H)-one | 23787-90-8 | DEFHIJK |

TABLE 5

List of materials with ALL MORVs greater than 5 to 10

| Number | Material Name | CAS Number | Comment Code |
|---|---|---|---|
| 248 | Hydroxymethyl isolongifolene | 59056-64-3 | BDEFHJK |

TABLE 6

List of materials with ALL MORVs from 0.5 to less than 1

| Number | Material Name | CAS Number | Comment Code |
|---|---|---|---|
| 472 | Decyl anthranilate | 18189-07-6 | DEFHJ |
| 526 | (Z)-3-methyl-2-(pent-2-en-1-yl)cyclopent-2-en-1-one | 488-10-8 | BCHIJKL |

The materials in Tables 1-6 can be supplied by one or more of the following:
Firmenich Inc. of Plainsboro N.J. USA; International Flavor and Fragrance Inc. New York, N.Y. USA; Takasago Corp. Teterboro, N.J. USA; Symrise Inc. Teterboro, N.J. USA; Sigma-Aldrich/SAFC Inc. Carlsbad, Calif. USA; and Bedoukian Research Inc. Danbury, Conn. USA.

Actual MORV values for each material listed in Tables 1-6 above are as follows:

| Material No. | MORV value for Equation a.) | MORV Value for Equation b.) | MORV Value for Equation c.) | MORV value for Equation d.) |
|---|---|---|---|---|
| 1 | 0.548223914 | 0.876283261 | 1.22018588 | -0.41901144 |
| 2 | 1.520311929 | 3.493450446 | 2.70657265 | 5.11342862 |
| 3 | 2.267801995 | -0.81712657 | 0.43218875 | 1.595983683 |
| 4 | -0.591063369 | -0.48283571 | 0.16199804 | 1.210497701 |
| 7 | 1.437444636 | 2.131822996 | 3.81633465 | 1.318339345 |
| 9 | 2.151445882 | -0.46189495 | 0.56090469 | 1.206360803 |
| 10 | 2.5733592 | -0.58780849 | 1.39751471 | 1.258361591 |
| 11 | 3.052627325 | 1.008519135 | -0.30475953 | 0.076323462 |
| 12 | 0.683776599 | -0.01157903 | 0.82853231 | 0.326169402 |
| 13 | 1.549643217 | 1.809183231 | 0.70864531 | 2.22799611 |
| 14 | 2.82111224 | 2.339505033 | 1.240818 | 2.502429355 |
| 16 | -0.31551128 | -0.06816599 | -0.04371934 | 2.76742389 |
| 17 | -1.334904153 | -0.5773313 | 1.75644798 | 1.898455724 |
| 18 | -1.34154226 | -2.63596666 | 0.06885109 | 1.001431671 |
| 19 | 0.15532384 | 0.09866609 | 0.64214585 | -0.33330779 |
| 20 | 0.640261783 | 0.693213268 | 0.54637273 | -0.97556029 |
| 21 | 0.936895364 | -0.01521118 | 1.1697513 | -0.63510809 |
| 22 | 1.158981042 | 1.115900089 | -0.25859776 | 1.318200884 |
| 23 | 3.702361074 | 1.399942641 | 5.23954766 | 7.089933671 |
| 24 | 0.773874141 | 0.146848137 | -1.05705847 | -0.36193173 |
| 25 | -1.016103969 | -1.18967936 | 0.78064625 | 2.944710012 |
| 25 | -1.016103969 | -1.18967936 | 0.78064625 | 2.944710012 |
| 26 | 0.615085491 | -0.00096877 | -0.35697252 | -0.18121401 |
| 27 | 0.70261974 | -0.22197386 | 0.19710806 | -2.37196477 |
| 28 | 1.366472597 | -0.42546942 | -0.59394241 | -0.01417395 |
| 29 | 1.096043453 | -1.02972898 | -1.42167356 | -0.63817943 |
| 30 | 1.143415203 | -0.85945441 | -0.41416913 | 2.499807942 |
| 31 | 1.138642907 | -0.19595476 | -0.54547769 | -0.98828898 |
| 32 | 1.914414495 | -0.64487788 | 0.63212987 | 1.166699371 |
| 33 | 0.314847366 | 1.848003955 | -1.3905032 | -0.62848261 |
| 34 | -0.113542761 | 0.981530917 | 0.32824239 | 1.126524277 |
| 35 | 0.472382903 | 1.494882467 | -0.07201236 | -0.64589543 |
| 36 | 3.158513795 | 1.084094934 | -0.00328981 | -0.17786385 |
| 37 | -1.055631982 | 2.240172964 | 0.92596118 | 2.105391988 |
| 38 | 3.158513795 | 0.592820874 | -0.49326241 | 0.212867212 |
| 39 | 1.083800659 | 2.069727985 | 2.48170918 | 3.205630609 |
| 42 | -0.103134861 | 0.267726008 | -0.65350189 | 1.125952363 |
| 43 | 0.323961628 | 1.469295081 | -0.52991193 | 0.797908251 |
| 47 | 1.703678841 | 1.348737095 | 2.00634162 | -0.16505407 |
| 48 | 2.370955056 | 2.783472865 | 2.68240273 | 1.221864405 |
| 49 | 1.670680003 | -0.41866107 | -0.9173849 | 1.181929544 |
| 50 | 1.670680003 | 0.076369374 | -0.49915943 | -0.85392575 |
| 52 | 0.464485039 | 0.057512869 | 1.31230219 | -0.11170276 |
| 53 | 0.626671823 | -0.46954947 | -0.33383736 | 0.277079201 |
| 54 | 0.666149043 | 0.009549925 | -0.36226343 | 0.197224432 |
| 55 | 0.723473579 | -1.50916383 | -0.3848989 | -0.71458778 |
| 57 | 0.381273227 | 1.192994109 | 1.65593321 | -1.65739236 |
| 59 | 0.561360663 | -0.17793966 | -1.63250554 | -0.7564969 |
| 61 | 0.146473611 | -0.01535544 | -0.16339658 | 1.738656146 |
| 62 | 1.20162032 | -0.3576095 | -0.10695443 | 1.322155191 |
| 63 | 1.084291915 | 2.258720158 | -1.01245416 | 1.688283974 |
| 64 | 0.744770665 | 0.155243763 | -1.8029919 | 1.023503542 |
| 65 | 0.972835178 | 2.797151284 | 1.53453579 | 0.857051645 |
| 67 | 2.069410561 | 0.021831924 | 0.37855159 | -0.67235457 |
| 68 | 0.527636614 | 0.590831983 | 1.02843762 | 2.208655795 |
| 69 | 2.133965691 | 2.088998449 | 2.05751412 | -0.9433713 |
| 70 | 0.327378959 | 0.996844599 | 1.23648533 | -1.25138371 |
| 71 | 1.40093669 | 0.778222691 | 0.70401172 | -0.24075444 |
| 72 | 0.617697349 | -0.29503359 | 0.52404847 | 0.816184656 |
| 73 | 0.617792473 | 0.888976061 | -0.45289639 | 0.615659244 |
| 74 | 1.437359024 | 1.548292147 | 0.10314807 | -0.48982286 |
| 75 | -1.970885622 | 3.398008325 | 4.08025266 | -0.89948156 |
| 76 | -1.32746934 | -2.65365233 | 0.10272816 | 1.001614125 |
| 77 | -2.541686116 | 3.295534192 | 3.75284227 | 0.404837808 |
| 78 | -2.110794 | 2.109874746 | 3.13350902 | -0.3880285 |
| 79 | 1.641162056 | -0.28533994 | 1.53676145 | 0.652696023 |
| 80 | 1.594400214 | 0.283682865 | 2.23140233 | 1.111682021 |
| 81 | 0.176566806 | -2.0786518 | -2.13986952 | 0.981126964 |
| 82 | 0.980373758 | -0.28813159 | 0.19404501 | 1.252564677 |
| 83 | 0.941833098 | 0.317310013 | 1.17606727 | 0.72992237 |
| 84 | 0.774237336 | -0.27140727 | 0.72461427 | -1.56415746 |
| 85 | 2.092976965 | 0.810644229 | 0.82999192 | -0.62861806 |
| 91 | 2.061595915 | -0.79930338 | -0.18285395 | -0.66898499 |
| 92 | 2.068748434 | -0.24299896 | 0.07214682 | -1.11758276 |
| 93 | -0.08984279 | -1.06025959 | -0.05068694 | 1.560050105 |
| 96 | 0.927758203 | -0.44129515 | 0.89190422 | 0.744284978 |
| 97 | 0.658667572 | -0.68771072 | 0.46051026 | -0.53120883 |
| 98 | 0.853222693 | -0.2037738 | -0.21414441 | 1.119784962 |
| 100 | 1.654535066 | 0.995056228 | 2.35139085 | 0.543654824 |
| 101 | 2.173663649 | -0.11491477 | 1.48285148 | 1.698527571 |
| 102 | 2.066679492 | -0.16785146 | -0.84780149 | 0.12159477 |
| 103 | 2.335152618 | -0.02866585 | 0.16993375 | -0.98254522 |
| 104 | 2.760588276 | 0.459513599 | 1.35310241 | 0.000336976 |
| 105 | 1.654535066 | 3.654489674 | 3.13033965 | 0.544225478 |
| 106 | 1.750588169 | -0.55853348 | 0.50257773 | 1.630011313 |
| 107 | 0.896789863 | 0.73615897 | 0.53011623 | -0.54697747 |
| 108 | 0.532375207 | 0.826537134 | 1.21040312 | 0.690230716 |
| 109 | 2.407655187 | 0.742651426 | 1.80322099 | 0.271832856 |
| 110 | 0.54830833 | 2.916795026 | 1.40126098 | 0.690230716 |
| 111 | 0.939597126 | -0.3750368 | -1.23479972 | -0.89366351 |
| 112 | 1.398518854 | 1.265740274 | 4.19618377 | -0.12762692 |
| 113 | 1.415726941 | 0.086297006 | 3.43559555 | -0.12964168 |
| 115 | -1.557729423 | -0.44113526 | 0.86330536 | 0.590708892 |
| 116 | 0.193562268 | -1.58091165 | 0.83247813 | -0.70978039 |
| 117 | 1.353510875 | -0.59062398 | -0.31776345 | -0.3050158 |
| 119 | 0.830052725 | 2.28725579 | 0.38409695 | 0.219336109 |
| 120 | 1.261997955 | -0.22622961 | -1.04772194 | 2.028504137 |
| 122 | 1.505653628 | -1.14748206 | -0.19760084 | -0.81373045 |
| 123 | -0.658721962 | -0.21299878 | 1.01439841 | -0.76731016 |
| 125 | 0.749676998 | -1.0761601 | 0.99563924 | -1.15409002 |
| 126 | 0.931054384 | -0.35067079 | 1.06050832 | -1.62171794 |
| 128 | -1.344832644 | -0.09451199 | 1.19145467 | 1.621274257 |
| 130 | 1.153249538 | 1.605070708 | 2.38047907 | -0.93842293 |
| 133 | 0.840066046 | 0.2323025 | 0.19054023 | -0.26588341 |
| 134 | 0.522267541 | 0.824106618 | 1.83479545 | 0.364403434 |
| 135 | 2.142817887 | 2.142411243 | -0.93830995 | 0.696522652 |
| 137 | 3.052627325 | 3.606270166 | 0.50445208 | 0.076323462 |
| 140 | -0.153437637 | 0.246303216 | 0.76565758 | 1.800968868 |
| 141 | 2.067620311 | 1.424830396 | 2.33536931 | 7.644025075 |
| 142 | 0.98353103 | 1.950251373 | 2.50851828 | -0.24499521 |
| 143 | 1.736969725 | 0.991537809 | 2.5691601 | 1.227191656 |
| 145 | -0.211768579 | 1.46336231 | -0.93580247 | -1.48749449 |
| 146 | 1.912710035 | 0.926306508 | 1.81253333 | 0.494121361 |
| 147 | 0.675736703 | 0.99203385 | -0.66034472 | -0.66302669 |
| 148 | 0.757176542 | 1.83006252 | 0.16210659 | 0.243674851 |
| 149 | 0.438772371 | 1.091438092 | -0.1560319 | -0.61711642 |
| 150 | 0.84399938 | 0.675302022 | -1.69771411 | -0.73841711 |
| 151 | 0.633570539 | 0.988413715 | -0.54991825 | -0.43550324 |
| 152 | 0.911582356 | 1.974700218 | -0.92267786 | 0.628660087 |
| 153 | 0.319053885 | 2.531735341 | -0.39139184 | 0.734629224 |
| 154 | 0.714814512 | 0.690769753 | -2.06588692 | -0.73356628 |
| 155 | -0.161798388 | 0.032135767 | -0.13802086 | 1.734928461 |
| 156 | -0.571799976 | -1.32834264 | -1.65346017 | 1.856689553 |
| 157 | 0.131224024 | 0.21510779 | -1.70996346 | 0.964902175 |
| 158 | 1.201616145 | -0.21158932 | -0.8501176 | -0.33330779 |
| 159 | 0.811289908 | 1.606645397 | 0.25352447 | -1.83775117 |
| 159 | 0.811289908 | 1.606645397 | 0.25352447 | -1.83775117 |
| 161 | 0.475184006 | 1.99305646 | 1.90910177 | 3.288337059 |

| Material No. | MORV value for Equation a.) | MORV Value for Equation b.) | MORV Value for Equation c.) | MORV value for Equation d.) |
|---|---|---|---|---|
| 162 | 0.833030517 | 0.487189028 | 1.76798642 | 0.104378164 |
| 163 | 0.58993703 | −0.46431772 | 0.74883588 | −0.81090824 |
| 166 | −0.121286831 | −0.84664528 | −0.32625341 | 0.778055656 |
| 167 | 0.846400186 | −0.25922232 | 0.69248774 | 1.183696217 |
| 168 | −0.310930833 | −0.81048493 | 0.08527131 | 1.61831109 |
| 169 | −0.2346025 | 0.890438419 | −0.13206526 | −0.83961838 |
| 170 | −0.169223695 | 1.172917966 | −0.11306441 | 0.099121666 |
| 174 | 2.863652137 | 0.236674094 | −0.69038707 | 1.610215283 |
| 175 | 1.789769228 | −0.31740428 | −0.89529921 | −0.09686469 |
| 176 | 2.625947334 | 0.083548191 | 0.30634559 | −0.35925728 |
| 177 | 1.674319352 | −0.22179044 | 0.42093738 | −0.23683577 |
| 178 | 2.863652137 | 0.727069168 | −0.26724686 | −0.44888613 |
| 179 | 0.070511885 | 0.365852864 | 1.35327505 | −0.03748038 |
| 181 | 0.976254543 | 0.691638796 | 0.51371978 | −0.02503945 |
| 182 | −1.842503751 | −0.12688474 | 2.56277877 | 0.111744488 |
| 183 | 3.195758563 | 3.886545621 | 4.29482769 | 3.829845293 |
| 184 | 0.333889534 | −0.67236766 | 2.21605977 | 4.254612125 |
| 185 | 5.61162203 | 1.40458529 | 2.86231343 | 1.035135749 |
| 186 | 1.068190511 | −0.65969343 | −0.63104765 | −1.36962992 |
| 187 | 1.396358739 | 0.249705611 | 0.81449499 | −0.15353102 |
| 189 | 1.544466636 | −0.33742685 | 0.8096674 | −0.44483677 |
| 190 | −0.210918777 | −1.04086063 | 0.02614862 | 3.362615492 |
| 191 | 0.715897301 | 0.666316436 | −0.41719538 | 0.400723176 |
| 192 | 0.65612864 | 1.231196814 | 0.75462061 | 1.514581532 |
| 193 | −0.394884432 | 1.129269425 | −0.3157071 | −0.61478944 |
| 194 | −2.111794245 | −0.71010521 | 0.53077207 | 0.59302222 |
| 195 | 1.18880856 | 0.704463775 | 1.99312777 | 1.419709023 |
| 196 | 1.885714606 | 0.436434665 | 1.44657532 | 1.145809063 |
| 197 | 2.174580668 | 0.133070149 | 0.99814905 | 0.871658496 |
| 198 | −0.533922573 | −2.16213117 | 0.5812107 | −0.92280453 |
| 199 | 1.493919434 | 1.45125612 | 1.95141371 | 4.403441058 |
| 201 | −0.005520296 | −0.83362523 | 0.65480762 | −0.38894276 |
| 204 | 0.732981164 | −0.97494758 | −0.91192246 | −1.00034323 |
| 205 | 0.991838899 | −0.60053505 | −0.49983634 | 0.674468753 |
| 206 | 2.147983695 | 1.291351958 | 1.64553247 | 1.626455601 |
| 208 | −0.386224123 | −0.24799559 | 1.19406353 | −1.61243489 |
| 209 | 1.447075297 | 0.122626462 | 1.08021156 | 0.473154634 |
| 210 | −0.386224123 | −0.24799559 | 1.19406353 | −1.61243489 |
| 211 | 2.186118467 | 1.873949371 | 0.64852028 | −0.59205851 |
| 212 | 1.367811201 | 1.689658923 | 1.8017376 | 2.525531645 |
| 213 | 0.925016223 | 0.875610609 | 0.31462609 | 0.847028648 |
| 214 | −0.239873321 | 1.808823425 | −0.36105512 | −0.07650286 |
| 215 | 2.264275088 | 3.25759951 | 3.25749282 | 2.147928282 |
| 218 | −0.509585598 | −0.93428643 | 1.63030386 | −0.79436377 |
| 221 | 1.876297063 | 0.026873469 | 0.45442758 | 1.538486988 |
| 227 | 5.317676982 | 2.824566654 | 1.73360625 | 3.103310061 |
| 228 | 3.323728685 | 1.554268023 | 1.8883835 | 0.957527434 |
| 229 | 3.218950175 | 1.464118271 | 2.47512497 | 1.214429025 |
| 230 | 5.242356467 | 3.482206715 | 3.50441556 | 1.614847073 |
| 230 | 5.242356467 | 3.482206715 | 3.50441556 | 1.614847073 |
| 231 | 2.710087358 | 1.517756148 | 0.35088855 | 0.603171932 |
| 231 | 2.710087358 | 1.517756148 | 0.35088855 | 0.603171932 |
| 232 | 0.703604481 | 0.42129186 | 0.39567696 | 0.41729786 |
| 233 | 1.312921486 | 0.816597603 | 2.17066283 | 0.472801294 |
| 234 | 0.874145958 | 0.741410502 | 1.71105753 | −0.47289453 |
| 237 | 0.778921491 | −1.02119303 | 0.4612164 | −0.8881184 |
| 238 | 0.681403734 | −0.342052 | 1.27750286 | −0.3383341 |
| 239 | −0.870637933 | −2.58292907 | 0.79173772 | −1.27888846 |
| 242 | 0.910211214 | 0.374558101 | 1.01712695 | 1.001043471 |
| 243 | 1.670680003 | 0.104780951 | −0.6545574 | −0.46985154 |
| 244 | 1.140332181 | 0.116513028 | 1.61110902 | 3.713305291 |
| 246 | −0.634992987 | 0.548746912 | 4.62542427 | 7.660969857 |
| 247 | −1.739729444 | −0.91508372 | 1.18693162 | 3.108631198 |
| 248 | 5.81821686 | 6.320330685 | 6.14379552 | 5.214046447 |
| 249 | 0.348188924 | −0.95333461 | −0.08432225 | 1.866717393 |
| 252 | 2.456287983 | −0.02516176 | 0.76814124 | 1.756087132 |
| 253 | 1.76915226 | 0.226389981 | −0.18115009 | −0.62385199 |
| 254 | 0.658956861 | −0.39322197 | −0.67153044 | 1.416053304 |
| 255 | 0.892122738 | −0.46985009 | 0.42813903 | −0.46752753 |
| 256 | 0.625043963 | −0.65111806 | 1.4319541 | 2.110656697 |
| 258 | −0.187789327 | −0.85870492 | −0.21766971 | 0.931521178 |
| 259 | −1.261365139 | −2.33099427 | 1.33595129 | 0.43644676 |
| 260 | 2.4020693 | 2.669351733 | 2.36395771 | 1.910609499 |
| 261 | 1.978618006 | 2.732613301 | 2.19594212 | 1.683156477 |
| 263 | 1.350274014 | −0.59210334 | 0.14780643 | −0.13113746 |
| 264 | 0.526085484 | −1.54983116 | −0.17497208 | −0.8204696 |
| 267 | 1.175997006 | −1.03507906 | −0.11004734 | −0.50564806 |
| 269 | 2.367197222 | 0.457286256 | 0.02211231 | 0.497925297 |
| 270 | 0.711734628 | −1.45058685 | −0.17018094 | −0.71795736 |
| 271 | 1.073564668 | −0.47951936 | −0.80269361 | 0.136837431 |
| 273 | 0.663835001 | −1.5674675 | 0.28509522 | −1.12959038 |
| 274 | 1.628173498 | −0.58892922 | −0.3892777 | −0.66728139 |
| 275 | 0.935336765 | −0.9522644 | −0.87000279 | −0.29365972 |
| 276 | −5.989155804 | 1.722071272 | 3.31094703 | 1.273171428 |
| 277 | 0.904631703 | −1.02628534 | 0.49274649 | 1.000655271 |
| 278 | 0.293923493 | −0.82335619 | 0.13147975 | 2.730914048 |
| 280 | −0.284822555 | 0.322094188 | 3.2184015 | 0.383213731 |
| 281 | 2.201373139 | 2.228820089 | 2.03455575 | 1.720697243 |
| 282 | 0.505189899 | −1.01844885 | −0.98499144 | 0.912195522 |
| 283 | 0.775002479 | −1.29876341 | −1.52162214 | −0.77292581 |
| 284 | 0.505189899 | −0.57830662 | −0.55673047 | −1.09870665 |
| 285 | −0.987611415 | 0.908212704 | 2.59089199 | 1.311154128 |
| 286 | −2.635687733 | −1.53554173 | 0.68132558 | 4.350511118 |
| 287 | −1.890800496 | −0.9175912 | −0.84177071 | 0.615422874 |
| 288 | −0.417807714 | −0.27643667 | 1.06515025 | 0.958812195 |
| 289 | 1.078763544 | 0.263281029 | 1.00763749 | 0.866949263 |
| 290 | 0.733561298 | −0.47493387 | 0.17088582 | 1.536463653 |
| 292 | 1.2252731 | 0.720498276 | 4.33362953 | 2.202084022 |
| 293 | 0.947860369 | 0.93449449 | 1.85056304 | 0.355024738 |
| 294 | −1.051634009 | 0.136579632 | 2.17918871 | −0.01949057 |
| 295 | 1.039790111 | 0.81471915 | −0.94326824 | 0.887662055 |
| 296 | 1.009509413 | 1.364418947 | 1.42805339 | 0.429992055 |
| 300 | 0.246930208 | 1.113809101 | 0.25540773 | 0.528760053 |
| 301 | 0.246930208 | 1.113809101 | 0.25540773 | 0.528760053 |
| 302 | 0.697198045 | −0.41506076 | −2.35076003 | −0.60639529 |
| 303 | 0.10667178 | 3.580489288 | 0.25893587 | 2.329367856 |
| 306 | 0.561360663 | −0.17793966 | −1.63250554 | −0.7564969 |
| 307 | 1.583243229 | 1.398558046 | 0.152423 | −0.13988304 |
| 308 | −0.067380931 | 0.74278658 | 0.29217479 | 0.180866298 |
| 310 | 0.238202662 | 0.926241567 | −0.66649303 | 0.508184193 |
| 312 | 0.714965519 | −0.45511207 | −2.34849436 | −0.9953911 |
| 314 | 0.736369931 | −0.52068396 | 0.53882253 | −0.7059813 |
| 316 | 2.314558863 | −0.25458611 | 0.22080129 | −0.04142716 |
| 317 | 1.095005005 | 0.057439852 | −1.20728654 | 0.035895107 |
| 318 | −0.111714595 | −0.61079351 | −1.16010053 | 1.102488007 |
| 319 | −0.264829849 | 0.540388888 | 0.10729709 | −0.57215449 |
| 321 | 1.243861203 | −0.75229123 | 0.05515858 | −0.34659253 |
| 322 | 0.956379568 | 2.838565742 | 2.7997689 | 0.805938034 |
| 323 | 1.884902746 | 0.813499245 | 0.86344403 | −0.1241887 |
| 324 | 0.189037208 | 1.105600415 | 0.48460989 | 0.285938173 |
| 325 | 0.791400443 | 2.454239197 | 1.54315324 | 1.416449646 |
| 328 | 1.22836182 | 2.190068443 | 2.48751772 | 0.126982574 |
| 329 | 1.800767509 | 1.372656013 | 2.09551175 | 2.849728342 |
| 330 | 2.688999059 | 0.017422444 | 0.34929031 | 0.108155361 |
| 331 | −0.223648429 | 0.873635097 | 1.78683863 | 0.126324441 |
| 332 | 1.884902746 | −0.46695445 | 0.1761545 | −0.11026722 |
| 333 | 0.956379568 | 2.838565742 | 2.7997689 | 0.805938034 |
| 334 | 0.569368001 | 2.811464091 | 1.88866785 | −0.16122533 |
| 335 | 1.931053264 | 2.306571877 | 4.45651797 | 4.474221307 |
| 336 | 1.355107839 | −0.49142588 | 0.83879083 | 0.18350392 |
| 338 | 1.025467157 | −0.99345477 | 0.57780149 | −0.19101275 |
| 339 | 1.216559787 | −0.68632827 | 0.71921804 | 0.140021721 |
| 342 | 2.073599715 | −0.19777074 | −0.44964804 | −0.71885866 |
| 343 | 3.375840967 | 3.294907583 | 5.0378352 | 4.148045911 |
| 344 | 0.926453735 | 1.336260845 | 2.20088072 | 0.226359561 |
| 346 | −0.133453942 | −0.27276578 | 0.95852923 | −0.88404805 |
| 347 | −0.414858428 | −0.94736055 | 1.9452074 | −1.32753709 |
| 349 | 0.011110326 | 0.415952358 | 1.08076289 | 2.638925816 |
| 350 | −1.366284031 | −1.3912958 | −0.0683659 | 1.205395618 |
| 352 | 2.592229701 | 2.014162407 | −0.56599991 | −0.19676404 |
| 353 | 2.347680291 | 1.432589328 | 3.81650185 | 2.28664738 |
| 354 | −0.094599823 | 0.704257624 | 0.8494127 | −0.05632553 |
| 355 | −0.534528735 | −0.26820008 | 0.69328667 | 0.63557685 |
| 356 | 0.71431796 | 0.568464069 | 1.14931631 | 0.32594963 |
| 358 | 1.637857828 | 1.932629993 | 0.68535871 | −1.06298922 |
| 359 | 3.169264285 | 2.326146291 | 5.44251947 | 3.621423972 |
| 360 | 2.824830639 | 3.29829616 | 3.43870859 | 3.771256974 |
| 361 | 0.772183137 | 0.62924397 | 1.14549597 | 0.743423792 |
| 362 | 2.158106604 | −0.08901432 | 0.85035629 | −0.37323677 |
| 363 | 1.485114303 | −0.85819594 | 0.70929196 | 4.132013298 |

| Material No. | MORV value for Equation a.) | MORV Value for Equation b.) | MORV Value for Equation c.) | MORV value for Equation d.) | Material No. | MORV value for Equation a.) | MORV Value for Equation b.) | MORV Value for Equation c.) | MORV value for Equation d.) |
|---|---|---|---|---|---|---|---|---|---|
| 364 | −0.661168364 | −0.30270875 | 2.49237859 | −0.7675819 | 472 | 0.605628283 | 0.938001104 | 0.50028363 | 0.743911872 |
| 365 | −0.518303431 | −2.08665423 | 0.5658944 | −1.10451499 | 473 | 0.093847515 | −1.1973016 | −0.26960381 | 1.829684619 |
| 366 | −0.501301831 | 0.561788544 | 0.14113617 | 0.610082057 | 474 | 0.696773849 | 1.065592689 | 0.37607733 | −0.19214193 |
| 368 | −0.106125097 | 1.092782715 | −0.89571841 | −0.08594454 | 475 | 1.405352842 | 0.379589036 | 0.27781476 | 0.041425889 |
| 369 | 1.43532227 | 1.656262941 | −1.09448841 | 1.674272267 | 477 | 0.237582954 | 0.629327199 | 0.45159895 | −1.59912382 |
| 370 | 1.064083705 | −1.08482967 | 0.35640283 | 0.866246621 | 478 | 1.360648836 | 0.598053217 | 2.00883441 | −0.0827715 |
| 371 | 1.933819902 | 0.975863726 | 1.62799441 | 1.492919426 | 479 | 2.214928637 | −0.24358938 | −0.3486103 | 0.9190125 |
| 372 | 1.933819902 | 0.975863726 | 1.62799441 | 1.492919426 | 480 | 1.933819902 | −0.3826187 | 0.97439148 | 1.491603428 |
| 373 | 0.274120553 | 2.246646022 | 2.93946992 | 2.617412085 | 480 | 1.933819902 | −0.3826187 | 0.97439148 | 1.491603428 |
| 374 | 0.940949346 | 2.935858163 | 0.52084392 | 0.847114052 | 481 | 0.612364301 | −0.26364231 | −1.3201026 | −1.62884377 |
| 375 | 0.177236108 | 2.745061961 | 0.76268843 | 0.373809692 | 482 | 1.604448424 | 1.286308964 | −0.34289284 | 0.887781648 |
| 376 | −0.999571921 | 0.579320229 | −0.06019938 | −0.94280945 | 482 | 1.604448424 | 1.286308964 | −0.34289284 | 0.887781648 |
| 377 | 0.521811983 | −0.8476641 | 0.7732377 | 1.729460647 | 484 | 3.269313083 | 2.336715633 | 3.65534824 | 2.158890088 |
| 378 | −0.532701772 | −2.17823188 | 1.26760147 | 0.815211357 | 486 | 1.530484593 | 1.052491466 | 3.11297562 | 0.430146348 |
| 379 | −0.684994963 | 0.018353057 | −0.8170018 | 0.582030709 | 487 | 2.889323404 | 2.226094104 | 4.12877599 | 2.184426542 |
| 381 | 1.592237677 | 1.373054134 | 0.60184939 | −0.30300485 | 488 | 1.062548487 | 4.75312035 | 2.78435853 | 2.01925207 |
| 385 | 0.967501839 | 0.136172137 | 1.3645564 | 0.374341215 | 491 | 0.397432667 | −0.20071274 | 0.842202 | 1.944142408 |
| 385 | 0.967501839 | 0.136172137 | 1.3645564 | 0.374341215 | 493 | 0.270731661 | −0.7406408 | −1.17192239 | 1.401933582 |
| 386 | 1.247138794 | −0.97883463 | 0.03688288 | −0.57321578 | 495 | 0.298981649 | 0.854414067 | −2.2714622 | −0.62848261 |
| 387 | 0.785485559 | −1.23629818 | −0.07759084 | −0.71795736 | 496 | 0.565278409 | 0.659352661 | −0.00159534 | 0.384991859 |
| 388 | 1.503632155 | −0.13455265 | 0.86630165 | 0.102845335 | 497 | 2.972647554 | 1.210988046 | 0.08629653 | 0.991649406 |
| 388 | 1.503632155 | −0.13455265 | 0.86630165 | 0.102845335 | 498 | 2.863652137 | 0.229707592 | −0.75515466 | −0.06022029 |
| 390 | 0.811363694 | 0.872605919 | −0.17445198 | 1.358866557 | 502 | 0.478208715 | 1.827989577 | 0.67676345 | −0.88328385 |
| 391 | 1.653006495 | −0.44095837 | 0.46475017 | −0.16817306 | 503 | 0.845706083 | 1.117392544 | −0.21773539 | 0.272770415 |
| 394 | 1.043989895 | −0.82625074 | 0.40893134 | −0.10417542 | 504 | 0.837488879 | 0.874463134 | −0.08311625 | 0.149327397 |
| 397 | 1.430046723 | −0.79407262 | 0.15684862 | −0.4384694 | 505 | 1.749446006 | 0.076054765 | −0.59137073 | 0.291488011 |
| 398 | −1.401723491 | 0.271079592 | 1.35530191 | −0.63550333 | 509 | 0.716903285 | −0.22917288 | −1.93027881 | −1.52173529 |
| 400 | 0.762211626 | −1.06778628 | −0.93642574 | −0.13193338 | 510 | 0.241638743 | 0.769444787 | −0.07283731 | −0.38771737 |
| 407 | 0.591198428 | −0.8943503 | 1.41392426 | 2.694863328 | 512 | 0.556069536 | −0.47514685 | −1.88388474 | −1.67297277 |
| 412 | −0.067309295 | −0.21963004 | 0.57788677 | −1.22740308 | 515 | 0.23291131 | 0.598998195 | −0.99553291 | −0.40829542 |
| 413 | 0.630456164 | 1.538096427 | 2.10994563 | 2.45668637 | 517 | 0.784181146 | −0.20530019 | −1.89414748 | 0.152726109 |
| 414 | 0.460631327 | 3.678501689 | 1.18326431 | 1.28320952 | 518 | 0.742030255 | 0.281479436 | −1.4156326 | −1.91369695 |
| 415 | 0.060485009 | −1.37776759 | −0.22689728 | 2.328813337 | 519 | 0.367442761 | −0.50911405 | −0.77651804 | 3.081125259 |
| 416 | 1.864088631 | 0.2451067 | 1.63260125 | 1.855346924 | 520 | 1.28335174 | −0.16976166 | 0.19676128 | 1.493753388 |
| 417 | −0.747017264 | −2.60335412 | 0.85092701 | 3.525229717 | 521 | −1.105672292 | −1.29204085 | −0.95149628 | 1.817322011 |
| 418 | 3.678359573 | 3.437930194 | 4.42449746 | 0.716864637 | 522 | 0.714965519 | −0.45511207 | −2.34849436 | −0.9953911 |
| 419 | −0.131519393 | 0.731836014 | 0.81604919 | −1.29993979 | 524 | 0.325255266 | 1.131242708 | −2.79377204 | −0.62848261 |
| 420 | 0.11276779 | −0.13029453 | 0.19422843 | 0.853490939 | 525 | −0.210625832 | 0.979060885 | 0.37926876 | −2.08002977 |
| 421 | 2.819997124 | 0.193567405 | 1.15903162 | 1.748390255 | 526 | 0.698504484 | 0.548193178 | 0.92265651 | 0.500152973 |
| 424 | −0.211768579 | 1.46336231 | −0.93580247 | −1.48749449 | 527 | 0.420012766 | 1.731459464 | −0.23341719 | 0.139565409 |
| 425 | −1.467980751 | −2.41196874 | −0.34454968 | 2.161517022 | 528 | 0.161304111 | 0.66712144 | 0.58401752 | 0.373809692 |
| 426 | 2.176374648 | 2.131594325 | 1.99252316 | 0.002774099 | 529 | 0.911890585 | 0.353572744 | 1.04706167 | 1.001090055 |
| 428 | 2.10568799 | 0.336366154 | −1.41176883 | 0.827982605 | 530 | 1.670680003 | 0.86138741 | −0.27652639 | 1.174059185 |
| 429 | 2.179080731 | 0.811454228 | −0.58304782 | 0.827982605 | 531 | −0.169223695 | 1.172917966 | −0.11306441 | 0.099121666 |
| 432 | 0.814675557 | −0.13076033 | 1.07380397 | −0.01560954 | 532 | 2.237616041 | 1.438074134 | 0.31117554 | −0.71786492 |
| 436 | 0.003614069 | −0.4704298 | 1.6004974 | −1.27605297 | 534 | 1.205873658 | 1.32208026 | 1.21816392 | −0.5027271 |
| 437 | −0.070955783 | −0.17246926 | 0.32599434 | 0.682083059 | 535 | 0.999469738 | 0.056406435 | 0.72382479 | −0.61170287 |
| 438 | 0.71141055 | −0.62729405 | 0.6220964 | 0.498836975 | 536 | 0.63876931 | −0.39111525 | 0.08747854 | −0.66833729 |
| 439 | −2.152188932 | −1.81662702 | 0.66042162 | −1.57001886 | 537 | 0.689953348 | 1.206425159 | 0.58870271 | 0.198159994 |
| 440 | 0.194444196 | 0.880854446 | 0.80016905 | 0.373809692 | 538 | 0.54988634 | −0.32842011 | 0.69258273 | −0.81953404 |
| 441 | 2.349282571 | 1.734747324 | 1.71148239 | 1.274963632 | 540 | 0.735538933 | −0.20826876 | 0.6955468 | −0.7170218 |
| 442 | 0.243841724 | 0.036287037 | 0.51243015 | 0.361825534 | 541 | 1.097368973 | 0.740159871 | 0.12012053 | 0.137772993 |
| 443 | −0.131519393 | 0.731836014 | 0.81604919 | −1.29993979 | 542 | −0.24632881 | −0.09354384 | −0.13580399 | 0.599029186 |
| 444 | 0.607958335 | 1.910541857 | −0.42710132 | −0.46909656 | 544 | 0.687639306 | −0.30861817 | 1.14537443 | −1.12865481 |
| 445 | −0.047486491 | 1.045012945 | −0.25220201 | −0.31982826 | 546 | 1.670680003 | 1.94609957 | 0.19633838 | 1.14825764 |
| 447 | 0.611981677 | 0.559261438 | −0.31210071 | −2.20421695 | 547 | −0.24632881 | −0.23975349 | −0.01449288 | 0.574861147 |
| 448 | 0.45491409 | 0.804084437 | 0.03088748 | −0.17549737 | 548 | 1.349418105 | −0.29885837 | 0.42849141 | 0.008671721 |
| 449 | 0.323968221 | −1.00428076 | −1.65151616 | 1.031096548 | 549 | 0.623933699 | −0.62776258 | −1.2835205 | −0.23131507 |
| 450 | 1.433196296 | −0.12277841 | 3.46809784 | −0.14760118 | 550 | 1.091300413 | −0.33969057 | 0.91994098 | 0.043900994 |
| 453 | 1.138642907 | 0.238344138 | −0.56453732 | −0.60639529 | 550 | 1.091300413 | −0.33969057 | 0.91994098 | 0.043900994 |
| 454 | 0.689556954 | −0.32116049 | 0.17614165 | 0.99165159 | 551 | 1.172668936 | −0.39476924 | −0.61394794 | −0.16425167 |
| 455 | −0.978653338 | −0.96381951 | 0.37950282 | 0.793341469 | 552 | 1.434150355 | 1.041294025 | 0.32000606 | 1.24279868 |
| 457 | 2.740852074 | 1.146976436 | 0.01429902 | 0.909817098 | 553 | 1.040907688 | −0.38050079 | −0.95306497 | −0.03036668 |
| 459 | 2.034203389 | −0.06483391 | 0.25864307 | 0.096715771 | 554 | 0.623933699 | −0.65991007 | −1.27562979 | −0.61529805 |
| 461 | 0.405441454 | 3.029508918 | 1.66201629 | 0.621375526 | 555 | 0.623933699 | −0.09654208 | −0.6432411 | 1.36608372 |
| 462 | 1.348588872 | 2.252065606 | 1.98535615 | 0.126982574 | 556 | 0.623933699 | −0.62776258 | −1.2835205 | −0.23131507 |
| 463 | 2.402548765 | 0.141297665 | 0.32401564 | 0.165555831 | 557 | −1.043779684 | 0.358151507 | 0.96578333 | −0.7498558 |
| 464 | 1.396358739 | −0.35292634 | 0.11760582 | −0.13960954 | 558 | 3.113548387 | 0.901949497 | −0.07402944 | 2.171129217 |
| 465 | 0.940569103 | 1.267891616 | 1.68420132 | 1.263608034 | 559 | 1.433732801 | 2.854621121 | 1.81079379 | 0.893806123 |
| 466 | −0.191220659 | 0.067062979 | 2.24237992 | 0.125280183 | 560 | 0.793851811 | 0.195900744 | 1.13222828 | −0.38432626 |
| 467 | 0.940569103 | 1.267891616 | 1.68420132 | 1.263608034 | 561 | 1.874725149 | 0.921395625 | 3.05642524 | 2.616508159 |
| 468 | 0.123370943 | 1.164309475 | 0.17099727 | −0.95446701 | 562 | −1.30410643 | −2.63450231 | 0.12574616 | 1.001870337 |
| 469 | 0.925252053 | −0.57178441 | 0.69807561 | −0.59133195 | 563 | −0.153585698 | 2.733591064 | 2.12854196 | 3.424603045 |
| 470 | 2.237616041 | 1.810156128 | −0.58140154 | 1.320304914 | 565 | 3.655479783 | 3.751479035 | 5.51820797 | 3.282822615 |
| 471 | 1.714516544 | −0.62135116 | 0.23636624 | −0.2706853 | 566 | 4.034374094 | 3.755759834 | 4.82506006 | 3.190861648 |

| Material No. | MORV value for Equation a.) | MORV Value for Equation b.) | MORV Value for Equation c.) | MORV value for Equation d.) | Material No. | MORV value for Equation a.) | MORV Value for Equation b.) | MORV Value for Equation c.) | MORV value for Equation d.) |
| --- | --- | --- | --- | --- | --- | --- | --- | --- | --- |
| 567 | 4.203811008 | 3.627632534 | 4.68751919 | 3.372829008 | 660 | 2.175041013 | 1.882945358 | 0.07779745 | −0.18323732 |
| 568 | 1.643514525 | 0.827299302 | 0.70706274 | 2.545428997 | 661 | −0.316755016 | 1.64607349 | 2.76327471 | 2.024910676 |
| 569 | 2.692371513 | 3.589810155 | 4.40390088 | 4.506937878 | 662 | 0.258228842 | 0.844792644 | 0.1924797 | 0.098776211 |
| 570 | 1.707556133 | 2.400065573 | 1.78745169 | 2.655458557 | 663 | 1.521826905 | 1.097809988 | 2.13583044 | 1.30609234 |
| 571 | 1.862893827 | 2.803280605 | 0.98209954 | 3.188564781 | 664 | 0.708920214 | −0.27795513 | 0.15395433 | 0.014791904 |
| 572 | 1.203581368 | 0.798608763 | 2.67898788 | 1.659633314 | 665 | 0.630772742 | −0.34278374 | 0.49097281 | −0.0565644 |
| 573 | 2.459623568 | 2.656773866 | 3.54771795 | 2.085649266 | 667 | 0.812238101 | 0.195908668 | 0.21564664 | 0.219336109 |
| 574 | 2.878405284 | 1.770500246 | 4.00464111 | 4.859737959 | 668 | 1.529097453 | 2.246515706 | 1.4678099 | −0.81836944 |
| 575 | −0.395731956 | 0.325594009 | 0.98982713 | −0.25791379 | 671 | 1.453855457 | −0.51177209 | −0.78608937 | 0.361715513 |
| 576 | −0.2346025 | 0.890438549 | −0.13206526 | −0.83961838 | 672 | 0.771613806 | −0.81209599 | −0.85297613 | 0.084880782 |
| 577 | 0.484934913 | 2.001798597 | −0.11430063 | −0.05230593 | 673 | 1.874725149 | 0.921395625 | 3.05642524 | 2.616508159 |
| 578 | 1.138642907 | −0.72228381 | −1.0321 | −0.60639529 | 674 | 5.912391366 | 3.468705262 | 6.81994671 | 7.217631788 |
| 579 | −2.722013313 | −3.79238321 | −1.13572295 | 0.953543134 | 675 | 0.525794155 | 0.473286101 | 2.51749677 | 2.935001452 |
| 580 | 1.138642907 | −0.66601616 | −0.95089973 | 1.036450105 | 676 | 0.623704257 | 1.523736626 | 2.50208859 | 2.474137331 |
| 581 | 1.105119249 | −0.82090309 | −0.06184517 | −0.90904158 | 677 | −0.548848405 | 0.058004962 | 1.07849806 | 2.361730638 |
| 582 | 2.092976965 | −0.31228784 | 0.08755137 | −0.62955362 | 678 | 4.818555677 | 1.506257638 | 4.96635528 | 5.508133385 |
| 583 | −0.24632881 | −1.33540368 | −0.96483147 | 0.624830731 | 679 | 4.332202737 | 2.699343437 | 5.65576391 | 5.021298111 |
| 584 | 2.237616041 | 0.30800753 | −0.44296441 | −0.71918014 | 680 | 4.042984412 | 4.75506829 | 4.65903898 | 4.913020939 |
| 585 | 0.634021669 | −0.28724544 | −0.74527157 | −1.361765 | 681 | 0.5959536 | 2.091803965 | −0.14697928 | −0.71889234 |
| 586 | 1.313957377 | 0.449601 | 1.50810166 | −0.30998322 | 683 | 0.87899671 | 0.043210589 | 1.37554648 | −0.60198897 |
| 587 | 0.304876136 | −0.43283205 | 1.23096012 | 0.398961811 | 684 | 2.349844428 | 1.181400632 | 2.15359469 | 2.136987013 |
| 588 | 0.449793066 | 0.007950225 | 0.8004147 | −0.63434071 | 686 | 1.024635336 | 1.040500794 | 0.9820242 | −1.16405004 |
| 589 | −0.681766404 | 1.08547116 | 0.54331319 | −2.16710754 | 687 | 0.551495677 | 0.66297128 | −0.45433071 | −1.28827912 |
| 591 | −0.34676031 | −0.77573166 | 1.85884084 | 0.312272735 | 691 | 1.609835015 | 2.898881191 | −0.99203246 | −0.15162554 |
| 592 | −1.573190219 | 2.29028194 | 1.86285367 | 0.687279186 | 692 | 2.002379485 | 3.95875961 | 1.1705779 | 0.346542121 |
| 594 | −1.45374647 | 0.452156392 | 2.48970747 | 0.858468114 | 693 | 4.264631423 | 4.375626605 | 0.93418004 | 0.114988571 |
| 595 | 0.058003677 | −1.91126878 | 1.52586392 | −0.07528071 | 693 | 4.264631423 | 4.375626605 | 0.93418004 | 0.114988571 |
| 599 | 1.485777974 | 1.54384772 | 0.79002365 | −0.09069773 | 694 | 4.858313721 | 4.772826468 | 3.58732214 | 2.558402204 |
| 600 | 1.914093549 | 0.841364523 | 0.15173954 | 0.255445859 | 696 | 2.99409154 | 3.843066736 | 2.50597637 | 1.205022789 |
| 601 | 1.203870517 | 1.17864533 | 1.22686262 | 0.453935114 | 697 | 0.407534444 | 2.829113684 | 2.16548165 | 0.756766079 |
| 602 | 0.771984982 | 0.66859171 | −0.37427136 | 0.07599515 | 698 | 0.983060431 | 2.328872529 | 1.67788951 | 0.805938034 |
| 603 | 3.218950175 | 1.464118271 | 2.47512497 | 1.214429025 | 699 | 0.996500165 | 0.60129571 | −0.27496491 | −0.22179967 |
| 604 | 2.710087358 | 1.517756148 | 0.35088855 | 0.603171932 | 700 | 0.698400489 | 0.514637899 | 1.14265307 | 0.816064314 |
| 605 | 0.703615734 | 0.42129186 | 0.39567696 | 0.41729786 | 701 | 0.592372435 | −0.67812322 | −1.75051912 | −0.51109618 |
| 606 | 0.055463315 | 1.972687323 | 3.42898264 | 1.395457482 | 702 | −0.211768579 | 1.46336231 | −0.93580247 | −1.48749449 |
| 607 | −0.146397553 | −2.05649732 | 0.17598641 | 1.900931587 | 703 | 0.372029303 | 0.866016277 | −0.91679974 | 0.347054507 |
| 608 | 1.473771668 | 2.08260463 | −1.09319437 | 0.44289209 | 704 | 1.187861135 | 0.858978871 | 0.1265005 | 0.217668671 |
| 609 | −0.466215117 | 0.845009196 | 1.89800228 | 0.840292062 | 706 | 0.193569186 | 1.623921627 | 0.0867618 | 0.808617424 |
| 610 | 2.14236439 | 1.079695535 | 0.29060257 | 1.329215628 | 707 | 0.819562098 | 3.57840156 | 3.38080377 | 1.26599216 |
| 611 | 1.078583502 | 1.707732184 | −0.73721672 | −0.87923138 | 708 | 2.391828225 | 1.877690145 | 3.85935427 | 1.647356195 |
| 612 | −0.128136098 | 1.038320983 | −0.63703066 | 0.184527669 | 709 | 1.280902077 | 2.17019575 | 3.40315777 | 0.126982574 |
| 613 | 1.599427115 | 3.615521066 | 0.43343413 | −0.1515479 | 710 | 1.454593977 | 3.128186882 | −2.26368122 | −0.02251455 |
| 614 | 1.489603514 | 2.706865637 | −0.06242639 | −0.47244791 | 711 | −0.783387499 | 1.465620573 | 1.22912535 | −1.41213701 |
| 615 | 1.960664614 | 4.490550162 | 2.26962278 | 0.346542121 | 712 | 1.936489942 | 2.528373237 | 2.13424487 | 2.393940425 |
| 616 | 2.689328335 | 3.692579375 | 2.01499213 | 1.348800283 | 713 | 1.303999908 | 2.146563611 | −0.26420591 | −0.01477791 |
| 617 | −0.845027889 | 0.504788036 | 0.4957383 | −0.65628324 | 714 | 2.3584433 | 3.778880151 | 3.4396901 | 1.593719007 |
| 618 | −0.461016335 | 1.612995126 | 1.09551709 | −1.62235977 | 715 | 4.023918591 | 3.403899942 | 5.07447567 | 4.880181625 |
| 619 | −0.222804396 | 0.361727974 | 0.62743416 | −1.02982449 | 716 | 0.981194248 | 1.73892162 | 2.21166953 | 2.738129365 |
| 620 | 0.745610019 | −0.76737462 | −0.67364137 | 1.696394301 | 717 | 0.983060431 | 2.328872529 | 1.67788951 | 0.805938034 |
| 621 | 3.671429366 | 1.708460032 | 4.57083156 | 1.955988764 | 718 | 1.241840746 | 3.430871861 | 0.55000978 | 1.073616332 |
| 624 | 2.139270802 | 2.093130621 | 2.5533383 | 3.30383102 | 719 | 1.483275952 | 3.037398628 | −1.55547275 | −0.47244791 |
| 625 | 0.665423108 | 1.356936283 | 1.5515704 | 1.874119646 | 720 | 2.372311412 | 3.403234423 | −0.21191089 | −0.08519829 |
| 626 | 1.292942787 | 0.621140137 | 2.28513785 | 1.042322574 | 721 | 2.128185431 | 0.274654772 | 0.47626043 | 2.465333527 |
| 627 | 1.14724223 | −0.51104438 | 1.01088446 | 1.51232276 | 722 | 0.616377169 | −0.58753328 | 0.48821573 | 1.063402884 |
| 628 | 1.44418629 | 3.825155203 | −0.84341678 | −0.02251455 | 723 | −1.273274349 | −1.12897478 | 1.71118519 | 4.067480158 |
| 631 | 2.622138509 | 5.106659136 | 4.48303003 | 2.115425367 | 724 | 2.103515193 | 0.165377929 | −0.18223896 | 0.288303217 |
| 632 | 2.450328692 | 4.670297017 | 4.54579766 | 2.15781135 | 725 | 0.983060431 | 2.328872529 | 1.67788951 | 0.805938034 |
| 633 | 1.560465308 | 2.636096631 | 2.45546606 | 0.920962489 | 726 | 2.887615733 | 3.282342953 | 1.95034945 | 2.462290186 |
| 635 | 1.510161132 | 2.388971583 | −0.63579931 | 1.939575919 | 727 | 2.241052707 | 2.13951389 | 0.36814978 | 0.371689426 |
| 636 | 1.433842763 | 0.529693203 | −0.23195491 | 1.22356734 | 730 | 1.121105724 | −0.20397307 | −0.15741334 | 0.897609916 |
| 638 | 1.921725015 | 0.758255259 | 0.81570609 | 3.615611357 | 731 | 1.437838545 | −0.09620743 | 0.02756967 | 1.949139525 |
| 639 | 0.422001837 | −0.14885323 | −0.00660617 | 1.726576493 | 733 | −0.46922259 | 1.067777032 | 1.61226345 | 0.185415155 |
| 640 | 0.865825265 | −0.28827025 | −0.54129473 | 0.283616979 | 735 | −0.081273581 | 1.192925027 | 1.67970188 | 0.33874614 |
| 641 | 0.813978315 | 0.509726232 | 0.37457254 | 0.842075065 | 736 | −0.13000788 | 1.099012031 | 1.64139691 | 0.248287146 |
| 644 | 0.85173251 | 0.664325682 | 1.88299246 | 0.951603698 | 738 | 1.670680003 | −0.20756775 | −0.73755051 | −0.84924056 |
| 645 | 0.417907652 | −1.00347186 | 0.9667556 | −0.47157656 | 740 | −1.532691904 | −2.55214711 | 0.57438104 | 0.555698696 |
| 647 | 0.221569324 | −1.2239438 | 0.91464498 | −0.19166679 | 741 | 1.407504561 | 0.048284736 | 1.01405149 | −2.2579901 |
| 649 | −0.560315649 | −0.67419393 | −0.02482011 | 1.492767049 | 742 | 0.644803847 | 0.644647752 | 1.35192052 | −0.62780087 |
| 650 | 1.640396187 | 0.328871961 | 0.04729888 | 0.912259803 | 743 | 0.174679072 | 0.169515693 | 0.62350977 | −0.08144308 |
| 651 | 0.672555558 | −0.9987845 | 0.48545476 | −0.13530683 | 744 | 0.02068385 | 0.648730454 | −0.04946215 | 0.214634634 |
| 652 | −0.995969271 | −1.38653208 | −0.49268035 | 0.944524468 | 745 | 0.741424752 | 0.523647641 | 0.52863925 | −0.65426285 |
| 653 | 1.203949791 | 0.0153333 | −0.10401424 | 0.73323846 | 746 | 1.285306965 | 1.929408375 | 0.85560877 | −1.4619958 |
| 655 | 1.334772083 | 0.418728831 | −0.92221842 | 1.317365259 | 748 | −1.513804897 | −1.10823383 | 1.09397284 | −0.88975989 |
| 658 | 0.414934548 | 0.314990682 | 2.78051829 | 2.656854539 | 750 | 2.554017714 | 3.544542579 | 4.42317523 | 1.647356195 |
| 659 | 3.996948911 | 1.915319951 | 3.03990612 | 5.764113617 | 752 | 2.592229701 | 1.158945916 | 0.24149847 | −0.58379051 |

| Material No. | MORV value for Equation a.) | MORV Value for Equation b.) | MORV Value for Equation c.) | MORV value for Equation d.) | Material No. | MORV value for Equation a.) | MORV Value for Equation b.) | MORV Value for Equation c.) | MORV value for Equation d.) |
|---|---|---|---|---|---|---|---|---|---|
| 754 | 1.649506181 | 1.31981993 | 2.36997533 | 0.406081966 | 868 | 2.237616041 | −0.17986241 | −0.86317199 | 1.325805381 |
| 755 | −0.028552173 | 0.253838465 | 0.95694896 | −0.16565786 | 869 | 1.747776963 | −0.25802105 | −1.11614995 | −0.77093434 |
| 757 | 1.446915042 | 0.673406021 | −0.6641103 | −1.80002119 | 870 | 2.592229701 | 2.030913569 | −0.50618719 | 1.463926567 |
| 758 | 5.933043009 | 5.716461604 | 6.67410554 | 4.433272782 | 871 | 2.592229701 | 2.510587108 | −0.07540594 | −0.58371481 |
| 760 | −3.195604514 | −2.60998376 | −0.11222221 | 0.792186468 | 872 | 1.800767509 | 1.372656013 | 2.09551175 | 2.849728342 |
| 761 | 0.286783044 | −0.52414055 | −0.57593161 | 0.628896611 | 873 | 1.849432484 | 4.556065495 | −0.39732139 | −0.67726477 |
| 763 | 1.405567948 | −0.84372738 | −1.32379279 | −0.50314577 | 875 | 0.201768224 | 0.618509503 | −0.39732139 | −0.67726477 |
| 766 | 0.279442569 | −1.00722191 | −0.18524031 | 2.487147765 | 876 | 2.237616041 | 1.553468488 | −0.72864242 | −0.33330779 |
| 767 | −1.32777782 | −2.36136561 | −0.79602501 | 1.247063893 | 877 | 0.323968221 | −1.00428076 | −1.65151616 | 1.031096548 |
| 768 | −0.692560954 | −1.92177717 | 0.46687554 | 2.400762497 | 878 | 0.783570663 | 2.023288951 | −0.03975252 | 0.474038265 |
| 769 | 1.889999468 | 1.112266205 | 0.82815523 | 0.525271623 | 879 | 1.187592149 | 1.464239711 | 0.67009263 | 1.103774764 |
| 770 | 2.237616041 | 2.282141767 | −0.149966 | −0.71866539 | 880 | −0.192632911 | 0.142411101 | 0.79310676 | 0.125548041 |
| 771 | 0.909356011 | 0.368597887 | 1.03689838 | 1.001198751 | 881 | 1.071875228 | 0.911734331 | −1.50008456 | 0.185176261 |
| 772 | 1.328601831 | 0.715296776 | 0.20358825 | 1.147403521 | 882 | 0.798806784 | −0.1516478 | −0.64900063 | −0.77199025 |
| 774 | 2.002379485 | 3.95875961 | 1.1705779 | 0.346542121 | 883 | −0.671908804 | −0.65984824 | 0.5238174 | −0.85314111 |
| 775 | 1.936489942 | 2.528373237 | 2.13424487 | 2.393940425 | 884 | 2.863652137 | 1.896850773 | 0.06443558 | −0.44689505 |
| 776 | 1.495019673 | 4.35984375 | 2.59969954 | 2.95313487 | 885 | 2.314558863 | −0.25458637 | 0.22080129 | −0.04142716 |
| 777 | 0.206892499 | −0.57813502 | −0.32983 | 0.781221286 | 886 | 2.314558863 | −0.25458637 | 0.22080129 | −0.04142716 |
| 778 | 1.340232187 | −0.11034804 | 0.35759778 | 1.690582999 | 888 | 0.131224024 | 0.21510779 | −1.70996346 | 0.964902175 |
| 779 | 0.595257521 | −0.85639987 | 0.19436224 | −0.73333902 | 889 | 0.742030255 | 0.281479436 | −1.4156326 | −1.91369695 |
| 781 | 2.187955186 | 2.571774369 | 2.74817529 | −0.52827851 | 890 | 1.071875228 | 0.911734331 | −1.50008456 | 0.185176261 |
| 782 | 0.893855657 | 0.63313318 | 1.19104388 | −1.61620514 | 891 | 0.742030255 | 0.281479436 | −1.4156326 | −1.91369695 |
| 784 | −0.275919571 | −1.64491584 | 0.60429762 | −1.5580623 | 892 | 1.749446006 | 0.076054765 | −0.59137073 | 0.291488011 |
| 786 | −0.043537347 | 1.337721065 | −0.56551398 | −0.02167052 | 893 | 0.869958847 | 0.843158237 | 0.61532515 | 3.158279932 |
| 788 | 2.147983695 | 1.250042565 | 1.72576392 | 1.626956379 | 894 | 1.749446006 | 0.076054765 | −0.59137073 | 0.291488011 |
| 789 | −0.624451013 | 0.76248127 | −0.79219481 | −0.73513092 | 897 | −0.047486491 | 1.045012945 | −0.25220201 | −0.31982826 |
| 791 | 0.227060873 | −0.04783658 | −0.16862915 | 1.166609659 | 899 | 0.784181146 | −0.20530019 | −1.89414748 | 0.152726109 |
| 792 | 0.90746622 | 1.643598677 | 0.26467094 | 0.396081003 | 900 | 0.784181146 | −0.20530019 | −1.89414748 | 0.152726109 |
| 796 | 0.811374104 | 0.766579899 | 0.10161642 | 0.135186519 | 901 | −0.440378333 | 0.918089245 | 0.03050609 | −1.62235977 |
| 797 | −0.185638022 | 0.53853264 | 0.65441562 | −0.25681926 | 902 | −0.2346025 | 0.890438419 | −0.13206526 | −0.83961838 |
| 799 | 0.657769581 | 0.095543194 | 0.89522656 | 0.558428618 | 903 | −0.440378333 | 0.918089245 | 0.03050609 | −1.62235977 |
| 800 | 0.227060873 | −0.04783658 | −0.16862915 | 1.166609659 | 904 | −1.320466583 | −2.49763118 | 0.9787365 | −1.85867969 |
| 802 | −0.660595577 | 1.597474466 | 1.49106895 | −0.20429128 | 905 | −0.386224123 | −0.24799559 | 1.19406353 | −1.61243489 |
| 803 | 1.706162052 | 0.623892414 | 0.59662073 | 0.7745661 | 908 | 1.878331515 | 1.287303121 | 0.11530502 | 1.132065786 |
| 804 | 3.478490379 | 2.348697011 | 3.96279011 | 2.456963386 | 909 | 0.614968453 | −1.61827184 | −0.80789799 | −0.66927285 |
| 805 | 0.377241729 | 0.83329773 | 0.1712741 | 1.057125999 | 912 | 0.530707518 | 0.774109528 | 3.0396125 | 4.394775258 |
| 806 | 2.863652137 | 0.771287371 | −0.4183972 | −0.44551461 | 913 | 0.337020095 | 1.531840025 | 0.10544973 | 0.347450471 |
| 807 | 1.794279084 | 0.711717977 | 0.35187068 | −1.0208486 | 914 | 0.774589061 | 1.224705331 | 1.87994281 | −0.11684579 |
| 808 | 0.408210632 | 0.633556897 | −0.37022584 | 0.717270748 | 916 | −0.363201351 | 0.35600238 | −1.20673542 | 2.056973054 |
| 810 | −2.506277966 | −2.61703099 | 0.87880054 | −0.72832121 | 918 | 0.153047955 | 0.702054562 | 0.76757802 | 0.096096862 |
| 811 | −0.789075789 | −0.15346024 | 0.64720487 | −0.48507671 | 919 | 2.891894151 | 2.295157633 | 3.54101626 | 1.984030826 |
| 812 | −1.395132583 | −2.59063834 | 0.14973761 | 0.623759794 | 920 | 1.292959895 | 0.808281618 | 2.92956952 | 2.204248324 |
| 814 | 0.414608216 | −0.23108581 | 1.15081653 | −1.10351559 | 921 | −0.465333775 | 0.862817284 | 0.1439546 | 0.64701735 |
| 817 | −0.24632881 | −0.09354384 | −0.13580399 | 0.599029186 | 922 | 1.54265003 | 0.291977233 | 0.79089158 | 0.801314068 |
| 819 | 0.805916178 | 0.96701754 | −0.8811308 | −1.23858491 | 923 | 1.340862559 | 0.503169303 | 0.53213093 | 3.164832031 |
| 820 | 0.744770665 | −0.73855596 | −0.2249849 | −0.2981968 | 924 | 0.158497146 | 1.507280765 | 2.25315926 | 1.173977914 |
| 821 | 1.099377934 | −0.55297074 | −0.58846144 | −1.64325365 | 925 | 1.23162703 | 1.671882685 | 3.1838372 | −0.22917041 |
| 824 | −0.183625049 | 1.183962609 | 1.63494269 | 0.25504959 | 926 | 2.608734063 | 3.080604939 | −0.69726361 | −0.36219702 |
| 826 | 1.678825829 | 1.234136613 | 1.45948258 | 0.224375571 | 927 | 1.879182741 | 3.409153142 | 2.48473663 | 3.409954437 |
| 827 | 2.592229701 | 0.621958527 | −0.52522117 | −0.19676404 | 928 | −0.093106169 | 0.019939108 | 0.15932154 | 1.229749745 |
| 828 | 2.592229701 | 0.57915141 | −0.51767373 | −0.58077497 | 929 | 1.670680003 | 1.94609957 | 0.19633838 | 1.14825764 |
| 829 | 1.670680003 | 1.284791367 | 0.14864516 | −0.84985664 | 930 | 3.052627325 | 0.956834107 | −0.29721209 | −0.31007607 |
| 831 | 1.116827432 | −0.75462162 | 0.39137278 | −0.04171761 | 931 | 0.367631287 | 0.501274945 | −1.31074554 | −0.39331005 |
| 832 | 0.516805788 | −0.98195801 | −1.03806082 | −0.25383454 | 933 | 3.702965303 | 3.03402795 | 4.33630831 | 4.238503729 |
| 833 | 1.490368312 | 0.080687244 | −0.97130296 | 0.833722265 | 937 | 0.570011387 | 0.097928934 | 1.03350455 | −0.13392581 |
| 834 | −0.369014518 | −1.35841128 | −1.27372214 | 1.351157886 | 939 | 1.801474588 | 0.770314085 | 0.70188154 | 0.22333959 |
| 835 | 0.914072736 | −0.8695664 | 0.36889122 | −0.08606658 | 940 | −0.412950838 | −0.1781887 | 0.50649275 | −0.57215449 |
| 836 | 0.998848923 | −0.42464651 | −0.23731009 | 0.395895785 | 941 | 1.691004766 | −0.42331992 | 0.66279648 | 0.0318465 |
| 837 | 1.670680003 | 0.070165381 | −0.64700996 | −0.85055617 | 942 | 1.451782586 | −0.565439 | −0.32447381 | −0.43378383 |
| 838 | 0.810918992 | −0.75696962 | −0.21854084 | 0.836677293 | 943 | 1.188491672 | 0.120632811 | 0.20106994 | 3.078484746 |
| 839 | 1.066219316 | −0.66764691 | −0.49983634 | 0.669914 | 945 | 1.214814941 | 0.806987609 | 0.47605587 | 1.372949466 |
| 840 | 1.078821776 | −0.72511699 | −1.00012288 | −0.15789319 | 946 | 0.561732094 | 1.21448402 | 0.35542793 | −1.03704442 |
| 845 | −0.163950017 | −0.21616766 | 0.65276069 | −0.52575739 | 947 | 0.956565856 | 1.505997176 | 0.88115653 | −0.60583691 |
| 846 | 0.665621985 | −3.16625248 | 0.34329102 | −1.44312929 | 948 | 0.592575441 | 1.383482681 | 0.93567635 | 1.058669028 |
| 847 | −0.233400992 | −1.15488444 | 0.83051343 | −1.85751897 | 950 | 0.343657562 | −0.85471906 | −0.21125904 | 1.184648122 |
| 848 | −0.631135606 | 0.037691556 | 0.57903451 | −0.9926 | 951 | 1.236659334 | 3.828926809 | 1.57729777 | −0.31942874 |
| 849 | 1.707541313 | 0.010345383 | 0.48581606 | 1.513341091 | 953 | 1.836389049 | 0.755753735 | −0.36014522 | 1.262853393 |
| 850 | 1.447075297 | 0.022864201 | 0.99130501 | 0.473154634 | 953 | 1.836389049 | 0.755753735 | −0.36014522 | 1.262853393 |
| 851 | −0.24632881 | −0.23975549 | −0.01449288 | 0.574861147 | 954 | 1.001653875 | −0.85635082 | 0.89224781 | −0.39245818 |
| 852 | 1.176028423 | −0.85747031 | −0.72464089 | 0.30542841 | 955 | −0.122918652 | −0.846489 | −0.63367729 | 1.182912962 |
| 856 | 2.237616041 | 0.345329597 | −0.60597063 | −0.71581056 | 956 | 0.589766639 | −0.9783487 | −0.67638264 | −0.38772225 |
| 858 | −1.47960224 | −2.5770536 | −1.03619781 | 0.847300104 | 958 | 0.715082397 | −0.90020686 | 0.86817768 | 0.030652004 |
| 864 | 1.670680003 | 1.284791101 | 0.14864516 | −0.84985664 | 959 | 1.609198886 | 0.500797943 | 0.795571 | 0.908389449 |
| 865 | 1.670680003 | 1.916382859 | 0.6998144 | 1.124089601 | 960 | 0.952787327 | −0.90555475 | −0.17381408 | 0.06786323 |
| 866 | 1.024819853 | −0.7521596 | 0.35073152 | −2.14193241 | 962 | 1.836429446 | 0.208275147 | −0.14300625 | 1.067462181 |

| Material No. | MORV value for Equation a.) | MORV Value for Equation b.) | MORV Value for Equation c.) | MORV value for Equation d.) |
| --- | --- | --- | --- | --- |
| 965 | 1.9158432 | 0.35211823 | -1.02174589 | 0.625657932 |
| 967 | 1.383869627 | 0.274520494 | -0.11659267 | 0.840327437 |
| 969 | -0.445579934 | -1.68867059 | -0.5241276 | 2.233793943 |
| 971 | 0.736419048 | 0.409875189 | -0.63140848 | 0.034514594 |
| 973 | 1.073465817 | 2.18418874 | 2.01361447 | -0.93754437 |
| 974 | 0.130904221 | 1.882440008 | 1.85101055 | 0.112524893 |
| 976 | -0.236681385 | -0.09745533 | 0.1779313 | 2.08923366 |
| 977 | 0.904402612 | 0.936956925 | 0.87731788 | 0.102346515 |
| 978 | 2.201759817 | 2.123549573 | 3.7881607 | 2.358768953 |
| 980 | 1.784266982 | 1.845281076 | 3.42873622 | -0.31098233 |
| 981 | -0.225023329 | 0.087962898 | -0.29053012 | 0.514272787 |
| 982 | -0.231175318 | -0.0159671 | 1.27391892 | 1.090487158 |
| 983 | 0.889215441 | 0.24321159 | 0.06877629 | 0.816247177 |
| 985 | 1.864634345 | 0.133647536 | 1.29803755 | 1.951226654 |
| 986 | 0.511450274 | -2.33512445 | -0.56246315 | -0.42184152 |
| 987 | 0.847260813 | 0.368638185 | 0.4114346 | 0.219336109 |
| 988 | 1.596170102 | 1.592158381 | 0.30052357 | 0.283467897 |
| 993 | -3.549941097 | -2.6847861 | -0.17502622 | 1.41034664 |
| 994 | 0.445802042 | 0.899738574 | 0.61059602 | 0.323194673 |
| 995 | 0.949498724 | 0.357111159 | 0.28371155 | -0.14156488 |
| 998 | 2.197271885 | 1.578871826 | 0.90563334 | 1.056619658 |
| 998 | 2.197271885 | 1.578871826 | 0.90563334 | 1.056619658 |
| 1000 | 1.456120673 | 0.626173572 | 0.07683183 | -0.43324035 |
| 1001 | -0.440378333 | 0.918089245 | 0.03050609 | -1.62235977 |
| 1002 | 0.819929066 | 0.459101825 | -0.09227583 | 0.324342063 |
| 1003 | 1.64412453 | -0.09343399 | 0.70197344 | 3.710273595 |
| 1004 | 0.796928207 | 0.459954079 | -0.88538616 | 0.152000937 |
| 1005 | 0.044923203 | -0.19994963 | 0.60082875 | 0.258347835 |
| 1006 | -0.320452673 | -0.33232662 | -0.52315783 | 1.406273663 |
| 1007 | 4.040291133 | 3.474551355 | 3.57146797 | 3.565985043 |
| 1008 | 0.764519082 | 0.917635102 | 2.88258762 | 2.319622474 |
| 1009 | -0.071112206 | 0.539362906 | 2.98048732 | 0.580423329 |
| 1010 | -0.689737481 | 0.547928768 | 1.98805626 | -0.76653376 |
| 1011 | 0.343668917 | 0.931501008 | -0.05483722 | 0.395369857 |
| 1012 | 1.926713131 | 0.124849138 | -0.09654906 | 1.126499382 |
| 1016 | 0.124247716 | 0.193102712 | 0.39003599 | 1.737670628 |
| 1017 | 0.131224136 | 0.21510779 | -1.70996346 | 0.964902175 |
| 1018 | 0.499624069 | 0.962843507 | 0.77617619 | -1.15296947 |
| 1019 | 0.813491983 | 0.322635656 | 0.02800396 | 0.599500927 |
| 1020 | 0.715468114 | 1.015469049 | 1.45994989 | 0.352548581 |
| 1021 | -1.176339404 | 1.539767848 | -0.14427147 | 1.389902738 |
| 1022 | 1.364966718 | 1.690570939 | 2.05914194 | 2.364375484 |
| 1023 | 2.154641091 | 0.800066339 | 0.85365652 | 0.965810338 |
| 1024 | 2.302280068 | 1.252164308 | 1.73414439 | 1.549538352 |
| 1025 | 1.878331515 | 1.287303121 | 0.11530502 | 1.132065786 |
| 1026 | 2.97722987 | 2.096441965 | 3.87172868 | 0.550274831 |
| 1027 | 2.474381478 | 1.950326182 | 3.81861867 | 1.366897355 |
| 1028 | 1.778414353 | 3.114931059 | 4.47690731 | 6.054314034 |
| 1029 | 3.672910795 | 2.760483725 | 3.26915034 | 3.042677588 |
| 1030 | -0.604959715 | -2.13584086 | 0.8687855 | 0.024144016 |
| 1031 | 2.012732245 | 2.293857161 | 0.54405555 | 1.261882121 |
| 1032 | -1.086688867 | 0.953083194 | 2.92177054 | 0.876865185 |
| 1033 | 1.617520676 | 1.008017006 | 2.21183536 | -0.1288484 |
| 1035 | 2.506372295 | 3.419954592 | 4.58206882 | 4.134341651 |
| 1036 | -0.675805062 | -0.15357004 | 0.94597719 | 3.966016669 |
| 1037 | -0.275092569 | -0.67687665 | -0.52763797 | 1.489972106 |
| 1038 | 2.753559643 | 3.81185814 | 2.71344734 | 2.243351472 |
| 1039 | 0.65087433 | 0.026885305 | -0.0153558 | 0.011870127 |
| 1040 | 0.141526548 | -1.65455278 | 0.50170705 | -1.90794 |
| 1041 | 0.458680435 | -0.69730218 | -0.48806249 | 0.586073092 |
| 1042 | -0.513264812 | -0.22001961 | 0.36339519 | 1.03208599 |
| 1043 | -1.497887014 | -1.76116109 | -0.76634926 | 1.137002742 |
| 1045 | 2.863652137 | 1.96790869 | 0.43661485 | -0.44756897 |
| 1046 | 0.981194248 | 1.73892162 | 2.21166953 | 2.738129365 |
| 1047 | 0.981194248 | 1.73892162 | 2.21166953 | 2.738129365 |
| 1051 | 0.70261974 | -0.22197386 | 0.19710806 | -2.37196477 |
| 1052 | 0.662126832 | 0.741436531 | 0.61672724 | 0.289359903 |
| 1053 | 0.87463644 | -0.19717783 | 1.2664131 | -0.4187507 |
| 1054 | 0.284558077 | -1.46754925 | -0.03124571 | 0.587227244 |
| 1055 | 0.885837831 | -0.91907796 | -0.45817355 | -1.1936897 |
| 1057 | 0.790964847 | 1.387925398 | -0.18370692 | 1.302393792 |
| 1058 | -1.052897931 | -0.85226912 | 0.90324527 | -1.09684959 |
| 1059 | -0.871565421 | -0.17856476 | 1.51267137 | -1.52734367 |
| 1060 | 3.311161199 | 3.074783921 | 2.10199297 | 1.822541682 |
| 1061 | -0.655128061 | 0.497032417 | 0.92381279 | -0.56348341 |
| 1062 | -0.443129049 | 0.96200606 | 1.51641349 | -0.22974864 |
| 1063 | 1.385675542 | 0.738759296 | 1.1677069 | 0.501211562 |
| 1064 | 1.670680003 | -0.20756775 | -0.73755051 | -0.84924056 |
| 1065 | 1.43532227 | 1.656262941 | -1.09448841 | 1.674272267 |
| 1066 | 1.670680003 | 1.284791101 | 0.14864516 | -0.84985664 |
| 1067 | 2.237616041 | 0.345329863 | -0.60597063 | -0.71581056 |
| 1069 | -0.24632881 | -0.23975349 | -0.01449288 | 0.574861147 |
| 1070 | 1.670680003 | 0.070165381 | -0.64700996 | -0.85055617 |
| 1071 | -1.02687397 | -0.36244273 | 0.13010074 | 0.535909448 |
| 1072 | 1.670680003 | 1.94609957 | 0.19633838 | 1.14825764 |
| 1073 | 2.237616041 | 1.438074134 | 0.31117554 | -0.71786492 |
| 1074 | -0.192632911 | 0.142411101 | 0.79310676 | 0.125548041 |
| 1075 | 0.909356011 | 0.368597887 | 1.03689838 | 1.001198751 |
| 1076 | 0.812238101 | 0.195908668 | 0.21564664 | 0.219336109 |
| 1077 | 0.325255266 | 1.131242708 | -2.79377204 | -0.62848261 |
| 1078 | 0.325255266 | 1.131242708 | -2.79377204 | -0.62848261 |
| 1079 | 0.85330799 | -0.6855194 | -0.90046979 | -0.46415796 |
| 1081 | -0.131519393 | 0.731836014 | 0.81604919 | -1.29993979 |
| 1082 | 0.744770665 | 0.155243763 | -1.8029919 | 1.023503542 |
| 1083 | 1.415726941 | 0.086297223 | 3.43559555 | -0.12964168 |
| 1084 | 0.161304111 | 0.66712144 | 0.58401752 | 0.373809692 |
| 1085 | -0.72863532 | -0.2873027 | 2.21251376 | 3.003873022 |
| 1088 | -1.1773616 | -0.23258175 | 0.40529195 | 0.994988969 |
| 1089 | 2.769817302 | 1.661618789 | 3.97585272 | 1.059236597 |
| 1090 | 3.052627325 | 0.420821685 | -0.57080756 | 1.751222205 |
| 1091 | -3.379896722 | -3.71174986 | 2.53586709 | 0.644702886 |
| 1093 | 0.72304265 | 1.667011476 | 2.53982093 | 2.7903213 |
| 1095 | 0.744219765 | 1.372184572 | 0.15852396 | 1.126053442 |
| 1097 | 4.407270402 | 2.670641491 | 5.02636153 | 5.361271976 |
| 1098 | -1.85804837 | -2.59071226 | -0.46522239 | 0.655734646 |
| 1099 | 0.745797788 | -0.20547378 | 4.27836342 | 4.646390386 |
| 1102 | 2.068748434 | -0.24299896 | 0.07214682 | -1.11758276 |
| 1104 | 1.018876287 | 0.025163067 | -0.1106021 | 0.838914654 |
| 1105 | 2.387326861 | 3.865456674 | 2.2251199 | 0.728667998 |
| 1107 | 2.352582059 | 2.595496601 | 3.20492728 | 2.844590737 |
| 1110 | 0.302703712 | 0.599942142 | -0.25637571 | -0.03195517 |
| 1111 | 0.750930333 | 0.656784751 | 1.68326413 | 0.329846578 |
| 1112 | -0.205527848 | 0.287622624 | -0.00340777 | 0.59203719 |
| 1115 | 0.999825037 | 0.662221152 | 0.43571192 | 0.342558518 |
| 1116 | 0.873381263 | 1.544324176 | 0.13703728 | -0.38172701 |
| 1117 | -0.682983903 | 1.798204302 | 2.42110319 | -0.39173951 |
| 1118 | 0.069769623 | 0.496895599 | 0.67857133 | -0.14954441 |
| 1119 | -0.671908804 | -0.65984824 | 0.5238174 | -0.85314111 |
| 1120 | 0.953790113 | 1.106552668 | 3.00006904 | 1.585038764 |
| 1121 | -1.184630973 | 2.476138312 | 4.80971952 | 2.450646806 |
| 1122 | -1.02687397 | -0.36244273 | 0.13010074 | 0.535909448 |
| 1125 | 0.387315524 | -0.36101406 | 1.14153708 | -0.75303953 |
| 1126 | 1.021783831 | -0.0070257 | -0.14327539 | 3.954381426 |
| 1127 | 0.990592079 | 0.305612583 | 0.14155512 | -0.29526854 |
| 1128 | 0.990592079 | 0.305612583 | 0.14155512 | -0.29526854 |
| 1129 | 3.18966648 | 3.284362987 | 4.49398568 | 3.950809104 |
| 1131 | 1.650621055 | 1.545704806 | 2.37535081 | 1.259373143 |
| 1133 | -1.519747805 | -0.60804324 | 0.02746106 | 0.590708892 |
| 1134 | 0.815942067 | -0.16126019 | -0.54117238 | 0.613093526 |
| 1135 | 0.626973385 | 1.998305877 | 2.61706075 | 1.570404253 |
| 1136 | 2.812199484 | 1.353198146 | 2.05618426 | 1.869204406 |
| 1137 | 2.208307057 | 1.387136198 | 3.21521374 | 2.069795393 |
| 1138 | 1.670680003 | 1.316442078 | 0.14822999 | -0.46985154 |
| 1139 | 1.408517438 | 0.890457374 | 1.24524408 | 0.685687797 |
| 1140 | 2.765860952 | 2.525539595 | 4.12464228 | 3.833744077 |
| 1141 | -0.484394663 | 0.677713073 | -0.22783646 | -0.37267608 |
| 1142 | 2.54335679 | 4.298105601 | 3.36234238 | 2.684404542 |
| 1143 | 4.204367611 | 3.062126931 | 3.4234313 | 2.072899554 |
| 1144 | 2.479165229 | 3.226545885 | 4.65897152 | 4.952127235 |
| 1145 | 2.479158921 | 3.226545885 | 4.65897152 | 4.952127235 |
| 1146 | 0.774334025 | 1.075800774 | 1.06893156 | 1.011113116 |
| 1147 | 0.844648531 | 1.21935371 | 2.59138595 | 0.805938034 |
| 1148 | 2.906236436 | 1.550674121 | 3.56959167 | 2.832126896 |
| 1149 | 2.837627443 | 3.707154326 | 4.53384262 | 2.625871865 |

Air Freshening Compositions and Methods

An air freshening composition, said composition comprising, based on total composition weight:
   a) a sum total of from about 0.0001% to about 100%, preferably from about 0.0001% to about 50%, more preferably from about 0.01% to about 25%, most preferably from about 0.07% to about 15% of one or more malodor reduction materials, preferably 1 to about 20 malodor reduction materials, more preferably 1 to about 15 malodor reduction materials, most preferably 1 to about 10 malodor reduction materials, each of said malodor reduction materials having a MORV of at least 0.5, preferably from 0.5 to 10, more preferably from 1 to 10, most preferably from 1 to 5, and preferably each of said malodor reduction materials having a Universal MORV, or said sum total of malodor reduction materials having a Blocker Index of less than 3, more preferable less than about 2.5 even more preferably less than about 2 and still more preferably less than about 1 and most preferably 0 and/or a Blocker Index average of 3 to about 0.001; and b) optionally, from about 0.01% to about 90%, preferably from about 10% to about 90%, more preferably from about 20% to about 80%, most preferably from about 30% to about 70% of at least one solvent, preferably said solvent comprises an organic material having a vapor pressure of from about 0.000625 torr to about; 0.625 torr preferably from about 0.00625 torr to about 0.425 torr, more preferably; from about 0.0625 torr to about 0.325 torr, most preferably from about 0.0875 torr to about 0.225 torr;

c) optionally, an adjunct ingredient is disclosed.

In one aspect of said freshening composition, said sum total of malodor reduction materials has a Blocker Index of less than 3, more preferable less than about 2.5 even more preferably less than about 2 and still more preferably less than about 1 and most preferably 0 and/or a Blocker Index average of 3 to about 0.001.

In one aspect of said freshening composition, each of said malodor reduction materials has a MORV of at least 0.5, preferably from 0.5 to 10, more preferably from 1 to 10, most preferably from 1 to 5, and preferably each of said malodor reduction materials having a Universal MORV.

In one aspect of said freshening composition, said sum total of malodor reduction materials has a Fragrance Fidelity Index average of 3 to about 0.001 Fragrance Fidelity Index, preferably each malodor reduction material in said sum total of malodor reduction materials has a Fragrance Fidelity Index of less than 3, preferably less than 2, more preferably less than 1 and most preferably each malodor reduction material in said sum total of malodor reduction materials has a Fragrance Fidelity Index of 0.

In one aspect of said freshening composition, said freshening composition comprises one or more perfume raw materials other than said sum total of malodor reduction materials, the ratio of said one or more perfume raw materials to said sum total of malodor reduction material being from about 1,000,000:1 to about 1:1, preferably from about 10,000:1 to about 1:1, more preferably from about 2500:1 to 1:1, most preferably from about 5:1 to about 1:1.

In one aspect of said freshening composition, said cleaning and/or treatment composition comprises one or more malodor reduction materials having a vapor pressure of greater than 0.01 torr, preferably, greater than 0.01 torr to 10 torr, preferably said one or more malodor materials are selected from the group consisting of Table 1 materials 3; 4; 7; 9; 21; 25; 29; 30; 31; 32; 33; 34; 35; 42; 49; 50; 62; 64; 65; 67; 70; 91; 92; 93; 98; 101; 102; 103; 108; 110; 114; 117; 119; 122; 123; 126; 130; 142; 145; 146; 149; 155; 159; 167; 168; 170; 178; 186; 189; 190; 192; 193; 208; 209; 210; 218; 228; 229; 231; 243; 254; 256; 259; 267; 274; 278; 280; 281; 290; 294; 317; 318; 322; 325; 333; 338; 342; 344; 358; 362; 364; 375; 386; 394; 397; 398; 415; 421; 424; 428; 429; 436; 441; 444; 445; 449; 453; 461; 466; 468; 471; 473; 474; 475; 491; 519; 520; 524; 527; 530; 531; 532; 534; 544; 546; 551; 555; 565; 578; 580; 581; 584; 586; 587; 589; 603; 604; 606; 609; 611; 612; 614; 615; 618; 621; 627; 628; 631; 632; 633; 639; 649; 659; 668; 683; 686; 692; 693; 696; 698; 702; 708; 711; 714; 715; 717; 720; 725; 730; 738; 742; 748; 750; 752; 763; 766; 767; 768; 770; 774; 778; 781; 786; 791; 792; 800; 802; 806; 814; 821; 826; 827; 828; 829; 834; 837; 839; 840; 850; 852; 856; 864; 865; 866; 868; 869; 871; 873; 876; 877; 878; 879; 884; 897; 905; 914; 926; 928; 929; 937; 946; 947; 950; 955; 969; 973; 974; 982; 993; 1006; 1008; 1010; 1016; 1020; 1021; 1031; 1037; 1043; 1045; 1053; 1057; 1060; 1062; 1064; 1066; 1067; 1070; 1072; 1073; 1077; 1078; 1082; 1102; 1104; 1105; 1120; 1125; 1137; 1138; 1144; 1145 Table 2 materials 565; 631; 659; 715 Table 3 materials 9; 12; 19; 20; 21; 24; 25; 27; 32; 34; 53; 55; 59; 64; 65; 70; 73; 81; 84; 96; 97; 98; 108; 110; 111; 114; 116; 119; 125; 126; 133; 142; 146; 147; 150; 154; 157; 159; 163; 166; 167; 169; 178; 189; 192; 194; 198; 201; 204; 205; 228; 231; 232; 237; 239; 254; 256; 258; 264; 270; 273; 282; 283; 284; 287; 290; 302; 306; 312; 319; 322; 325; 333; 338; 344; 346; 354; 358; 362; 365; 366; 375; 376; 387; 412; 419; 420; 428; 429; 437; 438; 439; 443; 444; 447; 448; 461; 469; 474; 477; 481; 491; 492; 495; 496; 509; 512; 517; 518; 522; 525; 530; 535; 536; 538; 540; 542; 544; 547; 549; 554; 555; 556; 557; 575; 576; 579; 583; 585; 588; 589; 604; 605; 609; 617; 619; 633; 640; 645; 647; 651; 652; 662; 664; 665; 667; 683; 686; 687; 693; 698; 699; 701; 717; 725; 730; 740; 742; 744; 745; 760; 761; 777; 779; 784; 789; 792; 797; 806; 810; 812; 817; 819; 820; 827; 828; 832; 835; 836; 838; 839; 845; 846; 847; 848; 850; 851; 858; 865; 875; 878; 879; 882; 883; 888; 889; 891; 899; 900; 901; 902; 903; 904; 909; 914; 931; 937; 940; 946; 947; 956; 977; 981; 986; 987; 994; 995; 1001; 1004; 1008; 1010; 1011; 1017; 1018; 1019; 1020; 1030; 1031; 1039; 1040; 1041; 1051; 1053; 1054; 1055; 1057; 1058; 1061; 1062; 1069; 1071; 1076; 1081; 1082; 1098; 1102; 1104; 1105; 1115; 1119; 1120; 1122; 1127; 1128; 1141 and mixtures thereof, more preferably said malodor reduction materials are selected from the group consisting of Table 1 materials 3; 4; 7; 9; 21; 25; 29; 30; 31; 32; 33; 34; 35; 42; 49; 50; 62; 64; 65; 67; 70; 91; 92; 93; 98; 101; 102; 103; 108; 110; 114; 117; 119; 122; 123; 126; 130; 142; 145; 146; 149; 155; 159; 167; 168; 170; 178; 186; 189; 190; 192; 193; 208; 209; 210; 218; 228; 229; 231; 243; 254; 256; 259; 267; 274; 278; 280; 281; 290; 294; 317; 318; 322; 325; 333; 338; 342; 344; 358; 362; 364; 375; 386; 394; 397; 398; 415; 421; 424; 428; 429; 436; 441; 444; 445; 449; 453; 461; 466; 468; 471; 473; 474; 475; 491; 519; 520; 524; 527; 530; 531; 532; 534; 544; 546; 551; 555; 565; 578; 580; 581; 584; 586; 587; 589; 603; 604; 606; 609; 611; 612; 614; 615; 618; 621; 627; 628; 631; 632; 633; 639; 649; 659; 668; 683; 686; 692; 693; 696; 698; 702; 708; 711; 714; 715; 717; 720; 725; 730; 738; 742; 748; 750; 752; 763; 766; 767; 768; 770; 774; 778; 781; 786; 791; 792; 800; 802; 806; 814; 821; 826; 827; 828; 829; 834; 837; 839; 840; 850; 852; 856; 864; 865; 866; 868; 869; 871; 873; 876; 877; 878; 879; 884; 897; 905; 914; 926; 928; 929; 937; 946; 947; 950; 955; 969; 973; 974; 982; 993; 1006; 1008; 1010; 1016; 1020; 1021; 1031; 1037; 1043; 1045; 1053; 1057; 1060; 1062; 1064; 1066; 1067; 1070; 1072; 1073; 1077; 1078; 1082; 1102; 1104; 1105; 1120; 1125; 1137; 1138; 1144; 1145 Table 2 materials 565; 631; 659; 715, most preferably said malodor reduction materials are selected from the group consisting of Table 4 materials 7; 229; 281; 441; 603; 621; 627; 632; 696; 708; 714; 750; 1060; 1137; 1144; 1145 and mixtures thereof. All of the aforementioned materials have a vapor pressure that is greater than 0.01 torr, thus they effectively saturate the head space of a cleaning and/or treatment composition, wash solutions comprising same and a treated situs which leads to malodor blocking of any malodors in the cleaning and/or treatment composition, wash solutions comprising same and a treated situs. The more preferred and most preferred of the aforementioned material are particularly preferred as they are effective at counteracting all of the key malodors.

In one aspect of said freshening composition, less than 10%, preferably less than 5%, more preferably less than 1% of said malodor reduction materials and said one or more perfume raw materials, based on total combined weight of malodor reduction materials and said one or more perfume raw materials, comprise an unsaturated aldehyde moiety.

In one aspect of said freshening composition, said malodor reduction materials are not selected from the group consisting of Table 1-3 malodor reduction materials 302; 288; 50; 157; 1017; 888; 64; 1054; 832; 375; 390; 745; 504; 505; 140; 1012; 498; 362; 103; 356; 1074; 908; 1127; 475; 918; 687; 611; 317; 9; 141; 550; 602; 913; 1005; 521; 10; 215; 370; 335; 378; 1121; 360; 565; 1136; 1129; 655; 369; 1065; 914; 757; 601; 478; 889; 891; 358; 973; 162; 554; 522; 312; 125; 26; 418; 92; 586; 1026; 218; 31; 828; 871; 829; 1066; 287; 269; 769; 701; 1118; 70; 946; 142; 109; 108 or mixtures thereof.

In one aspect of said freshening composition, less than 50%, preferably less than 25%, more preferably less than 15% of said malodor reduction materials and said one or more perfume raw materials, based on total combined weight of malodor reduction materials and said one or more perfume raw materials has a vapor pressure of from about 0.000375 to about 4.00; more preferably from about 0.00175 to about 2.50, more preferably; from about 0.00875 to about 1.00, most preferably from about 0.0175 to about 0.50, preferably said composition comprises water.

In one aspect of said freshening composition, said freshening composition comprising a thickening or gelling agent, preferably said thickening or gelling agent is selected from the group consisting of:
 a) a polysaccharide gelling agent, preferably said polysaccharide gelling agent is selected from the group consisting of gellan, carrageenan, agar, alginate and mixtures thereof
 b) a cellulosic gelling agent, preferably said cellulosic gelling agent is selected from the group consisting of such as ethyl cellulose, derivatives of ethyl cellulose, methyl cellulose, derivatives of methyl cellulose and mixtures thereof
 c) an acrylic resin, preferably said acrylic resin comprises water-soluble polymers of acrylic acid or methacrylic acid In one aspect of said freshening composition, said freshening composition comprises an adjunct ingredient selected from the group consisting of:
 a) water,
 b) colorant and dyes,
 c) solvents and diluents such as glycol ethers, alcohols, liquid hydrocarbons, and esters of acetic acid, gluconic acid, adipic acid, glutaric, benzoic acid or succinic acid
 d) preservatives, preferably antioxidants, preferably the following antioxidants substituted phenols; UV absorbers preferably the following UV absorbers, preferably benzophenones, benzotriazoles, and derivatives of 2,2, 6,6-tetramethyl piperidine,
 e) insect repellants,
 f) antimicrobial agents, preferably quaternary ammonium compounds, alcohols, and isothiazolinone derivatives,
 g) fragrances and aromatherapy agents,
 h) and mixtures thereof.

A device comprising Applicants' freshening composition is disclosed. Preferably said device is selected from the group consisting of energized air fresheners and non energized air fresheners, more preferably said device is selected from the group consisting of:
 a) wick air fresheners;
 b) reservoir air fresheners;
 c) porous membrane air fresheners;
 d) power assisted delivery air fresheners, preferably power assisted delivery air fresheners selected from the group consisting of thermal drop-on-demand air fresheners, piezo air fresheners, heater air fresheners, fan air fresheners, or microfluidic devices air fresheners; and
 e) spray devices.

A method of controlling malodors comprising: contacting a situs comprising a malodor or a situs that will become malodorous with a composition selected from the group consisting of Applicants' freshening compositions and mixtures thereof is disclosed. Preferably said situs is air.

In one aspect of said method, said contacting step comprises contacting said situs with a sufficient amount of one or more of Applicants' freshening composition to provide said malodor with from about 0.1 nanogram (ng) to about 5000 ng, preferably from about 1 ng to about 3,500 ng most preferably from about 10 ng to about 1500 ng of said sum of malodor reduction materials per liter of said situs.

Delivery Systems

The composition of the present invention may be used with a hard surface cleaner, as is commonly used to clean countertops, tables and floors. A suitable floor cleaning liquid is sold by the instant assignee in a replaceable reservoir under the name WetJet. The cleaning solution may particularly be made according to the teachings of commonly assigned U.S. Pat. No. 6,814,088. The reservoir may be used with and dispensed from a floor cleaning implement, in conjunction with a disposable floor sheet. A suitable spray implement is also sold by the instant assignee under the name WetJet. A suitable reservoir and fitment therefor may be made according to the teachings of commonly assigned U.S. Pat. Nos. 6,386,392 and/or 7,172,099. If desired the floor cleaning implement may dispense steam, according to the teachings of jointly assigned US 2013/0319463. Alternatively a refillable reservoir may be utilized.

If desired the composition of the present invention may be used with a pre-moistened sheet. If the cleaning sheet is pre-moistened, it is preferably pre-moistened with a liquid which provides for cleaning of the target surface, such as a floor, but yet does not require a post-cleaning rinsing operation. The cleaning sheet may be loaded with at least 1, 1.5 or 2 grams of cleaning solution per gram of dry substrate, but typically not more than 5 grams per gram. The cleaning solution may comprise a surfactant, such as APG surfactant which minimizes streaking since there is typically not a rinsing operation, according to the teachings of commonly assigned U.S. Pat. No. 6,716,805.

The composition of the present invention may be used for raised hard surfaces, as is sold by the instant assignee under the names Mr. Clean and Mr. Proper. The composition may be dispensed from a trigger sprayer or aerosol sprayer, as are well known in the art. An aerosol sprayer dispenses the composition using propellant pressure, while a trigger sprayer dispenses the composition by pumping the composition under manual actuation. A suitable aerosol dispenser may have a dip tube or bag on valve, and be accord to commonly assigned US 2015/0108163 and/or US 2011/0303766. A suitable trigger sprayer may be accord to commonly assigned U.S. Pat. No. 8,322,631.

Adjunct Materials

While not essential for the purposes of the present invention, the non-limiting list of adjuncts illustrated hereinafter are suitable for use in the air freshening compositions and may be desirably incorporated in certain aspects of the invention, for example to assist or enhance phase stability of the mixture, to assist or enhance delivery of the freshening composition to fabric, to prevent degradation of the freshening composition for example by oxidation, to add additional benefits, or to modify the aesthetics of the composition as is the case with perfumes, colorants, dyes or the like. The precise nature of these additional components, and levels of incorporation thereof, will depend on the physical form of the composition and the nature of the operation for which it is to be used. Suitable adjunct materials include, but are not limited to, water, dyes, thickening agents, diluents, preservatives, solvents, insect repellents, antimicrobial agents, fragrances, aromatherapy agents, or other ingredients.

As stated, the adjunct ingredients are not essential to Applicants' compositions. Thus, certain aspects of Applicants' compositions do not contain one or more of the following adjuncts materials: water, dyes, thickening agents, diluents, preservatives, solvents, insect repellents, antimicrobial agents, fragrances, aromatherapy agents, or other ingredients. However, when one or more adjuncts are present, such one or more adjuncts may be present as detailed below.

Fragrances

Any known fragrance composition may be used in combination with the malodour reduction composition. The fragrance composition may be comprised of synthetically or naturally derived materials. Examples can comprise, but are not limited to: oil of bergamot, bitter orange, lemon, mandarin, caraway, cedar leaf, clove leaf, cedar wood, geranium, lavender, orange, origanum, petitgrain, white cedar, patchouli, neroli, rose absolute, and any other suitable materials.

Fragrance materials may also originate in the form of a crystalline solid, which has the ability to sublime into the vapour phase at ambient temperature or be used to fragrance a liquid. Any suitable amount or form can be used with the fragrance composition. For example, suitable crystalline solids can comprise, but are not limited to: vanillin, ethyl vanillin, coumarin, tonalid, calone, heliotropin, musk xylol, cedrol, musk ketone benzophenone, raspberry ketone, methyl naphthyl ketone beta, phenyl ethyl salicylate, veltol, maltol, maple lactone, isoeugenol acetate, evernyl®, and the like.

When present, fragrance materials may be present in any amount, such as from 0.1 to 99.9999% by weight of the total composition, of preferably from 10% to 99% or most preferably from 20% to 80%.

Solvent and Diluents.

Suitable solvents and diluents may be used to dilute the fragrance and/or the malodour reduction composition, or to aid in dissolution of solid fragrance or malodour reduction materials. Suitable diluents/solvents include, but are not limited to water, low molecular weight alcohols and glycols such as methanol, ethanol, isopropanol, dipropylene glycol, and diethylene glycol, glycol ethers such as dipropylene glycol methyl ether, tripropylene glycol methyl ether, dipropylene glycol methyl ether acetate, and propylene glycol n-butyl ether, esters such as those of adipic acid, benzoic acid, gluconic acid, glutaric acid, succinic acid, acetic acid, or any other suitable solvent.

When present, solvents and/or diluents may be present at any amount, such as from 0.1-90% by weight of the total composition, or preferably from 5-75% or most preferably from 10-60%.

Thickeners

It may be desirable to add a thickener to the present composition in order to control he viscosity of the composition. This may be, for example, to prevent leakage of the composition from the delivery device, to control the rate of delivery of the composition from the delivery device, or to alter the appearance of the composition. Any suitable thickener may be used including, but not limited to: cellulosic thickeners such as hydoxyethyl cellulose, hydroxypropyl methylcellulose, ethylcellulose, and hydroxypropyl cellulose, gums such as guar gum, xanthan gum, gellan gum and locust bean gum, pectin, gelatin, agar, aginic acid based thickeners, carrageenan based thickeners, polyvinyl alcohol and derivatives thereof, polymers incorporating acrylic acid or methacrylic acid and derivatives thereof, clays such as bentonite and any other suitable thickening agent, or mixtures thereof.

When present, thick thickener may be present at any amount, such as from 0.0001 to 20% by weight of the total composition, or preferably from 0.001 to 10% or most preferably from 0.01 to 5%.

Optionally, adjuvants can be added to the freshening composition herein for their known purposes. Such adjuvants include, but are not limited to, insect and moth repelling agents; oil or water soluble colorants; antioxidants; aromatherapy agents and mixtures thereof.

The freshening composition may include other malodor reducing technologies in addition to the malodor reduction composition of the current invention. This may include, without limitation, amine functional polymers, metal ions, cyclodextrins, cyclodextrin derivatives, polyols, oxidizing agents, activated carbon, reactive aldehyde, ionones, and combinations thereof.

Air and Fabric Refreshing Delivery Forms

The present composition may be used in a device for the delivery of a volatile material to the atmosphere or on inanimate surfaces (e.g. fabric surfaces as a fabric refresher). Such device may be configured in a variety of ways.

For example, the device may be configured for use as an energized air freshener (i.e. powered by electricity; or chemical reactions, such as catalyst fuel systems; or solar powered; or the like). Exemplary energized air freshening devices include a powered delivery assistance means which may include a heating element, a piezo element, thermal ink jet element, fan assembly, or the like. More particularly, the device may be an electrical wall-plug air freshener as described in U.S. Pat. No. 7,223,361; a battery (including rechargeable battery) powered air freshener having a heating and/or fan element. In energized devices, the volatile material delivery engine may be placed next to the powered delivery assistance means to diffuse the volatile perfume material. The volatile perfume material may be formulated to optimally diffuse with the delivery assistance means.

The device may be configured for use as a non-energized air freshener. An exemplary non-energized air freshener includes a reservoir and, optionally, capillary or wicking means or an emanating surface, to help volatile materials passively diffuse into the air (i.e. without an energized means). A more specific example includes a delivery engine having a liquid reservoir for containing a volatile material and a microporous membrane enclosing the liquid reservoir as disclosed in U.S. Pat. Nos. 8,709,337 and 8,931,711.

The device may also be configured for use as an aerosol sprayer or a non-aerosol air sprayer including traditional trigger sprayers as well as trigger sprayer having a pre-compression and/or buffer system for fluid therein. In this embodiment, the delivery engine can deliver volatile materials upon user demand or programmed to automatically deliver volatile materials to the atmosphere.

The apparatus may also be configured for use with an air purifying system to deliver both purified air and volatile materials to the atmosphere. Non-limiting examples include air purifying systems using ionization and/or filtration technology for use in small spaces (e.g. bedrooms, bathrooms, automobiles, etc.), and whole house central air conditioning/heating systems (e.g. HVAC).

Test Methods

Malodor reduction materials may be separated from mixtures, including but not limited to finished products such as consumer products and indentified, by analytical methods that include GC-MS and/or NMR.

Test Method for Determining Saturation Vapour Pressure (VP)

The saturation Vapour Pressure (VP) values are computed for each PRM in the perfume mixture being tested. The VP of an individual PRM is calculated using the VP Computational Model, version 14.02 (Linux) available from Advanced Chemistry Development Inc. (ACD/Labs) (Toronto, Canada) to provide the VP value at 25° C. expressed in units of torr. The ACD/Labs' Vapor Pressure model is part of the ACD/Labs model suite.

Test Method for Determining the Logarithm of the Octanol/Water Partition Coefficient (log P)

The value of the log of the Octanol/Water Partition Coefficient (log P) is computed for each PRM in the perfume mixture being tested. The log P of an individual PRM is calculated using the Consensus log P Computational Model, version 14.02 (Linux) available from Advanced Chemistry Development Inc. (ACD/Labs) (Toronto, Canada) to provide the unitless log P value. The ACD/Labs' Consensus log P Computational Model is part of the ACD/Labs model suite.

Test Method for the Generation of Molecular Descriptors

In order to conduct the calculations involved in the computed-value test methods described herein, the starting information required includes the identity, weight percent, and molar percent of each PRM in the perfume being tested, as a proportion of that perfume, wherein all PRMs in the perfume composition are included in the calculations. Additionally for each of those PRMs, the molecular structure, and the values of various computationally-derived molecular descriptors are also required, as determined in accordance with the Test Method for the Generation of Molecular Descriptors described herein.

For each PRM in a perfume mixture or composition, its molecular structure is used to compute various molecular descriptors. The molecular structure is determined by the graphic molecular structure representations provided by the Chemical Abstract Service ("CAS"), a division of the American Chemical Society, Columbus, Ohio, U.S.A. These molecular structures may be obtained from the CAS Chemical Registry System database by looking up the index name or CAS number of each PRM. For PRMs, which at the time of their testing are not yet listed in the CAS Chemical Registry System database, other databases or information sources may be used to determine their structures. For a PRM which has potentially more than one isomer present, the molecular descriptor computations are conducted using the molecular structure of only one of the isomers, which is selected to represent that PRM. The selection of isomer is determined by the relative amount of extension in the molecular structures of the isomers. Of all the isomers of a given PRM, it is the isomer whose molecular structure that is the most prevalent which is the one that is selected to represent that PRM. The structures for other potential isomers of that PRM are excluded from the computations. The molecular structure of the isomer that is the most prevalent is paired with the concentration of that PRM, where the concentration reflects the presence of all the isomers of that PRM that are present.

A molecule editor or molecular sketching software program, such as ChemDraw (CambridgeSoft/PerkinElmer Inc., Waltham, Mass., U.S.A.), is used to duplicate the 2-dimensional molecular structure representing each PRM. Molecular structures should be represented as neutral species (quaternary nitrogen atoms are allowed) with no disconnected fragments (e.g., single structures with no counter ions). The winMolconn program described below can convert any deprotonated functional groups to the neutral form by adding the appropriate number of hydrogen atoms and will discard the counter ion.

For each PRM, the molecular sketching software is used to generate a file which describes the molecular structure of the PRM. The file(s) describing the molecular structures of the PRMs is subsequently submitted to the computer software program winMolconn, version 1.0.1.3 (Hall Associates Consulting, Quincy, Mass., U.S.A., www.molconn.com), in order to derive various molecular descriptors for each PRM. As such, it is the winMolconn software program which dictates the structure notations and file formats that are acceptable options. These options include either a MACCS SDF formatted file (i.e., a Structure-Data File); or a Simplified Molecular Input Line Entry Specification (i.e., a SMILES string structure line notation) which is commonly used within a simple text file, often with a ".smi" or ".txt" file name extension. The SDF file represents each molecular structure in the format of a multi-line record, while the syntax for a SMILES structure is a single line of text with no white space. A structure name or identifier can be added to the SMILES string by including it on the same line following the SMILES string and separated by a space, e.g.: C1=CC=CC=C1 benzene.

The winMolconn software program is used to generate numerous molecular descriptors for each PRM, which are then output in a table format. Specific molecular descriptors derived by winMolconn are subsequently used as inputs (i.e., as variable terms in mathematical equations) for a variety of computer model test methods in order to calculate values such as: saturation Vapour Pressure (VP); Boiling Point (BP); logarithm of the Octanol/Water Partition Coefficient (log P); Odour Detection Threshold (ODT); Malodour Reduction Value (MORV); and/or Universal Malodour Reduction Value (Universal MORV) for each PRM. The molecular descriptor labels used in the models' test method computations are the same labels reported by the winMolconn program, and their descriptions and definitions can be found listed in the winMolconn documentation. The following is a generic description of how to execute the winMolconn software program and generate the required molecular structure descriptors for each PRM in a composition.

Computing Molecular Structure Descriptors Using winMolconn:
1) Assemble the molecular structure for one or more perfume ingredients in the form of a MACCS Structure-Data File, also called an SDF file, or as a SMILES file.
2) Using version 1.0.1.3 of the winMolconn program, running on an appropriate computer, compute the full complement of molecular descriptors that are available from the program, using the SDF or SMILES file described above as input.
    a. The output of winMolconn is in the form of an ASCII text file, typically space delimited, containing the structure identifiers in the first column and respective molecular descriptors in the remaining columns for each structure in the input file.
3) Parse the text file into columns using a spreadsheet software program or some other appropriate technique. The molecular descriptor labels are found on the first row of the resulting table.
4) Find and extract the descriptor columns, identified by the molecular descriptor label, corresponding to the inputs required for each model.
    a. Note that the winMolconn molecular descriptor labels are case-sensitive.

MORV and Universal MORV Calculation
1.) Input Molecular Descriptor values as determined via the method above into the following four equations:

$$MORV = -8.5096 + 2.8597 \times (dxp9) + 1.1253 \times (knotpv) - 0.34484 \times (e1C2O2) - 0.00046231 \times (idw) + 3.3509 \times (idcbar) + 0.11158 \times (n2pag22) \quad \text{a)}$$

$$MORV = -5.2917 + 2.1741 \times (dxvp5) - 2.6595 \times (dxvp8) + 0.45297 \times (e1C2C2d) - 0.6202 \times (c1C2O2) + 1.3542 \times (CdCH2) + 0.68105 \times (CaasC) + 1.7129 \times (idcbar) \quad \text{b)}$$

$$MORV = -0.0035 + 0.8028 \times (SHCsatu) + 2.1673 \times (xvp7) - 1.3507 \times (c1C1C3d) + 0.61496 \times (c1C1O2) + 0.00403 \times (idc) - 0.23286 \times (nd2) \quad \text{c)}$$

$$MORV = -0.9926 - 0.03882 \times (SdO) + 0.1869 \times (Ssp3OH) + 2.1847 \times (xp7) + 0.34344 \times (e1C3O2) - 0.45767 \times (c1C2C3) + 0.7684 \times (CKetone) \quad \text{d)}$$

Equation a) relates a material's effectiveness in reducing the malodor trans-3-methyl-2-hexenoic acid (carboxylic acid based malodors)
Equation b) relates a material's effectiveness in reducing the malodor trimethylamine (amine based malodors)
Equation c) relates a material's effectiveness in reducing the malodor 3-mercapto-3-methylhexan-1-ol (thiol based malodors)
Equation d) relates a material's effectiveness in reducing the malodor skatole (indole based malodors)
2.) For purpose of the present application, a material's MORV is the highest MORV value from equations 1.)a) through 1.)d).

3.) If all MORV values from equations 1.)a) through 1.)d) above are greater than 0.5, the subject material has a Universal MORV.

Method for Assigning Fragrance Fidelity Index (FFI) and the Blocker Index (BI) for a Malodor Reduction Compound Blocker materials suitable for use in consumer products of the present invention are chosen for their ability to decrease malodor, while not interfering with perception of a fragrance. Material selection is done by assigning two indices to a test sample material from two reference scales in order to rank odor strengths. The two reference scales are the Fragrance Fidelity Index (FFI) scale and the Blocker Index (BI) scale. The FFI ranks the ability of the test sample material to impart a perceivable odor which could cause interference when combined with another fragrance and the BI ranks the ability of the test sample material to reduce malodor perception. The two methods for assigning the indices to a test sample on the FFI and the BI reference scales are given below.

Method for Assigning the FFI to Test Samples

The first step in the method for assigning an FFI to the test samples on the FFI reference scale is to create the FFI reference swatches. The swatches for the scale are created by treating clean fabrics swatches with a known amount of a known concentration of an ethyl vanillin solution. Fabric swatches for this test are white knit polycotton (4 inch×4 inch) swatches from EMC ordered as PC 50/50. The supplier is instructed to strip the swatches first, stripping involves washing twice with a fragrance-free detergent and rinsing three times.

Making the FFI Reference Swatches

Make three solutions of ethyl vanillin using a 50%/50% EtOH/water as the diluent at the following concentrations: 25 ppm, 120 ppm and 1000 ppm. Pipette 13 µL of each of the three solutions into the middle of a clean swatch resulting in about a 1 cm diameter of the solution in the middle of the swatch. This will create a sensory scale of three swatches with three different odor levels based on the concentration of the solution pipetted onto the swatch. After drying for 30 minutes in a vented hood, the swatches are wrapped in aluminum foil to prevent odor contamination to the treated swatch. A clean untreated swatch is also included as the lowest anchor point of reference for odor strength on the FFI scale. The FFI reference scale swatches should be used within 0.5 to 12 hours and discarded after 12 hours. The swatches are used as scale anchor points when graders evaluate a test sample(s) and are assigned a Fragrance Fidelity Index (FFI) as show in Table 7.

At least four perfumers/expert graders are used to rank the ethyl vanillin swatches in the FFI scale. The perfumer/expert grader needs to demonstrate adequate discrimination on the scale. The perfumer/expert panel is asked to rank order swatches according to a scale between 0 and 3. The panel must demonstrate statistical differences between the swatches as seen in Table 7.

TABLE 7

Results FFI of reference swatches from six perfumers/expert graders.

| FFI | Swatch | Expert Grader 1 | 2 | 3 | 4 | 5 | 6 | Ave | Std Dev. |
|---|---|---|---|---|---|---|---|---|---|
| 0 | Control: stripped swatch NIL ethyl vanillin | 0 | 0 | 0.5 | 0 | 0 | 0 | 0.08 | 0.2 |
| 1 | Stripped swatch with 13 µL 25 ppm ethyl vanillin | 0.5 | 0.5 | 0.5 | 1.5 | 0.5 | 1.0 | 0.75 | 0.4 |

TABLE 7-continued

Results FFI of reference swatches from six perfumers/expert graders.

| | | Expert Grader | | | | | | | |
|---|---|---|---|---|---|---|---|---|---|
| FFI | Swatch | 1 | 2 | 3 | 4 | 5 | 6 | Ave | Std Dev. |
| 2 | Stripped swatch with 13 μL 120 ppm ethyl vanillin | 2.0 | 1.5 | 1.5 | 2.0 | 2.0 | 2.0 | 1.8 | 0.2 |
| 3 | Stripped swatch with 13 μL 1000 ppm ethyl vanillin | 3.0 | 2.0 | 3.0 | 3.0 | 3.0 | 3.0 | 2.8 | 0.4 |

The expert graders must demonstrate a full range of 2.5 over the 4 swatches to be acceptably discriminating. Grader 2 in table 1 has a range of only 2 and is eliminated from the panel. The panel of expert graders must also demonstrated the ability to statistically discriminate between swatches in the scale.

TABLE 8

This table demonstrates acceptable expert graders with an acceptable range and the panel meets the requirement for discriminating statistics.

| | | Expert Grader | | | | | | |
|---|---|---|---|---|---|---|---|---|
| FFI | Swatch | 1 | 3 | 4 | 5 | 6 | Ave | Std Dev. |
| 0 | Control: stripped swatch NIL ethyl vanillin | 0 | 0.5 | 0 | 0 | 0 | 0.08 | 0.2 |
| 1 | Stripped swatch with 13 μL 25 ppm ethyl vanillin | 0.5 | 0.5 | 1.5 | 0.5 | 1.0 | 0.80 | 0.4 |
| 2 | Stripped swatch with 13 μL 120 ppm ethyl vanillin | 2.0 | 1.5 | 2.0 | 2.0 | 2.0 | 1.9 | 0.2 |
| 3 | Stripped swatch with 13 μL 1000 ppm ethyl vanillin | 3.0 | 3.0 | 3.0 | 3.0 | 3.0 | 3.0 | 0.0 |

The reference swatches represent the 0, 1, 2, and 3 FFIs on the FFI reference scale, Table 9. The expert grader should familiarize them self with the strength of the odor on the FFI reference swatches by sniffing each one starting at 0 (the lowest odor strength) and ending at 3 (the highest odor strength). This should be done prior to evaluating the test sample material treated swatch.

TABLE 9

Swatch treatments comprising the Fragrance Fidelity Index (FFI) reference scale

| Swatch treatment | Conc. of ethyl vanillin | FFI |
|---|---|---|
| Clean fabric swatch w/13 μL ethyl vanillin | 1000 ppm ethyl vanillin | 3 |
| Clean fabric swatch w/13 μL ethyl vanillin | 120 ppm ethyl vanillin | 2 |
| Clean fabric swatch w/13 μL ethyl vanillin | 25 ppm ethyl vanillin | 1 |
| Clean fabric swatch NIL ethyl vanillin | NIL ethyl vanillin | 0 |

Making Swatches Treated with the Test Material

A clean swatch is treated with 13 μL of a known concentration of a test sample material resulting in an about 1 cm of the solution on the clean swatch. Just like the reference swatches, the test sample material swatch is dried in a vented hood for 30 minutes and then wrapped in aluminum foil to prevent contamination. The test material swatches and the FFI reference swatches should be made within 2 hrs of each other. The test material swatch must be used within 0.5 to 12 hours and discarded after 12 hours.

Assigning the FFI to the Test Material

At least two perfumers/expert graders are used to assign an FFI grade to a test sample. The perfumer/expert grader smells the test sample swatch by holding that swatch 1 inch from their nose with their nose centered over the area where the test sample was pipetted on to the fabric and then assigns the test sample an FFI grade using the FFI reference scale anchor swatches as references. The test sample swatch is assigned an FFI grade at or between numbers on the FFI scale shown in Table 9. In cases where the test sample material is graded greater than 3, the test material is not a blocker material or the concentration of the material needs to be lowered and reevaluated to determine if a lower level has a malodor blocker functionality.

Method for Assigning the BI to Test Sample

The first step in the method for assigning a BI to a test sample material on the BI reference scale is to create the BI reference swatches. The swatches for the scale are created by treating clean fabrics swatches with a known amount of a known volume of isovaleric acid solution at a known concentration. Fabric swatches for this test are white knit polycotton (4 inch×4 inch) swatches from EMC ordered as PC 50/50. The supplier is instructed to strip the swatches first, stripping involves washing twice with a fragrance-free detergent and rinsing three times.

Making the BI Reference Swatches

Make one solution of 0.08% isovaleric acid using 50%/50% EtOH/water as the diluent. The BI scale contains one clean swatch with no malodor applied. Three other swatches each have a different volume of the 0.08% isovaleric acid applied. Pipette 2 μL of the 0.08% isovaleric acid solution to one clean swatch, 5 μL of the 0.08% isovaleric acid solution to the next swatch and 20 μL of isovaleric acid to the final clean swatch. These solutions are pipetted to the middle of the swatches. This will create a sensory scale of three swatches with three different odor levels based on the volume of the 0.08% isovaleric acid solution pipetted onto the swatch. After drying for 30 minutes in a vented hood, the swatches are wrapped in aluminum foil to prevent odor contamination to the treated swatch. A clean untreated swatch is also included as the lowest anchor point of reference for malodor strength on the BI scale. The BI reference scale swatches should be used within 0.5 to 12 hours and discarded after 12 hours. The swatches are used as scale anchor points when graders evaluate a test sample(s) and are assigned a Blocker Index (BI) as show in Table 12.

At least four perfumers/expert graders are used to rank the isovaleric acid swatches in the BI scale. The perfumer/expert grader needs to demonstrate adequate discrimination on the scale. The perfumer/expert grader is asked to rank order swatches according to a scale between 0 and 3. The panel of graders must demonstrate statistical differences between the swatches as seen in Table 10.

TABLE 10

Results from six perfumers/expert graders to create the BI scale.

| | | Expert Grader | | | | | | Std |
|---|---|---|---|---|---|---|---|---|
| BI | Swatch | 1 | 2 | 3 | 4 | 5 | Ave | Dev. |
| 0 | Control: stripped swatch NIL isovaleric acid | 0 | 0 | 0 | 0 | 0 | 0 | 0 |
| 1 | Stripped swatch with 2 μL 0.08% isovaleric acid | 0.5 | 2.0 | 1.0 | 1.0 | 0.5 | 1.0 | 0.5 |
| 2 | Stripped swatch with 5 μL 0.08% isovaleric acid | 2.0 | 2.5 | 2.0 | 2.0 | 2.0 | 2.1 | 0.2 |
| 3 | Stripped swatch with 20 μL 0.08% isovaleric acid | 3.0 | 3.0 | 3.0 | 3.0 | 2.5 | 2.8 | 0.2 |

The expert graders must demonstrate a full range of 2.5 over the 4 swatches to be acceptably discriminating. The panel of expert graders must also demonstrated the ability to statistically discriminate between swatches in the scale. Expert grader #2 did not demonstrate the ability to discriminate between the swatches and is eliminated from the panel, see Table 11.

TABLE 11

This table demonstrates acceptable expert graders with an acceptable range and the panel meets the requirement for discriminating statistics.

| | | Expert Grader | | | | | |
|---|---|---|---|---|---|---|---|
| BI | Swatch | 1 | 3 | 4 | 5 | Ave | Std Dev. |
| 0 | Control: stripped swatch NIL isovaleric acid | 0 | 0 | 0 | 0 | 0 | 0 |
| 1 | Stripped swatch with 2 μL 0.08% isovaleric acid | 0.5 | 1.0 | 1.0 | 0.5 | 0.8 | 0.3 |
| 2 | Stripped swatch with 5 μL 0.08% isovaleric acid | 2.0 | 2.0 | 2.0 | 2.0 | 2.0 | 0 |
| 3 | Stripped swatch with 20 μL 0.08% isovaleric acid | 3.0 | 3.0 | 3.0 | 2.5 | 2.9 | 0.2 |

The reference swatches represent the 0, 1, 2, and 3 BIs on the BI reference scale, Table 12. The expert grader should familiarizes him/herself with the strength of the odor on the BI reference swatches by sniffing each one starting at 0 (the lowest odor strength) and ending at 3 (the highest odor strength). This should be done prior to evaluating the swatch treated with the test material.

TABLE 12

Swatch treatments comprising the Blocker Index (BI) reference scale.

| Swatch/treatment | Wt of isovaleric acid | BI |
|---|---|---|
| Clean fabric swatch w/20 μL 0.08% isovaleric acid | 16 mg isovaleric acid | 3 |
| Clean fabric swatch w/5 μL 0.08% isovaleric acid | 4 mg isovaleric acid | 2 |
| Clean fabric swatch w/2 μL 0.08% isovaleric acid | 1.6 mg isovaleric acid | 1 |
| Clean fabric swatch NIL isovaleric acid | NIL isovaleric acid | 0 |

Making the Malodorous Swatch and Treating it with a Test Material

To evaluate the BI, the test material is applied to a malodorous swatch to determine how well the test material blocks the malodor. The malodorous swatch is made by treating a clean swatch with 20 μL of a 0.08% solution of isovaleric acid. Dry the malodorous swatch treated with isovaleric acid in a vented hood for 30 minutes. After drying the malodorous swatch a known concentration of test material solution, between 1 ppm and 100 ppm is pipetted onto the malodorous swatch. Apply the test material solution right on top of the spot where the isovaleric acid solution was applied making an about 1 cm diameter spot. Just like the BI reference swatches, the isovaleric acid+test material swatch is dried in a vented hood for 30 minutes and then wrapped in aluminum foil to prevent contamination. The isovaleric acid+test material swatches and the BI reference swatches should be made within 2 hrs of each other. The isovaleric acid+test material swatch must be used between 1-12 hours just like the reference swatches. It is sometimes necessary to evaluate several levels of the test material between about 1 and about 100 ppm to determine the BI.

Assigning the BI to the Test Material

At least two perfumers/expert graders are used to assign the BI to the test sample. The expert grader smells the isovaleric acid+test material swatch by holding that swatch one inch from their nose with their nose centered over the area where the test sample was pipetted on to the fabric and then assigns the isovaleric acid+test material swatch a BI based on ranking its odor strength against the odor strength of the swatches in the BI reference scale. The test sample swatch is assigned a BI at or between numbers on the BI in table. In cases where the isovaleric acid+test material swatch odor is greater than 3 on the BI reference scale, this indicates the material is not a blocker or the concentration of the test material needs to be lowered to achieve its blocker functionality.

Malodor Reduction Compounds with FFI and BI Grades Based on the Aforementioned

| Table Ref # | CAS# | log P | Name | Conc | FFI | BI |
|---|---|---|---|---|---|---|
| 281 | 54830-99-8 | 3.11 | 3a,4,5,6,7,7a-hexahydro-4,7-methano-1H-indenyl acetate | 10 ppm | 0 | 2.0 |
|  |  |  |  | 50 ppm | 0.5 | 2.0 |
| 677 | 139504-68-0 | 3.75 | 1-((2-(tert-butyl)cyclohexyl)oxy)butan-2-ol | 10 ppm | 0 | 2.3 |
|  |  |  |  | 50 ppm | 1.8 | 2.0 |
| 962 | 55066-48-3 | 3.17 | 3-methyl-5-phenylpentan-1-ol | 10 ppm | 0 | 2.3 |
|  |  |  |  | 50 ppm | 0.5 | 1.7 |
| 261 | 173445-65-3 | 3.29 | 3-(3,3-dimethyl-2,3-dihydro-1H-inden-5-yl)propanal | 10 ppm | 0 | 1.8 |
|  |  |  |  | 50 ppm | 1.3 | 1.3 |
| 1139 | 87731-18-8 | 2.11 | (Z)-cyclooct-4-en-1-yl methyl carbonate | 10 ppm | 0 | 2.0 |
|  |  |  |  | 50 ppm | 1.0 | 2.7 |
|  | 4430-31-3 | 1.43 | 3,4,4a,5,6,7,8,8a-octahydrochromen-2-one | 10 ppm | 0 | 2.0 |
|  |  |  |  | 50 ppm | 0 | 2.0 |
| 204 | 40379-24-6 | 3.89 | 7-methyloctyl acetate | 10 ppm | 0 | 2.0 |
|  |  |  |  | 50 ppm | 0 | 2.7 |
| 1005 | 93981-50-1 | 5.59 | ethyl (2,3,6-trimethylcyclohexyl) carbonate | 50 ppm | 0.5 | 2.6 |
| 391 | 106-33-2 | 5.73 | Ethyl laurate | 50 ppm | 0.3 | 2.2 |
| 1148 | 1139-30-6 | 4.06 | Caryophyllene Oxide | 50 ppm | 0.5 | 2.3 |
| 524 | 13877-91-3 3338-55-4 | 4.31 | 3,7-Dimethyl-1,3,6-Octatriene(cis-β ocimene 70%) | 50 ppm | 0 | 2.8 |
| 1149 | 23787-90-8 | 4 | 1,3,4,6,7,8alpha-hexahydro-1,1,5,5-tetramethyl-2H-2,4alpha-methanophtalen-8(5H)-one | 10 ppm | 0 | 1.5 |
|  |  |  |  | 50 ppm | 0.8 | 2.3 |
|  | 112-42-5 | 4.62 | Undecanol | 50 ppm | 0.8 | 2.3 |
| 174 | 112-53-8 | 5.17 | 1-dodecanol | 50 ppm | 0.5 | 2.3 |
|  | 98-52-2 | 2.78 | 4-tert-butyl cyclohexane | 10 ppm | 0 | 2.0 |
|  |  |  |  | 50 ppm | 0.3 | 2.0 |
| 109 | 112-39-0 | 6.41 | Methyl palmitate | 10 ppm |  | 2.0 |

Malodor Control Compounds with Improved Performance at Lower Levels.

Below are some non-limiting examples of preferred behavior by which the malodor control compound gives improved malodor control at lower concentration. These nonlimiting data provide additional compelling data that malodor is being blocked, not masked.

| Table Ref # | CAS# | Name | Conc | FFI | BI |
|---|---|---|---|---|---|
| N/A | 68912-13-0 | 8,8-dimethyl-3a,4,5,6,7,7a-hexahydro-1H-4,7-methanoinden-6-yl propionate | 10 ppm | 0 | 1.5 |
|  |  |  | 50 ppm | 0 | 2.2 |
| N/A | TBD | 4,8-dimethyl-1-(methylethyl)-7-oxybiciclo[4.3.0]nonane | 10 ppm |  | 2.0 |
|  |  |  | 50 ppm | 0.3 | 2.2 | about 0.001 Fragrance Fidelity
72727272727272727272727272727272727272727272727
272727272727272727272727272727272
727272727272727272727272727272727272727272727272727
272727272727272727272727272727272
7272727272727272727272727272727272

Retesting Malodor Reduction Compounds at Lower Levels.

The example below demonstrates that while a malodor control compound could fail to demonstrate odor blocking (BI>2.5) at a higher concentration it should be retested at a lower concentration to determine if it passes.

| Table Ref # | CAS # | Name | Conc | FFI | BI |
|---|---|---|---|---|---|
| N/A | 173445-65-3 | 1H-Indene-5-propanal, 2,3-dihydro-3,3-dimethyl- | 10 ppm | 0 | 1.5 |
|  |  |  | 50 ppm | 0.5 | 2.7 |

EXAMPLE 1

Compositions Comprising Malodor Reduction Compounds

In the present invention blends enable more potent malodor reduction because blends are useful at a higher % of the product composition before becoming olfactively noticeable. Below are non-limiting examples of malodor reduction compounds.

| Component | CAS# | % wt Active | | | | |
|---|---|---|---|---|---|---|
|  |  | A | B | C | D | E |
| 2,2,8,8-tetramethyl-octahydro-1H-2,4a-methanonapthalene-10-one | 29461-14-1 | 35-45 | 15-25 | 5-20 | 10-30 | 15-25 |
| 1H-Indene-ar-propanal,2,3-dihydro-1,1-dimethyl- | 300371-33-9 | 10-20 | 1-30 | NIL | 5-10 | 1-5 |
| Hexadecanoic acid, (2E)-3,7-dimethyl-2,6-octadien-1-yl ester | 3681-73-0 | 35-45 | 10-25 | NIL | 30-40 | 35-50 |

-continued

| Component | CAS# | % wt Active | | | | |
|---|---|---|---|---|---|---|
| | | A | B | C | D | E |
| 1-Pentanol-3-methyl-5-phenyl | 55066-48-3 | 10-20 | 10-25 | 2-10 | 5-17 | 10 |
| 4,7-Methano-1H-inden-5-ol, 3a,4,5,6,7,7a-hexahydro-, 5-acetate | 171102-41-3 | 0-5 | 10-25 | NIL | 1-6 | 1-5 |
| 4,8-dimethyl-1-(methylethyl)-7-oxybiciclo [4.3.0]nonane | N/A | 0-5 | NIL | NIL | NIL | 1-5 |
| (3Z)-3,7-dimethylocta-1,3,6-triene | 3338-55-4 | NIL | NIL | 10-20 | 2-5 | NIL |
| 1H-Indene-5-propanal, 2,3-dihydro-3,3-dimethyl- | 173445-65-3 | NIL | NIL | NIL | 7.5-16 | 1-15 |
| 3,4,4a,5,6,7,8,8a-octahydrochromen-2-one | 4430-31-3 | NIL | NIL | NIL | 3-7 | 1-15 |
| 1-(2-tert-butylcyclohexyl)oxybutan-2-ol | 139504-68-0 | NIL | NIL | NIL | 0.25-1.5 | NIL |
| ethyl (2,3,6-trimethylcyclohexyl) carbonate | 93981-50-1 | NIL | NIL | 15-30 | NIL | 2 |
| benzyl 2-hydroxypropanoate | 2051-96-9 | NIL | NIL | 2-5 | NIL | NIL |
| (3,5-dimethylcyclohex-3-en-1-yl)methanol | 67634-16-6 | NIL | NIL | 5-30 | NIL | NIL |
| 2-Dodecanol | 10203-28-8 | NIL | 0.25-1 | NIL | 0.5-3 | NIL |

EXAMPLE 2

Compositions Comprising Malodor Reduction Compounds

| Ingredient | CAS # | % wt Active | | | | | |
|---|---|---|---|---|---|---|---|
| | | A | B | C | B | D | E |
| (E)-1-(2,6,6-trimethyl-1-cyclohex-2-enyl)pent-1-en-3-one | 127-42-4 | 4 | 8 | 2 | 8 | 3 | 2 |
| ethyl dodecanoate | 106-33-2 | NIL | 1 | NIL | 3 | NIL | NIL |
| 3a,4,5,6,7,7a-hexahydro-1H-4,7-methanoinden-1-yl propanoate | 68912-13-0 | 8 | 30 | 1 | 4 | 1 | 3.5 |
| [1R-(1R*,4R*,6R*,10S*)]-4,12,12-trimethyl-9-methylene-5-oxatricyclo[8.2.0.04,6]dodecane | 1139-30-6 | NIL | 0.3 | 2 | 0.5 | NIL | 0.5 |
| (8E)-cyclohexadec-8-en-1-one | 3100-36-5 | NIL | 5 | NIL | 7 | NIL | NIL |
| 3,5,5-trimethylhexyl acetate | 58430-94-7 | 25 | 15 | 50 | 35 | 60 | 56 |
| ethyl (2,3,6-trimethylcyclohexyl) carbonate | 93981-50-1 | NIL | 1 | NIL | 5 | NIL | NIL |
| 2,4-dimethyl-4,4a,5,9b-tetrahydroindeno[1,2-d][1,3]dioxine | 27606-09-3 | 25 | 10 | 15 | 15 | 16 | 15 |
| 2,2,7,7-tetramethyltricyclo[6.2.1.01,6]undecan-5-one | 23787-90-8 | 8 | 9 | 5 | 7 | 5 | 5 |
| (3,5-dimethylcyclohex-3-en-1-yl)methanol | 67634-16-6 | NIL | 0.7 | NIL | 0.5 | NIL | NIL |
| 3-(7,7-dimethyl-4-bicyclo[3.1.1]hept-3-enyl)-2,2-dimethylpropanal | 33885-52-8 | 30 | 20 | 25 | 15 | 15 | 18 |
| Total | | 100 | 100 | 100 | 100 | 100 | 100 |

EXAMPLE 3

Malodor Reduction Composition

| Ingredient | CAS # | % wt Active A | B | C |
|---|---|---|---|---|
| 5-Cyclohexadecen-1-One | 37609-25-9 | 15.0 | 2.00 | 2.00 |
| decahydro-2,2,7,7,8,9,9-heptamethylindeno(4,3a-b)furan | 476332-65-7 | 0.005 | 0.01 | 0.01 |
| 2,3-Dihydro-5,6-dimethoxy-2-(4-piperidinylmethylene)-1H-inden-1-one | 33704-61-9 | 0.3 | 0.5 | 0.5 |
| Cedryl Methyl Ether | 19870-74-7 | 6.0 | 10.0 | 4.0 |
| Trans-4-Decenal | 65405-70-1 | 0.005 | 0.002 | 0.002 |
| Decyl Aldehyde | 112-31-2 | 3.74 | 2.0 | 2.0 |
| 3-methyl cyclopentadecenone | 63314-79-4 | 0.4 | 1.0 | 1.0 |
| Diphenyl Oxide | 101-84-8 | 0.5 | 1.0 | 1.0 |
| 3a,4,5,6,7,7a-hexahydro-4,7-methano-1H-indenyl acetate | 54830-99-8 | 5.0 | 8.0 | 8.0 |
| 3a,4,5,6,7,7a-hexahydro-1H-4,7-methanoinden-1-yl propanoate | 68912-13-0 | 6.0 | 8.0 | 8.0 |
| 2-(5-methyl-2-propan-2-yl-8-bicyclo[2.2.2]oct-5-enyl)-1,3-dioxolane | 68901-32-6 | 10.0 | 15.0 | 15.0 |
| (E)-3,7-dimethyl-2,6-octadienylhexadecanoate | 3681-73-0 | 10.0 | 10.0 | 16.0 |
| Iso Nonyl Acetate | 58430-94-7 | 6.65 | 8.0 | 3.0 |
| 2,2,7,7-tetramethyltricyclo[6.2.1.01,6]undecan-5-one | 23787-90-8 | 10.0 | 8.0 | 8.0 |
| (1-Methyl-2-(1,2,2-trimethylbicyclo[3.1.0]-hex-3-ylmethyl)cyclopropyl)methanol | 198404-98-7 | 0.1 | 0.3 | 0.3 |
| Lauric Aldehyde | 112-54-9 | 0.625 | 1.0 | 0.7 |
| Methyl Iso Eugenol | 93-16-3 | 18.000 | 13.0 | |
| Methyl hexadecanoate | 112-39-0 | 3.000 | 10.0 | 12.0 |
| 2,3-dihydro-1,1-1H-dimethyl-indene-ar-propanal | 300371-33-9 | 0.400 | 0.0 | 0.3 |
| 4-tert-butylcyclohexanol | 98-52-2 | 0.400 | 0.1 | 0.1 |
| 2-isobutyl-4-hydroxy-4-methyltetrahydropyran | 63500-71-0 | 1.600 | 2.0 | 2.0 |
| Undecyl Aldehyde | 112-44-7 | 1.725 | 2.888 | 1.888 |
| Undecylenic Aldehyde | 112-45-8 | 0.550 | 0.2 | 1.2 |
| Total | | 100 | 100.0 | 100.0 |

EXAMPLE 4

Malodor Reducing Compositions

Malodor Reducing Composition 4A

| | CAS# | Weight % |
|---|---|---|
| 2,2,7,7-tetramethyltricyclo(6.2.1.0(1,6))-undecan-5-one | 23787-90-8 | 40.000 |
| 3-(3,3-dimethyl-2,3-dihydro-1H-inden-5-yl)propanal | 173445-65-3 | 10.000 |
| (E)-3,7-dimethylocta-2,6-dien-1-yl palmitate | 3681-73-0 | 40.000 |
| 3-methyl-5-phenylpentan-1-ol | 55066-48-3 | 10.000 |
| 3a,4,5,6,7,7a-hexahydro-4,7-methano-1H-inden-(5 and 6)-yl acetate | 5413-60-5 | 0.000 |

Malodor Reducing Composition 4B

| | CAS# | Weight % |
|---|---|---|
| 3-(3,3-dimethyl-2,3-dihydro-1H-inden-5-yl)propanal | 3173445-65-3 | 7.500 |
| 3-(6,6-dimethylbicyclo[3.1.1]hept-2-en-2-yl)-2,2-dimethylpropanal | 33885-52-8 | 10.000 |
| 3-methyl-5-phenylpentan-1-ol | 55066-48-3 | 10.000 |
| E)-3,7-dimethylocta-2,6-dien-1-yl palmitate | 3681-73-0 | 40.000 |
| 3a,4,5,6,7,7a-hexahydro-4,7-methano-1H-inden-(5 and 6)-yl acetate | 5413-60-5 | 4.000 |
| 3,4,4a,5,6,7,8,8a-octahydrochromen-2-one | 4430-31-3 | 5.000 |
| 2,2,7,7-tetramethyltricyclo(6.2.1.0(1,6))-undecan-5-one | 23787-90-8 | 20.000 |
| (E)-3,7-dimethylocta-1,3,6-triene | 3338-55-4 | 3.000 |
| 1-((2-(tert-butyl)cyclohexyl)oxy)butan-2-ol | 139504-68-0 | 0.500 |

Malodor Reducing Composition 4C

| | CAS# | Weight % |
|---|---|---|
| 5-Cyclohexadecen-1-One | 37609-25-9 | 2.6 |
| 2,2,7,7,8,9,9-heptamethyldecahydroindeno[4,3a-b]furan | 647828-16-8 | 0.005 |

| | CAS# | Weight % |
|---|---|---|
| 1,1,2,3,3-pentamethyl-1,2,3,5,6,7-hexahydro-4H-inden-4-one | 33704-61-9 | 0.3 |
| (3R,3aR,6S,7S,8aS)-6-methoxy-3,6,8,8-tetramethyloctahydro-1H-3a,7-methanoazulene | 19870-74-7 | 6 |
| dodecanenitrile | 2437-25-4 | 0.06 |
| Trans 4-Decenal | 65405-70-1 | 0.001 |
| decanal | 112-31-2 | 3 |
| (E)-3-methylcyclopentadec-4-en-1-one | 82356-51-2 | 0.4 |
| oxydibenzene | 101-84-8 | 0.5 |
| Dipropylene Glycol | 25265-71-8 | 0.054 |
| 3a,4,5,6,7,7a-hexahydro-4,7-methano-1H-inden-(5 and 6)-yl acetate | 54830-99-8 | 4 |
| 3-(2-ethylphenyl)-2,2-dimethylpropanal | 67634-15-5 | 3 |
| 3-(3-isopropylphenyl)butanal | 125109-85-5 | 0.6 |
| 8,8-dimethyl-3a,4,5,6,7,7a-hexahydro-1H-4,7-methanoinden-6-yl propionate | 68912-13-0 | 6 |
| 2-(8-isopropyl-6-methylbicyclo[2.2.2]oct-5-en-2-yl)-1,3-dioxolane | 68901-32-6 | 10 |
| d E)-3,7-dimethylocta-2,6-dien-1-yl palmitate | 3681-73-0 | 10 |
| 7-methyloctyl acetate | 40379-24-6 | 3 |
| 2,2,7,7-tetramethyltricyclo(6.2.1.0(1,6))-undecan-5-one | 23787-90-8 | 10 |
| (1-methyl-2-((1,2,2-trimethylbicyclo[3.1.0]hexan-3-yl)methyl)cyclopropyl)methanol | 198404-98-7 | 0.1 |
| dodecanal | 112-54-9 | 0.6 |
| Linalyl Benzoate | 126-64-7 | 1.74 |
| 4-(tert-butyl)cyclohexyl acetate | 32210-23-4 | 4 |
| octahydro-1H-4,7-methanoindene-1-carbaldehyde | 30772-79-3 | 0.26 |
| methyl 2-(3-oxo-2-pentylcyclopentyl)acetate | 24851-98-7 | 4.15 |
| (Z)-1,2-dimethoxy-4-(prop-1-en-1-yl)benzene | 93-16-3 | 18.23 |
| Methyl Palmitate | 112-39-0 | 3 |
| 3-(3,3-dimethyl-2,3-dihydro-1H-inden-5-yl)propanal | 300371-33-9 | 0.4 |
| 4-tert-butyl cyclohexanol | 98-52-2 | 0.05 |
| 3-methyl-5-phenylpentan-1-ol | 55066-48-3 | 3.5 |
| 2-isobutyl-4-methyltetrahydro-2H-pyran-4-ol | 63500-71-0 | 1.6 |
| (E)-4-methyldec-3-en-5-ol | 81782-77-6 | 0.8 |
| undecanal | 112-44-7 | 1.7 |
| undec-10-enal | 112-45-8 | 0.35 |

Malodor Reducing Composition 4D (SPMB 4.11).

| | CAS# | Weight % |
|---|---|---|
| (3R,3aR,6S,7S,8aS)-6-methoxy-3,6,8,8-tetramethyloctahydro-1H-3a,7-methanoazulene | 19870-74-7 | 2.00 |
| 1-(1,2,3,4,5,6,7,8-octahydro-2,3,8,8,-tetramethyl-2-naphthyl)ethan-1-one | 54464-57-2 | 15.00 |
| Oxacyclohexadec-12-en-2-one, (12E)- | 1118-80-2 | 15.00 |
| 5-cyclohexadecenone | 37609-25-9 | 16.50 |
| 4,8-dimethyl-2-(propan-2-ylidene)-1,2,3,3a,4,5,6,8a-octahydroazulen-6-yl acetate | 117-98-6 | 5.00 |
| isopropyl tetradecanoate | 110-27-0 | 12.25 |
| (Z)-4,11,11-trimethyl-8-methylenebicyclo[7.2.0]undec-3-en-5-yl acetate | 32214-91-8 | 3.50 |
| (E)-cycloheptadec-9-en-1-one | 542-46-1 | 14.00 |
| (E)-cyclohexadec-8-en-1-one | 3100-36-5 | 14.00 |
| 4-((2R)-1,7,7-trimethylbicyclo[2.2.1]heptan-2-yl)cyclohexan-1-ol | 66072-32-0 | 2.75 |

Malodor Reducing Composition 4E

| | CAS# | Weight % |
|---|---|---|
| 3-(3,3-dimethyl-2,3-dihydro-1H-inden-5-yl)propanal | 173445-65-3 | 10.000 |
| 3-methyl-5-phenylpentan-1-ol | 55066-48-3 | 10.000 |
| 3a,4,5,6,7,7a-hexahydro-4,7-methano-1H-inden-(5 and 6)-yl acetate | 5413-60-5 | 20.000 |
| 2,2,7,7-tetramethyltricyclo(6.2.1.0(1,6))-undecan-5-one | 23787-90-8 | 20.000 |
| 7-methyloctyl acetate | 58430-94-7 | 40.000 |

Malodor Reducing Composition 4F

| | CAS# | Weight % |
|---|---|---|
| 1-((2-(tert-butyl)cyclohexyl)oxy)butan-2-ol | 139504-68-0 | 100 |

EXAMPLES 5.1-5.6

Malodor Reduction Composition

The following malodor reduction malodor reduction compositions are made by combining the listed ingredients. All ingredients are in weight percent of the total malodor reduction composition.

| Ingredient | CAS # | 5.1 | 5.2 | 5.3 | 5.4 | 5.5 | 5.6 |
|---|---|---|---|---|---|---|---|
| (E)-1-(2,6,6-trimethyl-1-cyclohex-2-enyl)pent-1-en-3-one | 127-42-4 | 4 | 8 | 2 | 8 | 3 | 2 |
| ethyl dodecanoate | 106-33-2 | 0 | 1 | 0 | 3 | 0 | 0 |
| 3a,4,5,6,7,7a-hexahydro-1H-4,7-methanoinden-1-yl propanoate | 68912-13-0 | 8 | 30 | 1 | 4 | 1 | 3.5 |
| [1R-(1R*,4R*,6R*,10S*)]-4,12,12-trimethyl-9-methylene-5-oxatricyclo[8.2.0.04,6]dodecane | 1139-30-6 | 0 | 0.3 | 2 | .5 | 0 | 0.5 |
| (8E)-cyclohexadec-8-en-1-one | 3100-36-5 | 0 | 5 | 0 | 7 | 0 | 0 |
| 3,5,5-trimethylhexyl acetate | 58430-94-7 | 25 | 15 | 50 | 35 | 60 | 56 |
| ethyl (2,3,6-trimethylcyclohexyl) carbonate | 93981-50-1 | 0 | 1 | 0 | 5 | 0 | 0 |
| 2,4-dimethyl-4,4a,5,9b-tetrahydroindeno[1,2-d][1,3]dioxine | 27606-09-3 | 25 | 10 | 15 | 15 | 16 | 15 |
| 2,2,7,7-tetramethyltricyclo[6.2.1.01,6]undecan-5-one | 23787-90-8 | 8 | 9 | 5 | 7 | 5 | 5 |

-continued

| Ingredient | CAS # | 5.1 | 5.2 | 5.3 | 5.4 | 5.5 | 5.6 |
|---|---|---|---|---|---|---|---|
| (3,5-dimethylcyclohex-3-en-1-yl)methanol | 67634-16-6 | 0 | 0.7 | 0 | .5 | 0 | 0 |
| 3-(7,7-dimethyl-4-bicyclo [3.1.1]hept-3-enyl)-2,2-dimethylpropanal | 33885-52-8 | 30 | 20 | 25 | 15 | 15 | 18 |
| Total | | 100 | 100 | 100 | 100 | 100 | 100 |

Each of the malodor reduction compositions of Examples 4A-4F and 5.1-5.6 is used as a component in an air freshening device at a level of form about 1% to about 100%. Then the consumer product is used in an air care device to treat air, and/or as a treatment composition to treat a fabric and/or hard surface.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed:

1. An air freshening composition, said composition comprising, based on total composition weight:
    a) a sum total of from about 0.0001% to about 15% of two or more malodor reduction materials selected from the group consisting of oxydibenzene, 2-isopropy 1-5-methylphenol, (Z)-non-6-en-1-ol, or combinations thereof; and
    b) optionally, from about 0.01% to about 90 of at least one solvent;
    c) optionally, an adjunct ingredient,
    wherein the composition does not comprise water.

2. A freshening compositions according to claim 1, wherein said sum total of malodor reduction materials has a Blocker Index of less than 3 and/or a Blocker Index average of 3 to about 0.001.

3. A freshening compositions according to claim 2, wherein each of said malodor reduction materials has a Malodour Reduction Value ("MORV") of at least 0.5.

4. A freshening compositions according to claim 1, wherein each of said malodor reduction materials has a Malodour Reduction Value ("MORV") of at least 0.5.

5. A freshening composition according to claim 1 wherein, said sum total of malodor reduction materials has a Fragrance Fidelity Index average of 3 to about 0.001 each malodor reduction material in said sum total of malodor reduction materials has a Fragrance Fidelity Index of less than 3.

6. A freshening composition according to claim 1 further comprising one or more additional malodor materials selected from the group consisting of 1,1-dimethoxynon-2-yne; 2-(p-tolyl)propan-2- ol; 3-methoxy-7,7-dimethyl-10-methylenebicyclo[4.3.1]decane; methoxycyclododecane; 4-(tert-pentyl)cyclohexan-1-one; 7-isopropyl-8,8-dimethyl-6,10-dioxaspiro[4.5]decane; octyl acetate; 2-heptyl-4-methyl-1,3-dioxolane; octanal; 1,1-dimethoxyoctane; 7-methyl-3-methyleneocta-1,6-diene; 2-methyl-6-methyleneoct-7-en-2-ol; 2-methyl-6-methyleneoct-7-en-2-yl acetate; (E)-2,6-dimethylocta-5,7-dien-2-ol; nonan-1-ol; nonanal; 2-methoxynaphthalene; (Z)-3,7-dimethylocta-2,6-dien-1-ol; 1-ethyl-3-methoxytricyclol[2.2.1.02,6]heptane; methyl (E) -non-2-enoate; 6,6-dimethylbicyclo[3.1.1]hept-2-ene-2-carbaldehyde; methyl non-2-ynoate; 2-methyldecanal; 6,6-dimethoxy-2,5,5-trimethylhex-2-ene; 4-phenylbutan-2-ol; 1,1-dimethoxy-2-methylundecane; undec an-2-one; 2-methylundecanal; (Z)-1,2-dimethoxy-4-(prop-1-en-1-yl)benzene; 4-allyl-1,2-dimethoxybenzene; 1-methyl-2-phenoxybenzene; methyl cinnamate; 1-allyl-4-methoxybenzene; methyl oct-2-ynoate; methyl 2,6,6-trimethylcyclohex-2-ene-1-carboxylate; 7-methoxy-3,7-dimethyloctanal; octahydro-1H-4,7-methanoindene-1-carbaldehyde; 8-isopropyl-6-methylbicyclo [2.2.2]oct-5-ene-2-carbaldehyde; (S)-1-methyl-4-(prop-1-en-2-yl) cyclohex-1-ene; (Z)-3-hexen-1-yl-2-cyclopenten-1-one; 3,7-dimethylocta-1,6-dien-3-yl isobutyrate; 2-(5-methyl-5-vinyltetrahydrofuran-2-yl)propan-2-ol; 3-(4-methylcyclohex-3-en-1-yl)butanal; (E)-1-(1-methoxypropoxy)hex-3-ene; (E)-1-(1-ethoxyethoxy)hex-3-ene; (1S,5R)-2-methyl-5-(prop-1-en-2-yl)cyclohex-2-en-1-ol; dodecanal; 2-propylheptanenitrile; 2-hexylcyclopentan-1-one; 2-methyl-4-phenyl-1,3-dioxolane; 2,6,9,10-tetramethyl-1-oxaspiro(4.5)deca-3,6-diene; (1R,2S,5R)-5-methyl-2-(prop-1-en-2-yl)cyclohexan-1-ol; (2S,5S)-2-isopropyl-5-methylcyclohexan-1-one; 2-hexylcyclopent-2-en-1-one; (2S,5S)-2-isopropyl-5-methylcyclohexan-1-one; 2,5,6-trimethylcyclohex-3-ene-1-carbaldehyde; (1R,2R,4S)-1,7,7-trimethylbicyclo[2.2.1]heptan-2-yl propionate; (1S,2S,4S)-1,7,7-trimethylbicyclo[2.2.1]heptan-2-yl isobutyrate; (1R,4S)-1,7,7-trimethylbicyclo[2.2.1]heptan-2-yl acetate; (E)-non-2-enenitrile; 3-phenylpropan-1-ol; (1,1-dimethoxypropan-2-yl)benzene; 5-ethyl-4-hydroxy-2-methylfuran-3 (2H)-one; hexyl hexanoate; (Z)-hex-1-en-1-yl (Z)-2-methylbut-2-enoate; 2-butyl-4,4,6-trimethyl-1,3-dioxane; ethyl (1R,2R,3R,4R)-3-isopropylbicyclo[2.2.1]hept-5-ene-2-carboxylate; 3a,4,5,6,7,7a-hexahydro-1H-4,7-methanoinden-6-yl acetate; 6-butyl-2,4-dimethyl-3,6-dihydro-2H-pyran; ethyl 2-ethyl-6,6-dimethylcyclohex-2-ene-1-carboxylate; 1-methyl-4-(propan-2-ylidene)cyclohexyl acetate; 1-methyl-4-(propan-2-ylidene)cyclohexan-1-ol; (1R,4aR,8aS)-1-isopropyl-7-methyl-4-methylene-1,2,3,4,4a,5,6,8a-octahydronaphthalene; (4aS,9aR)-3,5,5,9-tetramethyl-2,4a,5,6,7,9a-hexahydro-1H-benzo[7]annulene; (1R,4aS,8aS)-1-isopropyl-7-methyl-4-methylene-1,2,3,4,4a,5,6,8a-octahydronaphthalene; furan-2-ylmethyl hexanoate; 2-methyldecanenitrile; ethyl (3aR,4S,7R,7aR)-octahydro-3aH-4,7-methanoindene-3a-carboxylate; (E)-4,8-dimethyldeca-4,9-dienal; 2-heptylcyclopentan-1-one; 3-cyclohexene-1-carboxylic acid, 2,6,6-trimethyl-, methyl ester; 4-allyl-2-methoxyphenol; ethyl nonanoate; nonan-3-one;

ethyl decanoate; ethyl 6,6-dimethyl1-2-methylenecyclohex-3-ene-1-carboxylate; (2-(1-ethoxyethoxy)ethyl)benzene; 1,1-dimethoxydodecane; (R)-1-methyl-4-(prop-1-en-2-yl)cyclohex-1-ene; diphenylmethane; 2,6-dimethyloct-7-en-4-one; octahydro-1H-4,7-methanoinden-5-yl acetate; 2-methyl-5-(prop-1-en-2-yl)cyclohexyl acetate; 2-methyl-5-(prop-1-en-2-yl)cyclohexan-1-ol; 3,7-dimethyloct-6-en-3-ol; dibutylsulfane; (3R,4R)-1-isopropyl-4-methyl-3-(prop-1-en-2-yl)-4-vinylcyclohex-1-ene; (Z)1-((1R,2S)-2,6,6-trimethylcyclohex-3-en-1-yl)but-2-en-1-one; 3,7,7-trimethylbicyclo[4.1.0]hept-3-ene; decyl propionate; 1,1-diethoxydecane; decahydronaphthalen-2-ol; 1-cyclohexylethyl (E)-but-2-enoate; (4-isopropylphenyl)methanol; (E)-2-(2,6-dimethylhepta-1,5-dien-1-yl)-4-methyl-1,3-dioxolane; (E)-1,1-dimethoxy-3,7-dimethylocta-2,6-diene; (E)-3,7-dimethylocta-1,3,6-triene; (1R,4R,6S)-1-methyl-4-(prop-1-en-2-yl)-7-oxabicyclo[4.1.0]heptane; (1R,5R)-2-methyl-5-(prop-1-en-2-yl)cyclohex-2-en-1-ol; (Z)-dec-4-enal; (E)-hex-3-en-1-yl (E)-hex-3-enoate; (Z)-hex-3-en-1-yl 2-methylbutanoate; (3Z,6Z)-nona-3,6-dien-1-ol; cinnamyl formate; (E)-3-phenylprop-2-en-1-ol; (3R,3aR,6S,7S,8aS)-6-methoxy-3,6,8,8-tetramethyloctahydro-1H-3a,7-methanoazulene; octanenitrile; octan-1-ol; octanoic acid; decanal; 3-(4-methoxyphenyl)-2-methylpropanal; 1,7,7-trimethylbicyclo[2.2.1]heptane-2,3-dione; 2,2-dimethyl-3-methylenebicyclo[2.2.1]heptane; (1S,2S)-1,7,7-trimethylbicyclo[2.2.1]heptan-2-yl isobutyrate; 1,7,7-trimethylbicyclo[2.2.1]heptan-2-yl acetate; 2-ethoxy-2,6,6-trimethyl-9-methylenebicyclo[3.3.1]nonane; 3,3,6,7-tetramethyloctahydro-2H-chromene; 1-methyl-4-(prop-1-en-2-yl)cyclohexyl acetate; 1-methyl-4-(prop-1-en-2-yl)cyclohexan-1-ol; (R)-3-methylene-6-((S)-6-methylhept-5-en-2-yl)cyclohex-1-ene; (4aR,7R,8aS)-4a-methyl-1-methylene-7-(prop-1-en-2-yl)decahydronaphthalene; 6,6-dimethyl-2-methylenebicyclo[3.1.1]heptane; (1S,4R,7R)-1,4,9,9-tetramethyl-1,2,3,4,5,6,7,8-octahydro-4,7-methanoazulene; (2,2-dimethoxyethyl)benzene; (E)-7,11-dimethyl-3-methylenedodeca-1,6,10-triene; (1R,2S,6S,7S,8S)-8-isopropyl-1-methyl-3-methylenetricyclo[4.4.0.02,7]decane; (3R,3aS,7S,8aS)-3,8,8-trimethyl-6-methyleneoctahydro-1H-3a,7-methanoazulene; (1R,9S,Z)-4,11,11-trimethyl-8-methylenebicyclo[7.2.0]undec-4-ene; 2-methyl-4-phenylbutan-2-ol; 2-methyl-1-phenylpropan-2-ol; 2'-isopropyl-1,7,7-trimethylspiro[bicyclo[2.2.1]heptane-2,4'-[1,3]dioxane]; methyl (E)-octa-4,7-dienoate; (1S,4R,5R)-1-isopropyl-4-methylbicyclo[3.1.0]hexan-3-one; 2-(4-methylcyclohex-3-en-1-yl)propan-2-yl propionate; (2R,4aR,8aR)-4a,8-dimethyl-2-(prop-1-en-2-yl)-1,2,3,4,4a,5,6,8a-octahydronaphthalene; 1,7-dimethyl-7-(4-methylpent-3-en-1-yl)tricyclo[2.2.1.02,6]heptane; (1R,3aS,7S,8aR)-1,4,9,9-tetramethyl-2,3,6,7,8,8a-hexahydro-1H-3a,7-methanoazulene; (1S,4aS,8aR)-1-isopropyl-4,7-dimethyl-1,2,4a,5,6,8a-hexahydronaphthalene; 1-methyl-4-(prop-1-en-2-yl)cyclohex-1-ene; (1aR,4R,4aR,7bS)-1,1,4,7-tetramethyl-1a,2,3,4,4a,5,6,7b-octahydro-1H-cyclopropa[e]azulene; 7,7-dimethyl-2-methylenebicyclo[2.2.1]heptane; (3aR,3bR,4S,7R,7aS)-4-isopropyl-7-methyl-3a,3b,4,5,6,7-hexahydro-1H-cyclopenta[1,3]cyclopropa[1,2]benzene; (1aS,2aR,3R,5aS,7R,7aR)-3,6,6,7a-tetramethyloctahydro-2H-2a,7-methanoazuleno[5,6-b]oxirene; (1S,4aR,8aR)-1-isopropyl-4,7-dimethyl-1,2,4a,5,6,8a-hexahydronaphthalene; 2,6-dimethyl-6-(4-methylpent-3-en-1-yl)bicyclo[3.1.1]hept-2-ene; (1S,4aR,8aS)-1-isopropyl-4,7-dimethyl-1,2,4a,5,6,8a-hexahydronaphthalen-2-ol; 1-phenylpropan-2-ol; trans,Trans-2,4-nonadien-1-al; alpha-4-Dimethyl benzenepropanal; allyl 2-(isopentyloxy)acetate; (1aR,4aS,7R,7aR,7bS)-1,1,7-trimethyl-4-methylenedecahydro-1H-cyclopropa[e]azulene; (E)-undec-9-enal; nonyl acetate; (2-(1-propoxyethoxy)ethyl)benzene; 1-(1-propoxyethoxy)propane; ((1-(2-methoxyethoxy)ethoxy)methyl)benzene; dec-9-enal; (2S,4aR,8aR)-4a,8-dimethyl-2-(prop-1-en-2-yl)-1,2,3,4,4a,5,6,8a-octahydronaphthalene; 6-isopropylquinoline; 3-(6,6- dimethylbicyclo[3.1.1]hept-2-en-2-yl)propanal; 2-methyl-5-(prop-1-en-2-yl)-2-vinyltetrahydrofuran; 1-isopropyl-4-methylcyclohex-3-en-1-ol; 1-phenylpent-4-en-1-one; 1-isopropyl-4-methylcyclohex-3-en-1-ol; 3,6-dimethyl-4,5,6,7-tetrahydrobenzofuran; (Z)-dodec-2-enal; (E)-hex-3-en-1-yl 3-methylbutanoate; 3,6-dimethyloctan-3-yl acetate; 3-(4-isopropylphenyl)propanal; (Z)-undec-2-enenitrile; (E)-undec-2-enal; (2E,6E)-nona-2,6-dienal; 2-phenoxyethan-1-ol; (Z)-non-2-enal; nonan-2-ol; nonan-2-one; (E)-2-hexylidenecyclopentan-1-one; 2-heptyltetrahydrofuran; (E)-dec-2-enal; (2E,6E)-nona-2,6-dienal; (2E,6E)-nona-2,6-dien-1-ol; 2,6-dimethyloctanal; decan-1-ol; (E)-hept-1-en-1-yl acetate; undec-10-enal; 1-isopropyl-4-methyl-7-thiabicyclo[2.2.1]heptane; (3E,5Z)-undeca-1,3,5-triene; 3,7-dimethyloct-6-en-3-ol; 1,3,3-trimethylbicyclo[2.2.1]heptan-2-yl acetate; 1,1,2,3,3-pentamethyl-2,3-dihydro-1H-indene; (Z)-dodec-3-enal; (1S,2S,5S)-2-methyl-5-(prop-1-en-2-yl)cyclohexan-1-ol; (2S,5R)-2-isopropyl-5-methylcyclohexan-1-one; 3-(3-isopropylphenyl)butanal; 2-methyl-5-(6-methylhept-5-en-2-yl)bicyclo[3.1.0]hex-2-ene; 2-(m-tolyl)ethan-1-ol; (3E,6E)-nona-3,6-dien-1-ol; p-tolyl isobutyrate; 4-(prop-1-en-2-yl)cyclohex-1-ene-1-carbaldehyde; (4-(prop-1-en-2-yl)cyclohex-1-en-1-yl)methyl acetate; (2-isopropoxyethyl)benzene; 2-phenylethan-1-ol; 2-benzyl-1,3-dioxolane; 2-(6,6-dimethylbicyclo[3.1.1]hept-2-en-2-yl)acetaldehyde; 6,6-dimethyl-2-methylenebicyclo[3.1.1]heptan-3-ol; 4-isopropyl-1-methylcyclohex-3-en-1-ol; propane-1,2-diol; 2,4-dimethyl-4-phenyltetrahydrofuran; (Z)-6-ethylideneoctahydro-2H-5,8-methanochromene; methyl 2,2-dimethyl-6-methylenecyclohexane-1-carboxylate; 4-methyl-2-phenyl-3,6-dihydro-2H-pyran; (1S,3R,5S)-1-isopropyl-4-methylenebicyclol[3.1.0]hexan-3-ol; 5-allylbenzo[d][1,3]dioxole; (4aR,8aR)-4a,8-dimethyl-2-(propan-2-ylidene)-1,2,3,4,4a,5,6,8a-octahydronaphthalene; 2-methyl-1,5-dioxaspirol[5.5]undecane; 2-(heptan-3-yl)-1,3-dioxolane; (Z)-dodec-4-enal; 3-methyl-2-pentylcyclopentan-1-one; 2,6,10,10-tetramethyl-1-oxaspirol[4.5]dec-6-ene; (1aR,4aS)-2,4a,8,8-tetramethyl-1,1a,4,4a,5,6,7,8-octahydrocyclopropal[d]naphthalene; 1-isopropyl-2-methoxy-4-methylbenzene; (2Z,4E)-nona-2,4-dienal; (2E,6Z)-nona-2,6-dienal; (Z)-dec-2-enal; (E)-non-2-enal; (3E,6Z)-nona-3,6-dien-1-ol; (E)-dec-4-enal; (Z)-3,7-dimethylocta-1,3,6-triene; (Z)-3,7-dimethylocta-1,3,6-triene; (E)-3,7-dimethylocta-2,6-dien-1-ol; undecanal; (E)-4-methyldec-3-en-5-ol; (3R,4aS,5R)-4a,5-dimethyl-3-(prop-1-en-2-yl)-1,2,3,4,4a,5,6,7-octahydronaphthalene; 1-methoxy-3a,4,5,6,7,7a-hexahydro-1H-4,7-methanoindene; (Z)-hex-3-en-1-yl isobutyrate; decahydro-3H-spiro[furan-2,5'-[4,7]methanoindene]; (2Z,6E)-nona-2,6-dienenitrile; 1',1',5',5'-tetramethylhexahydro-2'H,5'H-spiro[[1,3]dioxolane-2,8'-[2,4a]methanonaphthalene]; (2'S,4a'S,8a'S)-1',1',5',5'-tetramethylhexahydro-2'H,5'H-spiro[[1,3]dioxolane-2,8'-[2,4a]methanonaphthalene]; 1-ethoxy-4-(tert-pentyl)cyclohexane; (3Z)-1-(2-buten-1-yloxy)-3-hexene; 4-(2-methoxypropan-2-yl)-1-methylcyclohex-1-ene; 3-methoxy-3,7-dimethylocta-1,6-diene; 3,7-dimethyloctanal; 3,3-Dimethyl-5 (2,2,3-Trimethyl-3-Cyclopenten-1yl)-4-Penten-2-O1; hexyl (Z)-but-2-enoate; (Z)-3,7-dimethylocta-2,6-dien-1-yl formate; (E)-2,2-dimethyl-3-(3-methylpenta-2,4-dien-1-yl)oxirane; (E)-3,7-dimethylocta-4,6-dien-3-ol; (Z)-hex-3-en-1-yl cyclopropanecarboxylate; 1-phenylethyl propionate; methyl 2-phenylacetate; methyl (Z)-3,7-dimethylocta-2,6-dienoate; methyl 2-cyclopentylideneacetate; 6-methoxy-2,6-dimethylheptanal; ((1s,4s)-4-isopropylcyclohexyl)methanol; 3,7-dimethylocta-1,6-dien-3-yl propionate; 3,7-dimethylocta-1,6-dien-3-yl formate; 3,7-dimethylocta-1,6-dien-3-yl acetate; 3,7-dimethylocta-1,6-dien-3-ol; (Z)-hex-3-en-1-yl methyl carbonate; 4-methylquinoline; 2-Methyl-5-(1-methylethenyl)-2-cyclohexenone; 4-methylpent-1-en-3-ol; isopropyl 2-methylbutanoate; 4-methylpent-4-en-2-yl isobutyrate; 7-methyloctyl acetate; 7-methyloctan-1-ol; 1,7,7-trimethylbicyclo[2.2.1]heptan-2-ol; isopentyl octanoate; isopentyl isobutyrate; 2-phenylpropan-1-ol; hexyl propionate; hexyl butyrate; hexyl 2-methylbutanoate; heptan-1-ol; heptyl acetate; heptanal; benzo[d][1,3]dioxole-5-carbaldehyde; (Z)-3,7-dimethylocta-2,6-dienenitrile; (E)-3,7-dimethylocta-2,6-dien-1-yl formate; (E)-3,7-dimethylocta-2,6-dienal; 1-isopropyl-4-methylcyclohexa-1,4-diene; 2-(sec-butyl)cyclohexan-1-one; 3-(2-ethylphenyl)-2,2-dimethylpropanal; (Z)-5-methylhept-2-en-4-one; 1,3,3-trimethylbicyclo[2.2.1]heptan-2-ol; 1,3,3-trimethyl-2-oxabicyclo[2.2.2]octane; ethyl octanoate; ethyl 2-cyclohexylpropanoate; (2R,5R)-2-methyl-5-(prop-1-en-2-yl)cyclohexan-1-one; 4-methyl-2-phenyltetrahydro-2H-pyran; 2,6-dimethyloct-7-en-2-ol; 3-methyl-2-pentylcyclopent-2-en-1-one; 3,3,5-trimethylcyclohexan-1-one; 2-methyl-5-(prop-1-en-2-yl)cyclohexan-1-one; 2-(4-methylcyclohexyl)propan-2-yl acetate; 4-(2,6,6-trimethylcyclohex-2-en-1-yl)butan-2-one; 2-pentylcyclopentan-1-one; methyl (1s,4s)-1,4-dimethylcyclohexane-1-carboxylate; 2-cyclohexylethyl acetate; 2-methoxy-4-methylphenol; (3Z,5Z)-2,6-dimethylocta-1,3,5,7-tetraene; 4-cyclohexyl-2-methylbutan-2-ol; 3,7-dimethyloct-6-enenitrile; 3,7-dimethyloct-6-en-1-yl formate; 3,7-dimethyloct-6-en-1-ol; 3,7-dimethyloct-6-enal; (E)-3,7-dimethylocta-2,6-dienal; (1R,2S,5R)-2,6,6-trimethylbicyclo[3.1.1]heptane; (Z)-hex-3-en-1-yl pentanoate; (E)-hex-3-en-1-yl (E)-2-methylbut-2-enoate; (Z)-hex-3-en-1-yl propionate; (Z)-hex-3-en-1-yl butyrate; (Z)-hex-3-en-1-ol; (Z)-hex-2-en-1-ol; cinnamonitrile; cinnamaldehyde; cinnamonitrile; 4-chloro-3,5-dimethylphenol; 5-isopropyl-2-methylphenol; 2-methyl-5-(prop-1-en-2-yl)cyclohex-2-en-1-one; 2-(2-ethoxyethoxy)ethan-1-ol; hexan-1-ol; 2-(2,2,3-trimethylcyclopent-3-en-1-yl)acetonitrile; 1,7,7-trimethylbicyclo[2.2.1]heptan-2-one; (1S,2R,4S)-1,7,7-trimethylbicyclo[2.2.1]heptan-2-ol;6,6-dimethylspiro[bicyclo [3.1.1]heptane-2,2'-oxirane]; 3-isopropyl-6-methylenecyclohex-1-ene; 4-phenylbutan-2-one; benzyl 3-methylbutanoate; benzyl isobutyrate; benzyl butyrate; phenylmethanol; 1-(3,3-dimethylcyclohexyl)ethyl formate; 4-methoxybenzyl acetate; 4-methoxybenzyl formate; (Z)-1-methoxy-4-(prop-1-en-1-yl)benzene; 2-(4-methylcyclohex-3-en-1-yl)propan-2-yl acetate; 4-cyclohexylbutan-2-ol; (E)-2-methyl-3-phenylacrylaldehyde; 4-methoxy-2,5-dimethylfuran-3(2H)-one; (2-(allyloxy)ethyl)benzene; allyl heptanoate; 3-hydroxybutan-2-one; 1-(4-methoxyphenyl)ethan-1-one; 6-methylquinoline; 6,8-dimethylnonan-2-ol; 5-methylheptan-3-one; 4-vinylphenol; 4-ethyl-2-methoxyphenol; 3-methylcyclopentane-1,2-dione; 3-methoxy-3-methylbutan-1-ol; (E)-hex-3-en-1-ol; 3,7-dimethyl-2-methyleneoct-6-enal; 3,7-dimethyloctan-1-ol; phenethyl acetate; phenethyl propionate; 2-pentylcyclopentan-1-ol; (2S,4S)-2-heptyl-2,4-dimethyl-1,3-dioxolane; 2-(sec-butyl)-3-methoxypyrazine; 2-isopropyl-N,2,3-trimethylbutanamide; (E)-2-isopropyl-5-methylhex-2-enal; 2-isopropyl-4-methylthiazole; (E)-hex-2-en-1-ol; 2-butoxyethan-1-ol; 1-isopropyl-4-methyl-7-oxabicyclo[2.2.1]heptane; (Z)-hept-3-en-1-yl acetate; (1S,5S)-4,6,6-trimethylbicyclo[3.1.1]hept-3-en-2-one; (R)-3,7-dimethylocta-1,6-dien-3-ol; 3,7-dimethyloct-6-enal; (R)-3,7-dimethyloct-6-enal; 3,7-dimethyloct-6-en-1-ol; 3,7-dimethyloct-6-en-1-ol; (1R,5R)-2,6,6-trimethylbicyclo[3.1.1]hept-2-ene; (S)-2-methyl-5-(prop-1-en-2-yl)cyclohex-2-en-1-one; (1S,5S)-2,6,6-trimethylbicyclo[3.1.1]hept-2-ene; methyl 2-methylbutanoate; hexyl (Z)-2-methylbut-2-enoate; 1-phenylvinyl acetate; p-cymene; phenethyl formate; 2-(4-isopropylphenyl)acetaldehyde; 1,2-dimethyl-3-(prop-1-en-2-yl)cyclopentan-1-ol; (2Z,5Z)-5,6,7-trimethylocta-2,5-dien-4-one; 1-methoxy-4-propylbenzene; 2-(4-(tert-butyl)phenyl)acetaldehyde; 4-(tert-pentyl)cyclohexan-1-ol; 2,6,6-trimethylbicyclo[3.1.1]hept-2-ene; 3,7-dimethyloct-7-en-1-ol; 1-(3,3-dimethylcyclohexyl)ethyl acetate; (S)-3,7-dimethylocta-1,6-dien-3-ol; 1-isopropyl-4-methylenebicyclo[3.1.0]hexane; 5-isopropyl-2-methylbicyclo[3.1.0]hexan-2-ol; propyl (S)-2-(tert-pentyloxy)propanoate; 1-oxaspiro(4,5)decan-2-one; (Z)-5-methylheptan-3-one oxime; 1-phenylethyl acetate; 3,7-dimethyloctanal; 3,7-dimethyloctan-3-ol; 3,7-dimethyloctan-3-yl acetate; ethyl (1R,6S)-2,2,6-trimethylcyclohexane-1-carboxylate; (E)-hex-2-en-1-ol; (1R,2S)-2-(tert-butyl)cyclohexan-1-ol; (Z)-1-methoxy-4-(prop-1-en-1-yl)benzene; (2R,5R)-2-methyl-5-(prop-1-en-2-yl)cyclohexan-1-one; 2-mercapto-2-methylpentan-1-ol; 2,2,5-trimethyl-5-pentylcyclopentan-1-one; (1R,5R)-4,6,6-trimethylbicyclo[3.1.1]hept-3-en-2-one; 2-(tert-butyl)cyclohexan-1-ol; (4-tert-butylcyclohexyl) acetate; 4-(tert-butyl)cyclohexyl acetate; (Z)-1-((2-methylallyl)oxy)hex-3-ene and mixtures thereof.

7. A freshening composition according to claim 1, wherein said malodor reduction materials are not selected from the group consisting of geranyl nitrile; helional; nonanal; linalool; (S)-(+)-linalool; (R)-(−)-linalool; nerol; tetrahydrolinalool; 2-phenylethyl acetate; eugenol; ethyl linalool; allyl heptoate; agrumen nitrile; citronitrile; 2,2-dimethyl-3-(m-tolyl)propan-1-ol; 2-methyl-5-phenylpentan-1-ol; dodecanenitrile; 2-heptylcyclopentan-1-one; methyl nonyl acetaldehyde; 3-(2-ethylphenyl)-2,2-dimethylpropanal; (Z)-1-(2,6,6-trimethylcyclohex-2-en-1-yl)but-2-en-1-one; (R,E)-2-methyl-4-(2,2,3-trimethylcyclopent-3-en-1-yl)but-2-en-1-ol; 4-(tert-butyl)cyclohexyl acetate; 1-cyclohexylethyl (E)-but-2-enoate; allyl 2-(cyclohexyloxy)acetate; alpha terpinyl acetate; beta terpinyl acetate; gamma terpinyl acetate; methyl dodecyl ether; 2,4-dimethyl-4,4a,5,9b-tetrahydroindeno[1,2-d][1,3]dioxine; cinnamyl isobutyrate; (E)-2-methyl-4-(2,6,6-trimethylcyclohex-1-en-1-yl)but-2-enal; gamma methyl ionone; ethyl 2,3,6-trimethyl cyclohexyl carbonate ethyl 2,3,6-trimethyl cyclohexyl carbonate; Citral diethyl acetal; Dimethoxycyclododecane; 1-((2S,3S)-2,3,8,8-tetramethyl-1,2,3,4,5,6,7,8-octahydronaphthalen-2-yl)ethan-1-one; oxacyclohexadecan-2-one; 4,6,6,7,8,8-hexamethyl-1,3,4,6,7,8-hexahydrocyclopenta[g]isochromene; Ethylene brassylate; Methyl (Z)-2-((3-(4-(tert-butyl)phenyl)-2-methylpropylidene)amino)benzoate; 4,7-Methano-1H-inden-5-ol, 3a,4,5,6,7,7a-hexahydro-, 5-acetate; cedryl methyl ether; vetivert acetate; 1-((3R,3aR,7R,8aS)-3,6,8,8-tetramethyl-2,3,4,7,8,8a-hexahydro-1H-3a,7-methanoazulen-5-yl)ethan-1-one; Benzophenone; Farnesol; trans,trans-farnesol; 3-(3-isopropylphenyl)butanal; 2,6,10-trimethylundec-9-enal; 3-(4-(tert-butyl)phenyl)propanal; 3-(4-isopropylphenyl)-2-methylpropanal; Citronellal (1); Citronellal (d); (E)-4,8-dimethyldeca-4,9-dienal; Pino Acetaldehyde; 3-(4-(tert-butyl)phenyl)-2-methylpropanal; Cinnamic aldehyde; Citral; Geranial; MethoxyMelonal; o-methoxycinnamaldehyde; (E)-4-((3aS,7aS)-octahydro-5H-4,7-methanoinden-5-ylidene)butanal; Methyl Octyl Acetaldehyde; 3-(4-methoxyphenyl)-2-methylpropanal; 5-methoxyoctahydro-1H-4,7-methanoindene-2-carbaldehyde; Iso Cyclocitral; Octanal; 2-Undecenal; 10-Undecenal; Trans-trans-2,6-Nonadienal; Trans-2,cis-6-nondienal; Heliotropin; Hexyl Cinnamic aldehyde; p-methyl-alpha- pentylcinnamaldehyde; Alpha-methyl cinnamaldehyde; 3,4-dimethoxybenzaldehyde; Myrtenal; Perillaldehyde; Maceal; Methyl palmitate; Methyl iso eugenol and mixtures thereof.

8. A freshening composition according to claim 1, said freshening composition comprising a thickening or gelling agent.

9. A composition according to claim 1, said composition comprising an adjunct ingredient selected from the group consisting of:
 colorant and dyes,
 solvents and diluents selected form the group consisting of glycol ethers,
 alcohols, liquid hydrocarbons, and esters of acetic acid, gluconic acid, adipic
 acid, glutaric, benzoic acid succinic acid, and combinations thereof,
 preservatives;
 UV absorbers,
 insect repellants,
 antimicrobial agents,
 fragrances and aromatherapy agents,
 and mixtures thereof.

10. A device comprising the freshening composition of claim 1, said device being selected from the group consisting of energized air fresheners and non energized air fresheners.

11. A freshening composition according to claim 1 comprising one or more perfume raw materials other than said sum total of malodor reduction materials, the ratio of said one or more perfume raw materials to said sum total of malodor reduction material being from about 1,000,000:1 to about 1:1.

12. A freshening composition according to claim 11, wherein less than 10% of said malodor reduction materials and said one or more perfume rawmaterials, based on total combined weight of malodor reduction materials and said one or more perfume raw materials, comprise an unsaturated aldehyde moiety.

13. A freshening composition according to claim 11, wherein less than 50% of said malodor reduction materials and said one or more perfume raw materials, based on total combined weight of malodor reduction materials and said one or more perfume raw materials has a vapor pressure of from about 0.000375 to about 4.00.

14. A method of controlling malodors comprising: dispensing the composition of claim 1 into the air.

15. The method of claim 14 wherein said dispensing comprises dispensing the composition to provide said air with from about 0.1 nanogram (ng) to about 5000 ng of said sum of malodor reduction materials per liter of said air.

* * * * *